(12) United States Patent
Suzuki et al.

(10) Patent No.: US 7,575,910 B2
(45) Date of Patent: Aug. 18, 2009

(54) METHOD FOR PRODUCING L-FUCULOSE AND METHOD FOR PRODUCING L-FUCOSE

(75) Inventors: Shunichi Suzuki, Kawasaki (JP); Kunihiko Watanabe, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 61 days.

(21) Appl. No.: 11/532,618

(22) Filed: Sep. 18, 2006

(65) Prior Publication Data
US 2007/0026504 A1 Feb. 1, 2007

Related U.S. Application Data

(63) Continuation of application No. PCT/JP2005/004701, filed on Mar. 16, 2005.

(30) Foreign Application Priority Data
Mar. 17, 2004 (JP) .............................. 2004-077117

(51) Int. Cl.
C12N 9/02 (2006.01)
C12N 1/20 (2006.01)
C12P 19/02 (2006.01)
C07H 21/04 (2006.01)

(52) U.S. Cl. .................... 435/189; 435/252.3; 435/105; 536/23.2

(58) Field of Classification Search ........................ None
See application file for complete search history.

(56) References Cited

U.S. PATENT DOCUMENTS 5,747,301 A 5/1998 Hoshino et al.

FOREIGN PATENT DOCUMENTS

| JP | 59-51798 | 3/1984 |
| JP | 61-057520 | 3/1986 |
| JP | 05-308984 | 11/1993 |
| JP | 06-090765 | 4/1994 |
| JP | 08-242850 | 9/1996 |
| JP | 11-035591 | 2/1999 |
| WO | WO97/15683 | 5/1997 |
| WO | WO02/06506 | 1/2002 |

OTHER PUBLICATIONS

Prust et al. Complete genome sequence of the acetic acid bacterium *Gluconobacter oxydans*, Nat Biotechnol. Feb. 2005;23(2):195-200. Epub Jan. 23, 2005.*
Adachi, O., et al., "Membrane-bound Quinoprotein D-Arabitol Dehydrogenase of *Gluconobacter suboxydans* IFO 3257: A Versatile Enzyme for the Oxidative Fermentation of Various Ketoses," Biosci. Biotechnol. Biochem. 2001;65(12):2755-2762.
Huwig, A., et al., "Enzymatic synthesis of L-tagatose from galactitol with galactitol dehydrogenase from *Rhodobacter sphaeroides* D," Carbohydrate Res. 1998;305:337-339.
Richtmyer, N., et al., "L-Fuco-4-ketose, a New Sugar Produced by the Action of *Acetobacter suboxydans* on L-Fucitol," J. Am. Chem. Soc. 1950;72:4934-4937.
Sarbajna, S., et al., "A novel synthesis of L-fucose from D-galactose," Carbohydrate Res. 1995;270:93-96.
Seemann, J. E., et al., „Structure and Mechanism of L-Fucose Isomerase from *Escherichia coli*, J. Mol. Biol. 1997;273:256-268.
Stein, R., et al., "Characterization of a xylitol dehydrogenase and a D-arabitol dehydrogenase from the thermo- and acidophilic red alga *Galdieria sulphuraria*," Plant 1997;202:487-493.
Sugiyama, M., et al., "Cloning of the Xylitol Dehydrogenase Gene from *Gluconobacter oxydans* and Improved Production of Xylitol from D-Arabitol," Biosci. Biotechnol. Biochem. 2003;67(3):584-591.
Vanhooren, P.T., et al., "L-Fucose: occurrence, physiological role, chemical, enzymatic and microbial synthesis," J. Chem. Technol. Biotechnol. 1999;74:479-497.
Williams, D. T., et al., "Further experiments on the oxidation of sugar acetals and thioacetals by *Acetobacter suboxydans*," Can. J. Chem. 1967;45:741-744.
International Search Report for PCT Patent App. No. PCT/JP2005/004701 (Apr. 26, 2005).

* cited by examiner

*Primary Examiner*—Andrew Wang
*Assistant Examiner*—Iqbal H Chowdhury
(74) *Attorney, Agent, or Firm*—Shelly Guest Cermak; Cermak Kenealy Vaidya & Nakajima LLP

(57) ABSTRACT

The present invention provides a method for producing L-fuculose and L-fucose which is suitable as an industrial method. L-Fuculose is synthesized from L-fucitol in the presence of a microorganism-derived protein having a dehydrogenase activity which results in production of L-fuculose from L-fucitol. The reaction system preferably contains NADH oxidase. L-Fuculose thus synthesized is then converted into L-fucose.

24 Claims, 20 Drawing Sheets ent for a cancer metastasis inhibi-
METHOD FOR PRODUCING L-FUCULOSE AND METHOD FOR PRODUCING L-FUCOSE This application claims priority under 35 U.S.C. §119(a) to JP 2004-077117, filed in Japan on Mar. 17, 2004, and is a continuation under 35 U.S.C. §120 of PCT/JP2005/004701, filed on Mar. 16, 2005, the entireties of which are incorporated by reference. The Sequence Listing on Compact Disk filed herewith is also hereby incorporated by reference in its entirety (File Name: US-302 Seq List; File Size: 28 KB; Date Created: Sep. 18, 2006).

BACKGROUND OF THE INVENTION

1. Field of the Invention

The present invention relates to simple and efficient methods for producing L-fuculose and L-fucose.

2. Brief Description of the Related Art

L-Fucose (L-6-deoxygalactose) is ubiquitous throughout the living world, mostly as a non-reducing terminal sugar of various carbohydrates. For example, fucoidan in seaweed is a polysaccharide which contains L-fucose. L-Fucose is believed to be involved in the uptake of serum glycoprotein into the liver, and is able to induce receptors for macrophage migration inhibitory factor in vivo. L-Fucose has also been studied relative to its association with various diseases. For example, L-fucose has been studied as a pharmaceutical intermediate. Specifically, researchers are hoping to develop the ability to diagnose cancer based on the ratio of L-fucose in glycoprotein or glycolipid, or the change in the amount of free L-fucose in urine. Development of a cancer metastasis inhibitory agent and an antivirus agent with L-fucose is also anticipated. It is further anticipated to utilize L-fucose for controlling leukocytes and treating rheumatoid arthritis.

As described above, various applications of L-fucose are being developed for future use. However, methods for obtaining and producing L-fucose have already been developed. For example, methods for extracting fucoidan from *Nemacystus decipiens* (PJP S61-57520 A), and isolating L-fucose from fucoidan derived from *Nemacystus decipiens* have been described (JP H11-35591 A). However, a large amount of *Nemacystus decipiens* is required to perform these methods. In addition, it is difficult to isolate and purify the product with these methods, and the yield is small.

Isolation of L-fucose from a hydrolyzed polysaccharide produced by a microorganism has also been attempted and described (JP S59-51798 A). However, isolation and purification are also technically difficult using this method, and the yield again is also very small. A chemical synthesis method using D-galactose as a raw material has also been described (JP S61-57520 A); however, this method is not industrially practical because of the many steps which are necessary and the small yield.

As a synthetic method using an enzyme, converting L-fuculose-1-phosphate into L-fuculose using acid phosphatase and further converting into L-fucose using L-fucose isomerase has been described (International Publication WO97/15683 Pamphlet). However, L-fuculose-1-phosphate is expensive. Therefore, there is a demand in the art for a method which enables production at lower cost.

Oxidation of L-fucitol using NAD-dependent dehydrogenase derived from plants (Rhodophyta, red algae) has been reported (e.g., International Publication WO02/06506 Pamphlet; Planta 202: 487-493 (1997)). However, it is unclear which site of L-fucitol is oxidized, and the resulting products have not been definitely identified. In addition, it is generally difficult to produce an enzyme derived from a plant on a large scale for industrial applications, and thus, this method is inconvenient.

Furthermore, the oxidation of L-fucitol using *acetobacterium* has been reported (e.g., Journal of American Chemical Society; 4934-4937 (1950), Canadian Journal of Chemistry 45: 741-744 (1967)). However, no enzyme has been identified in these reports. The oxidation products are different depending on the oxidized site of L-fucitol. In these experimental reports, the major component of the resulting oxide has been reported to be not L-fucose or L-fuculose, but a substance resulting from oxidation at position 4 of L-fucitol (L-fuco-4-ketose in Journal of American Chemical Society; 4934-4937 (1950)). The *acetobacterium* has been extensively studied in relation to the enzyme acting on a sugar as a substrate (e.g., JP H8-242850 A, Canadian Journal of Chemistry 45: 741-744 (1967), Biosci. Biotechnol. Biochem. 65: 2755-2762 (2001)).

Although methods for utilizing L-fucose have been described, none of these methods are industrially available. Therefore, methods for producing L-fucose are desirable in the art, particularly for industrial use, and which provide ease of use and at a reasonable cost.

SUMMARY OF THE INVENTION

In response to the need in the art for an efficient and less expensive method for producing L-fucose, a protein having a fucitol dehydrogenase activity was derived from a microorganism. Furthermore, techniques for synthesizing L-fuculose from L-fucitol when there is no protein which is able to synthesize a ketohexose other than L-fuculose from L-fucitol, or the activity thereof is inhibited. An industrially suitable method for producing L-fuculose, which is an intermediate in the production of L-fucose, is described, as well as an industrially advantageous method for producing L-fucose. That is, aspects of the present invention include the following.

One aspect of the present invention includes a method for producing L-fuculose comprising contacting L-fucitol with a protein derived from a microorganism, the protein having a dehydrogenase activity which results in the synthesis of L-fuculose from L-fucitol.

Another aspect includes a method for producing L-fuculose as described above, wherein the protein is isolated from an *acetobacterium*.

Another aspect includes a method for producing L-fuculose comprising contacting L-fucitol with a composition selected from the group consisting of a microorganism which is able to synthesize L-fuculose from L-fucitol so that the amount of L-fuculose is 50% by weight or more of total L-fucitol oxide, a culture of the microorganism, a treated microbial cell product of the microorganism, and combinations thereof.

Another aspect includes a method for producing L-fuculose comprising contacting L-fucitol with a composition selected from the group consisting of at least one microorganism of *Gluconobacter xylinus* subsp. *xylinus* and *Gluconobacter oxydans*, a culture of the microorganism, a treated microbial cell product of the microorganism, and combinations thereof.

Another aspect includes a method for producing L-fuculose comprising contacting L-fucitol with a composition selected from the group consisting of a microorganism having a protein having a dehydrogenase activity which results in the synthesis of L-fuculose from L-fucitol, the microorganism not having a substantial ability to synthesize a ketohexose, other than L-fuculose, from L-fucitol, a culture of the non-genetically engineered microorganism, a treated microbial cell product of the non-genetically engineered microorganism, and combinations thereof.

Another aspect includes producing L-fuculose as described above wherein a gene has been knocked out in said microorganism which encodes a protein having an activity which results in the synthesis of a ketohexose, other than L-fuculose, from L-fucitol.

Another aspect includes producing L-fuculose as described above, wherein the microorganism has been transformed to be capable of expressing said protein having a dehydrogenase activity.

Another aspect includes producing L-fuculose as described above, wherein a gene has been knocked out in said microorganism which encodes a protein having an activity which results in the synthesis of a ketohexose, other than L-fuculose, from L-fucitol.

Another aspect includes producing L-fuculose as described above, wherein L-fuculose is synthesized from L-fucitol when synthesis of a ketohexose, other than L-fuculose, from L-fucitol is inhibited.

Another aspect includes producing L-fuculose as described above, wherein L-fuculose is synthesized from L-fucitol at a pH which inhibits synthesis of a ketohexose, other than L-fuculose, from L-fucitol.

Another aspect includes producing L-fuculose as described above, wherein L-fuculose is synthesized from L-fucitol in the presence of a bivalent ion chelator when synthesis of a ketohexose, other than L-fuculose, from L-fucitol is inhibited.

Another aspect includes producing L-fuculose as described above, wherein L-fuculose is synthesized from L-fucitol in the presence of a protein having an activity to produce NAD from NADH.

Another aspect includes producing L-fucose comprising synthesizing L-fuculose by contacting L-fucitol with a protein derived from a microorganism having a dehydrogenase activity which results in the synthesis of L-fuculose from L-fucitol, and synthesizing L-fucose by contacting L-fuculose with a protein having an activity to synthesize L-fucose from L-fuculose.

Another aspect includes producing L-fucose comprising synthesizing L-fuculose by contacting L-fucitol with a composition selected from the group consisting of a microorganism having an ability to synthesize L-fuculose from L-fucitol so that the amount of L-fuculose is 50% by weight or more of total L-fucitol oxide, a culture of the microorganism, a treated microbial cell product of the microorganism, and combinations thereof, and synthesizing L-fucose by contacting L-fuculose with a protein having an activity to synthesize L-fucose from L-fuculose.

Another aspect includes producing L-fucose comprising synthesizing L-fuculose by contacting L-fucitol with a composition selected from the group consisting of a microorganism having a protein having a dehydrogenase activity which results in the synthesis of L-fuculose from L-fucitol, wherein the microorganism does not have a substantial ability to synthesize a ketohexose, other than L-fuculose, from L-fucitol, a culture of the microorganism, a treated microbial cell product of the microorganism, and combinations thereof, and synthesizing L-fucose by contacting L-fuculose with a protein having an activity to synthesize L-fucose from L-fuculose.

Another aspect includes producing L-fucose as described above, wherein a gene has been knocked out in said microorganism, wherein said gene encodes a protein having an activity to synthesize a ketohexose, other than L-fuculose, from L-fucitol.

Another aspect includes producing L-fucose as described above, wherein said microorganism has been transformed to be capable of expressing a protein having a dehydrogenase activity which results in the synthesis of L-fuculose from L-fucitol.

Another aspect includes producing L-fucose as described above, wherein said microorganism expresses a protein having an activity to synthesize L-fucose from L-fuculose.

Yet another aspect of the present invention includes a protein selected from the group consisting of: (A) a protein comprising the amino acid sequence of SEQ ID NO:16, and (B) a protein comprising the amino acid sequence of SEQ ID NO.16, wherein said sequence includes one or several amino acid mutations selected from the group consisting of substitution, deletion, insertion, addition, and inversion, and having a dehydrogenase activity which results in the synthesis L-fuculose from L-fucitol.

Another aspect includes a polynucleotide encoding the protein as described above.

Another aspect includes a polynucleotide selected from the group consisting of: (A) a polynucleotide comprising the nucleotide sequence according to SEQ ID NO:15, and (B) a polynucleotide which hybridizes with a polynucleotide comprising a nucleotide sequence which is complementary to the nucleotide sequence of SEQ ID NO:15 under stringent conditions and encodes a protein having a dehydrogenase activity which results in the synthesis of L-fuculose from L-fucitol.

Another aspect includes a protein selected from the group consisting of: (A) a protein comprising the amino acid sequence of SEQ ID NO:18, and (B) a protein comprising the amino acid sequence of SEQ ID NO: 18, wherein said sequence includes one or several amino acid mutations selected from the group consisting of substitution, deletion, insertion, addition, and inversion, and having an NADH oxidase activity.

Another aspect includes a polynucleotide encoding the protein as described above.

Another aspect includes a polynucleotide selected from the group consisting of: (A) a polynucleotide comprising the nucleotide sequence of SEQ ID NO:17, and (B) a polynucleotide which hybridizes with a polynucleotide comprising a nucleotide sequence which is complementary to the nucleotide sequence of SEQ ID NO:17 under stringent conditions and encodes a protein having an activity to produce NAD from NADH.

Another aspect includes a recombinant polynucleotide comprising the polynucleotide described in paragraph [0032] incorporated therein.

Another aspect includes a recombinant polynucleotide comprising the polynucleotide described in paragraph [0035] incorporated therein.

Another aspect includes a recombinant polynucleotide comprising the polynucleotide described in paragraph [0032] and the polynucleotide described in paragraph incorporated therein.

Another aspect includes a transformant comprising the recombinant polynucleotide described in paragraph [0037], the transformant being capable of expressing a protein having a dehydrogenase activity which results in the synthesis L-fuculose from L-fucitol.

Another aspect includes a method for producing a protein comprising culturing the transformant described in paragraph [0040], wherein the transformant is a microorganism, in a medium wherein said protein accumulates in the medium and/or in the microorganism.

Yet another aspect includes a method for producing L-fuculose comprising adding to a reaction system containing L-fucitol a composition selected from the group consisting of the transformant described in paragraph [0040], wherein the transformant is a microorganism, a culture of the microorganism, a treated microbial cell product of the microorganism, and combinations thereof, wherein L-fuculose is synthesized from L-fucitol.

Another aspect includes a method for producing L-fucose comprising synthesizing L-fuculose by adding to a reaction system containing L-fucitol a composition selected from the group consisting of the transformant as described in paragraph [0040], wherein the transformant is a microorganism, a culture of the microorganism, a treated microbial cell product of the microorganism, and combinations thereof, wherein L-fuculose is synthesized from L-fucitol, and synthesizing L-fucose by contacting L-fuculose with a protein having an activity to synthesize L-fucose from L-fuculose.

Another aspect includes a transformant comprising the recombinant polynucleotide described in paragraph [0037] and the recombinant polynucleotide described in paragraph [0038] incorporated therein, the microorganism being capable of expressing a protein having a dehydrogenase activity which results in the synthesis of L-fuculose from L-fucitol and a protein having an activity to produce NAD from NADH.

Another aspect includes a method for producing a protein comprising culturing a microorganism which has been transformed with the recombinant polynucleotide described in paragraph [0038] in a medium, wherein said microorganism is capable of expressing said protein in the medium and/or in the microorganism.

Another aspect includes a method for producing L-fuculose comprising adding to a reaction system containing L-fucitol a composition selected from the group consisting of the transformant described in paragraph [0044], wherein the transformant is a microorganism, a culture of the microorganism, a treated microbial cell product of the microorganism, and combinations thereof, wherein L-fucolose is synthesized from L-fucitol.

Another aspect includes a method for producing L-fucose comprising synthesizing L-fuculose wherein one or more selected from the group consisting of the transformant described in paragraph [0044], wherein the transformant is a microorganism, a culture of the microorganism, a treated microbial cell product of the microorganism, and combinations thereof, are added to a reaction system containing L-fucitol, wherein L-fuculose is synthesized from L-fucitol, and synthesizing L-fucose by contacting L-fuculose with a protein having an activity to synthesize L-fucose from L-fuculose.

Another aspect includes a transformant comprising the recombinant polynucleotide described in paragraph [0039], the transformant being capable of expressing a protein having a dehydrogenase activity which results in the synthesis of L-fuculose from L-fucitol and a protein having an activity to produce NAD from NADH.

Another aspect includes a method for producing a protein having a degydrogenase activity which results in the synthesis of L-fuculose from L-fucitol and a protein having an activity to produce NAD from NADH comprising culturing the transformant described in paragraph [0048] in a medium, wherein the transformant is a microorganism, and wherein said proteins accumulate in the medium and/or in the microorganism.

Another aspect includes a method for producing L-fuculose comprising adding a composition selected from the group consisting of the transformant described in paragraph [0048], wherein the transformant is a microorganism, a culture of the microorganism, a treated microbial cell product of the microorganism, and combinations thereof, to a reaction system containing L-fucitol, wherein L-fuculose is synthesized from L-fucitol.

Another aspect includes a method for producing L-fucose comprising synthesizing L-fuculose wherein a composition selected from the group consisting of the transformant described in paragraph [0048], wherein the transformant is a microorganism, a culture of the microorganism, a treated microbial cell product of the microorganism, and combinations thereof are added to a reaction system containing L-fucitol, wherein L-fuculose is synthesized from L-fucitol, synthesizing L-fucose by contacting L-fuculose with a protein having an activity to synthesize L-fucose from L-fuculose.

BRIEF DESCRIPTION OF DRAWINGS

FIG. 20 (B) shows Lineweaver-Burk plot of (A).

DESCRIPTION OF THE PREFERRED EMBODIMENTS

Figure 1:
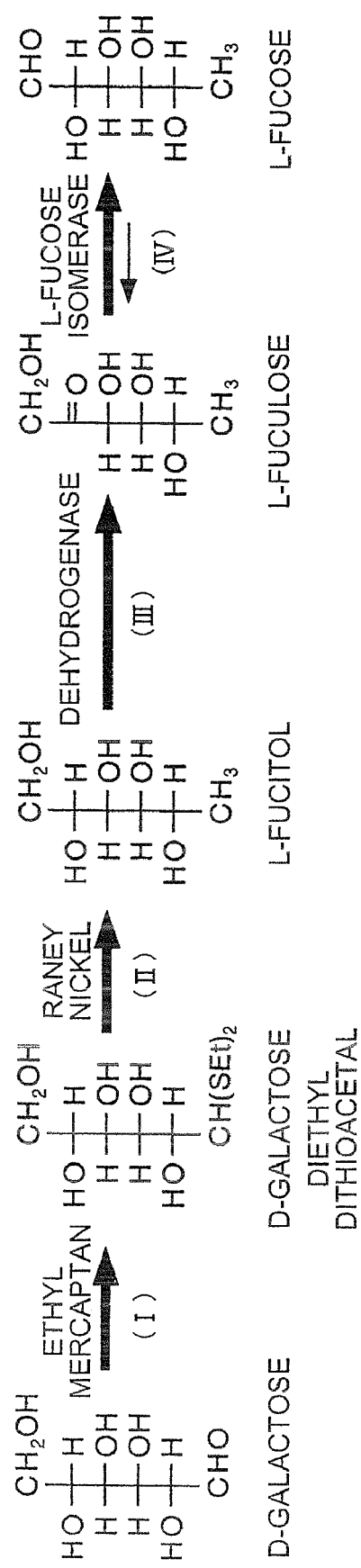
FIG. 1 shows the reaction process from D-galactose to L-fucose.

According to the present invention, industrially suitable methods for producing L-fuculose and L-fucose are provided. These production methods provide ease of use and are simple. These production methods can reduce or eliminate byproduct production, and are efficient. The production cost is reduced due to the use of D-galactose, which is inexpensive, as the starting material (FIG. 1). The present invention is therefore extremely advantageous in terms of the industrial production.

Many standard gene engineering techniques are utilized which are described in many standard experimental manuals, such as Molecular Cloning, 2nd edition, Cold Spring Harbor press (1989), *Saibo Kogaku Handbook* (Cell Engineering Handbook) edited by Toshio Kuroki et al., Yodosha (1992) and *Shin Idenshi Kogaku Handbook* (New Genetic Engineering Handbook), revised 3rd edition edited by Muramatsu et al., Yodosha (1999). Those skilled in the art can utilize these techniques with reference to these manuals and this specification.

1. Method for Producing L-Fuculose 1-1. Method Using a Protein Derived from Microorganism In the method for producing L-fuculose, L-fuculose is synthesized from L-fucitol using a protein derived from a microorganism. This protein has dehydrogenase activity, which enables synthesis of L-fuculose from L-fucitol. As described in detail in the following Examples, a protein is described which is able to synthesize L-fuculose from L-fucitol independently from the protein which synthesizes a ketohexose, other than L-fuculose, from l-fucitol in the microorganism. Therefore, it is possible to reduce or eliminate the byproduct production. Since the protein is derived from a microorganism, isolation and purification of the protein are easier than when purifying from plants and animals. Another advantage is that the protein will be compatible with a host when expressed on a large scale in the microorganism. Cultivation of a microorganism is easier than cultivation of plant or animal cells, and therefore it is easy to obtain a sufficient amount for industrial production.

As also described below, the amino acid and nucleotide sequence of this protein was determined based on isolationg of the protein from *Gluconobacter oxydans*.

The method for producing L-fuculose may reduce the cost since it uses the inexpensive starting material L-galactose, and is thus advantageous for industrial production because L-fucitol is easily obtainable from L-galactose. The method for obtaining L-fucitol from D-galactose is described in, for example, Carbohydrate research 270; 93-96 (1995).

The protein is derived or isolated from a microorganism, and has dehydrogenase activity, which allows it to synthesize L-fuculose from L-fucitol. The microorganisms which may be used include prokaryotic and eukaryotic microorganisms, and viruses, but exclude plant cells including algae. Examples of the microorganism may include those belonging to an *acetobacterium*. *Acetobacterium* may specifically include bacteria belonging to genera *Gluconobacter* and *Acetobacter*, and more specifically bacteria belonging to *Gluconobacter oxydans*, *Gluconobacter frateurii*, *Acetobacter turbidans*, *Gluconobacter roseus*, *Gluconobacter cerinus*, *Gluconobacter oxydans* subsp. *suboxydans*, *Acetobacter melanogenus*, *Gluconobacter xylinus* subsp. *xylinus*, *Acetobacter aurantius*, *Gluconobacter melanogenus*, *Gluconobacter scleroideus* and *Gluconobacter suboxydans*. More specifically, the protein may be obtained from the various bacterial strains described in Table 1.

In order to obtain a sufficient amount of such a microorganism, the microorganism may be cultured in an appropriate medium, depending on its type. The medium is not particularly limited as long as the microorganism can grow in the medium, and may be any of the standard media which typically contains sources of carbon, nitrogen, phosphorous, sulfur, inorganic ions, and further optionally containing organic nutrients.

Any carbon source which the microorganism can utilize may be used. Specifically, saccharides such as glucose, fructose, maltose, and amylose, alcohols such as sorbitol, ethanol, and glycerol, organic acids such as fumaric acid, citric acid, acetic acid, and propionic acid and salts thereof, hydrocarbons such as paraffin, and mixtures thereof, may be used.

As the nitrogen source, ammonium salts of inorganic acids such as ammonium sulfate and ammonium chloride, ammonium salts of organic acids such as ammonium fumarate and ammonium citrate, nitrate salts such as sodium nitrate and potassium nitrate, organic nitrogen compounds such as peptone, yeast extract, meat extract and corn steep liquor, or mixtures thereof, may be used.

Additionally, inorganic salts, trace metal salts and vitamins found in standard media may be used as the nutrient source, by appropriately mixing them.

Conditions for cultivation are not particularly limited. The cultivation may be performed under aerobic conditions, while appropriately controlling pH and temperature so that they range from pH 5 to 8 and from 15 to 40° C. for about 12 to 70 hours.

To purify the protein from the microorganism, standard methods used are those typically used in purification of proteins, e.g., ammonium sulfate salting-out, gel filtration, ion exchange chromatography, and hydrophobic chromatography. Microbial cell extracts are typically the starting material which is subjected to purification. If non-disrupted or non-lysed cells remain, further precipitated residues can be removed by subjecting the solubilized solution to re-centrifugation.

To synthesize L-fuculose from L-fucitol using the protein derived from the microorganism which has the dehydrogenase activity, L-fucitol may be placed in contact with the protein in a medium. For example, L-fucitol and the protein may be added to a buffer and allowed to react. The ranges of pH, temperature, reaction time, and amount of the added enzyme may be appropriately adjusted depending on the type of the protein. For instance, the pH is preferably 5 to 11, and more preferably 7 to 10. The temperature is preferably 20 to 50° C. and more preferably 25 to 40° C.

1-2. Method Using a Microorganism, a Culture Thereof, or a Treated Microbial Cell Product Thereof A method of using a microorganism, a culture of the microorganism, or a treated microbial cell product of the microorganism will now be described. Another embodiment for the method of synthesizing L-fuculose using the aforementioned protein is to use a microorganism which contains the aforementioned protein, a culture thereof, or a treated microbial cell product thereof. However, when the microorganism itself is used, the microorganism may also synthesize a ketohexose other than L-fuculose (hereinbelow referred to as a byproduct). Thus, when the microorganism itself is used, it is preferable to use a microorganism which does not produce the byproduct, or produces a small amount. That is, it is preferable to use a microorganism which satisfies at least two criteria: (i) the ability to synthesize L-fuculose from L-fucitol, and (ii) the ability to synthesize L-fuculose to such an extent that the amount of L-fuculose thus produced accounts for preferably 50% or more, more preferably 70% or more, and still more preferably 90% or more of total L-fucitol oxide generated by oxidizing L-fucitol.

The microorganism which satisfies both the aforementioned criteria may include *Gluconobacter xylinus* subsp. *xylinus* and *Gluconobacter oxydans*, more preferably *Gluconobacter xylinus* subsp. *xylinus* ATCC 53582 strain and ATCC 23767 strain, and *Gluconobacter oxydans* IFO 3189 strain, and still more preferably *Gluconobacter xylinus* subsp. *xylinus* ATCC 53582 strain. These microorganisms do not synthesize substantial amounts of ketohexoses other than L-fuculose, or if so, the amounts are very small.

Therefore, a preferable embodiment of the present invention is a method of using a non-genetically engineered microorganism which contains the protein having the dehydrogenase activity which results in synthesis of 1-fuculose from L-fucitol, wherein the microorganism does not have a substantial ability to synthesize ketohexoses, other than L-fuculose, from L-fucitol. The phrase "does not have a substantial ability" means that the amount of the ketohexose, other than L-fuculose, byproducts is not more than the detection limit under the conditions shown in Example 1. Specifically, the phrase "does not have a substantial ability" means that the amount of the non-L-fuculose ketohexose byproducts is about 1 mM or less.

A "genetically engineered microorganism" refers to a microorganism in which a gene has been artificially engineered using genetic engineering techniques, and does not include naturally occurring mutants. The phrase "non-genetically engineered microorganism" refers to microorganisms which are not genetically engineered.

The phrase "culture of the microorganism" means the culture obtained after culturing the microorganism. The culture of the microorganism may specifically contain microbial cells of the microorganism, the medium used for the cultivation of the microorganism, and/or a mixture of substances produced by the microorganism, and the supernatant thereof.

The phrase "treated microbial cell product" refers to the product obtained after some artificial manipulation of the microbial cells. The treated microbial cell product may contain, for example, disrupted microbial cells, lysed cells, and lyophilized cells. The treated microbial cell product may also be a crude protein collected by treating the microbial cell, or a purified protein. The purified protein may be a partially purified protein obtained by various purification methods, and an immobilized protein obtained by immobilizing the protein via covalent bonds, an absorption method, or an inclusion method.

As described above, the treated microbial cell product may contain matter that includes the content of the cells of the microorganism. Therefore, when the treated microbial cell product is used, proteins responsible for synthesizing the byproduct may be present. Thus, it is preferable to use a microorganism which is able to synthesize L-fuculose so that the total amount of L-fuculose accounts for 50% by weight or more of total L-fucitol oxide. When the protein which is able synthesize L-fuculose from L-fucitol is sufficiently purified from the microorganism and this purified protein is used, the microorganism may be a source of this protein. Thus, as already described above, the microorganism is not limited by whether the microorganism produces the byproduct or not.

Synthesis of L-fuculose using the microorganism may be conducted so that the protein which is able to synthesize L-fuculose may act upon the substrate L-fucitol. For example, the microorganism may be cultured and L-fucitol may be added to the culture. Synthesis with the treated microbial cell product may be performed by mixing the treated microbial cell product with L-fucitol so that the protein which is able to synthesize L-fuculose may act upon the substrate L-fucitol. That is, the reaction system may be constructed in the same manner as the reaction system that uses an enzyme or a bioactive substance.

1-3. A Method Using the Genetically Engineered Strain

As another embodiment of the present invention, there is provided a method for using a microorganism which contains the protein which is able to synthesize L-fuculose, but in which the gene encoding the protein which produces the byproduct has been knocked out. Even though the original microorganism produces the byproduct, knocking out of the gene which encodes the enzyme responsible for production of the byproduct may result in a microorganism which is suitable for the production of L-fuculose. Such a microorganism can efficiently produce L-fuculose with no substantial production of the byproduct.

"Gene knockout" refers to a procedure by which the gene encoding the target protein is modified so to reduce or eliminate the function of the intact protein. The "gene" refers to a molecule which encodes genetic information, and includes DNA, RNA, and polynucleotides such as hybrid molecules thereof or chimera molecules thereof. The gene knockout procedure includes introducing a mutation by deletion, substitution, insertion, and/or inversion so that the protein itself is modified, or inhibiting the expression of the protein by inhibiting transcription or translation.

The method for knocking out the gene is not particularly limited. To knock out the gene, for example, the gene may be mutated or the gene may be deleted. Inactivation of the gene may be performed by general methods such as mutagenesis by UV irradiation or treatment with N-methyl-N'-nitro-N-nitrosoguanidine, site-directed mutagenesis, homologous recombination, or insertion-deletion mutagenesis, often referred to as homologous recombination or "Red-driven integration" (Datsenk K. A. and Wanner B. L., Proc. Natl. Acad. Sci. USA, 97(12:6640-45, 2000).

For example, when the gene is knocked out by homologous recombination, a recombinant DNA construct is prepared which contains the the target gene, but a portion of the target gene has been deleted so to inactivate the expression and production of the dehydrogenase. A microorganism in which the chromosomal dehydrogenase gene has been deleted may be obtained by transforming the microorganism with the above-described DNA construct to cause recombination between the inactivated dehydrogenase gene and the chromosomal peptidase gene.

The protein which is able to synthesize a ketohexose other than L-fuculose from L-fucitol may also be subjected to a gene knockout procedure.

As another embodiment using the genetically engineered microorganism, there is provided a method for using the microorganism which is not able to substantially synthesize a ketohexose other than L-fuculose from L-fucitol, and wherein said microorganism is transformed so that is expresses the protein which has dehydrogenase activity which allows it to synthesize L-fuculose from L-fucitol. Even though the original microorganism does not have the protein which is able to synthesize L-fuculose, L-fuculose production can be obtained by by modifying the microorganism by introducing the gene which expresses L-fuculose. It is preferable to select a microorganism which is unable to produce the byproduct to facilitate efficient production of L-fuculose without unnecessary byproducts.

A microorganism which is not able to to substantially synthesize a ketohexose other than L-fuculose from L-fucitol may be chosen, whether the gene which encodes a protein which is able to synthesize a ketohexose has been knocked out, or whether the microorganism does not contain such an activity in its native state. Examples of the protein to be subjected to gene knockout may include the protein which is able to synthesize D-xylulose from D-arabitol.

The transformant may be produced in accordance with standard methods. For example, the transformant may be obtained as follows. A protein which is able to synthesize L-fucose is obtained and purified from the aforementioned microorganism, and its amino acid sequence is determined. The amino acid sequence may be determined using the Edman method (Edman, P., Acta Chem. Scand. 4, 227 (1950)). The amino acid sequence may also be determined using a sequencer (Applied Biosystems). The first 30 amino acid residues from the N terminus is determined, and this sequence is reverse translated to determine the nucleotide sequence of the DNA. Universal codons are employed for deducing the nucleotide sequence of the DNA.

Based on the deduced nucleotide sequence, a DNA molecule of about 30 base pairs is synthesized. The method for synthesizing the DNA molecule is disclosed in Tetrahedron Letters, 22, 1859 (1981). The DNA molecule may also be synthesized using a synthesizer supplied from Applied Biosystems. The DNA molecule may be utilized as a probe to isolate the full length DNA from a chromosomal gene library from the microorganism. The DNA molecule may also be utilized as a primer in PCR to amplify the.

The PCR method is described in White, T. J. et al., Trends Genet. 5, 185 (1989). The method for preparing chromosomal DNA and the method for isolating the object DNA molecule from the gene library using the DNA molecule as the probe are described in Molecular Cloning, 2nd edition, Cold Spring Harbor press (1989).

The method for determining the nucleotide sequence of the isolated DNA encoding the protein is described in A Practical Guide to Molecular Cloning, John Wiley & Sons, Inc. (1985). The nucleotide sequence may also be determined using a DNA sequencer (Applied Biosystems).

Subsequently, the preparation of the transformant which expresses the protein will be described. Numerous examples of producing useful proteins, such as enzymes and physiologically active substances, have been reported using recombinant DNA technology. Using recombinant DNA technology makes it possible to produce large amounts of a desired protein which is naturally present in trace amounts.

To prepare a transformant which expresses the protein, the DNA molecule isolated by the aforementioned method may be introduced into a host. That is, the isolated DNA molecule is incorporated into an expression vector so that it is able to be expressed, and this is introduced into the host cell.

When the protein is produced on a large scale using the recombinant gene technology, bacterial cells, actinomycetal cells, yeast cells, fungal cells, plant cells, and animal cells may be used as hosts. Generally, enteric bacteria, preferably Escherichia coli is suitable, because this bacteria is commonly used for producing proteins on a large scale. The method for producing the protein using transformed Escherichia coli will be described below.

Promoters which are conventionally used for the production of a xenogeneic protein in Escherichia coli may be used. Examples thereof may include potent promoters such as T7 promoter, lac promoter, trp promoter, trc promoter, and tac promoter, as well as $P_R$ promoter and $P_L$ promoter of lambda phage.

The promoter is ligated to the gene encoding the protein so to line up the reading frames of the codons. The ligation may be performed at appropriate restriction enzyme sites. Alternatively, a synthetic DNA of an appropriate sequence may be utilized.

In order to increase the amount of production, it is preferable in some cases to ligate a transcription termination sequence downstream of the gene. The terminator may include T7 terminator, fd phage terminator, T4 terminator, a terminator of a tetracycline resistant gene, and a terminator of Escherichia coli trpA gene.

The so-called multicopy-type vectors are preferable to introduce the gene into E. coli. Examples thereof may include plasmids which have a replication origin derived from ColE1, e.g., pUC based plasmids, pBR322 based plasmids, or derivatives thereof. As used herein, the term "derivative" means the plasmid which is modified by substitution, deletion, insertion, addition and/or inversion. The modification may be by mutagenesis with a mutagen or UV irradiation or natural mutation. More specifically, as the vector, for example, pUC19, pUC18, pBR322, pHSG299, pHSG298, pHSG399, pHSG398, RSF1010, pMW119, pMW118, pMW219, and pMW218 may be used. Additionally, vectors such as phage DNA or transposon DNA may be used.

In order to select the transformant, it is preferable that the vector has a marker such as an ampicillin resistant gene. Expression vectors with the potent promoter are commercially available [pUC series (Takara Shuzo Co., Ltd.), pPROK series (Clonetech), pKK233-2 (Clonetech)].

A DNA fragment obtained by ligating the promoter, the gene encoding a peptide synthesizing enzyme, or a fusion protein of the peptide synthesizing enzyme and another protein, and the terminator is ligated to the vector DNA to yield a recombinant DNA.

Escherichia coli is then transformed with this recombinant DNA, and cultured to express and produce the protein. As the host to be transformed, the strain which is usually used for the expression of the xenogeneic gene may be used. Escherichia coli JM109 strain which is one of Escherichia coli K12 subspecies is preferable. The method for transforming and the method for selecting the transformant are described in Molecular Cloning, 2nd edition, Cold Spring Harbor press (1989).

Media such as M9-casamino acid medium and LB medium usually used for culturing Escherichia coli may be used for the cultivation. The cultivation and production induction conditions are selected depending on the marker and promoter used, and the host microorganism.

The protein may be collected by the methods previously described.

1-4. Method of Production Under Reaction Conditions Where Production of Byproduct is Inhibited Even though the microorganism synthesizes a byproduct other than L-fuculose, by oxidizing L-fucitol under conditions which inhibit the production of the byproduct, it is possible to produce L-fuculose in an industrially efficient manner. In order to inhibit the production of the byproduct, for example, the pH may be adjusted, or an inhibitor which selectively inhibits the enzyme which controls the production of the byproduct may be added.

The pH level which inhibits the production of the byproduct varies depending on the type of the microorganism. Thus, a preliminary experiment can be performed depending on the type of the microorganism. The preliminary experiment may be performed under the conditions shown in the following Example, and those skilled in the art may set the pH condition to inhibit the byproduct based on the following example.

The inhibitor for the production of the byproduct may be added to the reaction system. It is desirable that the inhibitor does not inhibit the production of L-fuculose from L-fucitol at all, but any inhibitor can be used as long as L-fuculose is sufficiently produced relative to the production of the byproduct. Examples of the inhibitor include a bivalent ion chelator and preferably EDTA (ethylenediamine tetraacetate).

1-5. NAD Supply System

As shown in the following Example, it has been shown that the protein which is able to synthesize L-fuculose from L-fucitol is NAD-dependent. In this case, NAD is required in a molar amount equivalent to the amount of L-fuculose to be produced. However, NAD is expensive, and considering the industrial production scale, the addition of an equivalent amount of NAD is disadvantageous in terms of production cost. Based on these findings, a method for producing L-fuculose is provided in which L-fuculose is synthesized from L-fucitol in the presence of the protein which is able to reproduce NAD from NADH that has been converted from NAD upon synthesis of L-fuculose. By constituting the reaction system in which NAD is supplied, it is possible to produce L-fuculose continuously and sufficiently, and the method is extremely advantageous in terms of industrial production.

The microorganism which is able to synthesize L-fuculose from L-fucitol may also have the protein which can produce NAD from NADH in some cases. In such a case, the microorganism or the treated microbial cell product may be added to the reaction system. If the protein which is able to produce NAD from NADH is not present in the reaction system, such a protein may be added. Many dehydrogenases are able to produce NAD from NADH, and the reduction ability of these dehydrogenases may be utilized. In this case, NADH functions as a coenzyme, and thus, it is necessary to add additional substrate for the reaction. Other than these dehydrogenases, oxidase and peroxidase which oxidize NADH to NAD may be used. The substrate required is oxygen for NADH oxidase or hydrogen peroxide for peroxidase. For the former, the substrate is easily supplied into the reaction solution by stirring the reaction solution. For the latter, hydrogen peroxide is very inexpensive and therefore advantageous in terms of cost. Oxidase and peroxidase are publicly known and commercially available.

2. Method for Producing L-Fucose

The method for producing L-fucose of the present invention includes a step of synthesizing L-fuculose, and a step of synthesizing L-fucose from L-fuculose. The aforementioned steps may be performed in separate reaction systems or in a combined reaction system. L-Fucitol is the raw material for producing L-fuculose, and is easily obtained from D-galactose, which is inexpensive. Therefore, the method for producing L-fucose of the present invention is an industrially excellent method which is easy and simple and can reduce the cost.

The step of synthesizing L-fuculose is described above in the section "1. Method for producing L-fuculose". In the method for producing L-fucose of the present invention, the various embodiments as mentioned above may be employed.

The method for synthesizing L-fucose from L-fuculose is shown in, for example International Publication WO02/06506. Preferably, L-fucose isomerase is utilized to obtain L-fucose. Examples of L-fucose isomerase include those whose sequences have been registered in the database in, for example, the National Center for Biotechnology Information.

When using L-fucose isomerase, a microorganism may be transformed to express L-fucose isomerase, and the produced L-fucose isomerase may be then isolated for use. Alternatively, the microorganism transformed to express L-fucose isomerase or the treated microbial cell product of the microorganism may be used. The transformant may be made in the same way as the technique described in the aforementioned section "1-3. Method using genetically engineered strain".

As a preferable embodiment of the method for producing L-fucose of the present invention, a co-expressing transformant is made and used to synthesize L-fucose from L-fucitol in one reaction system. In this embodiment, L-fucose is synthesized from L-fucitol in the presence of at least one of the following: 1) a microorganism transformed to express a microorganism-derived protein which is not able to substantially synthesize a ketohexose other than L-fuculose from L-fucitol and which has dehydrogenase activity which results in synthesis of L-fuculose from L-fucitol, and a protein which is able to synthesize L-fucose from L-fuculose; and 2) a treated microbial cell product of the microorganism. By preparing such a co-expressing transformant and using this as described above, it is possible to simplify the process, which is highly advantageous for the industrial production.

3. Protein Having Dehydrogenase Activity Which Results in the Synthesis of L-Fuculose from L-Fucitol and a Polynucleotide Encoding the Same The following are examples of the protein which is not able to substantially synthesize a ketohexose other than L-fuculose from L-fucitol and which has dehydrogenase activity which result in synthesis of L-fuculose from L-fucitol:

(A) a protein having the amino acid sequence of SEQ ID NO:16; or (B) a protein having the amino acid sequence of SEQ ID NO: 16, but which includes one or several amino acid mutations selected from the group consisting of substitution, deletion, insertion, addition, and inversion, and which has dehydrogenase activity which results in the synthesis of L-fuculose from L-fucitol.

The aforementioned protein (A) may be isolated from *Gluconobacter oxydans* IFO 3255. The protein of the present invention includes a protein which is substantially identical to (A), such as the protein described in (B). The substantially identical protein may also be isolated from the bacterial strains described in Table 1. However, the protein of the present invention specified by the aforementioned sequence is not limited by the source from which the protein has been isolated. As described in detail below, the aforementioned protein may be produced by preparing a transformed microorganism based on the aforementioned sequence using gene recombinant technology.

As used herein, "several" varies depending on a position and a type of the amino acid in the three dimensional structure of the protein, and wherein such change or changes do not have a signficant negative effect on the three dimensional structure and the activity of the protein. Specifically, "several" ranges from 1 to 100, preferably from 1 to 50, more preferably from 1 to 30, and still more preferably from 1 to 10. However, in the case of the protein (B), it is desirable that the protein (B) retains the enzyme activity at about a half or more, preferably 80% or more, more preferably 90% or more, and particularly preferably 95% or more of the protein (A) under the conditions of 30° C. and pH 9.5.

The amino acid mutations described in (B) may be obtained by modifying the nucleotide sequence of the gene encoding the protein of the present invention using, e.g., site-directed mutagenesis so that the amino acid at specific position is substituted, deleted, inserted, or added. The polypeptide having the modified nucleotide sequence may be obtained by conventionally known mutagenesis treatments, including in vitro treatment of the DNA encoding (A) with hydroxylamine and treating Escherichia coli having the DNA encoding (A) with ultraviolet ray irradiation or a mutagen such as N-methyl-N'-nitro-N-nitrosoguanidine (NTG) or nitrous acid, which are typically used in artificial mutagenesis.

The aforementioned mutations may also include naturally occurring mutations, such as differences depending on species and bacterial strains of the microorganisms. The DNA molecule encoding the protein substantially identical to the protein described in SEQ ID NO:16 may be obtained by expressing the DNA molecule having the aforementioned mutations in the appropriate cell and examining the present enzyme activity of an expressed product.

A polynucleotide encoding the protein for the method for producing L-fuculose may include a polynucleotide encoding the amino acid sequence described in SEQ ID NO:16. There can be a plurality of nucleotide sequences which define one amino acid sequence due to codon degeneracy. That is, the polynucleotide of the present invention includes the polynucleotides having the nucleotide sequences encoding the following proteins:

(A) a protein having the amino acid sequence of SEQ ID NO:16; or (B) a protein having the amino acid sequence of SEQ ID NO. 16, including one or several amino acid mutations selected from the group consisting of substitution, deletion, insertion, addition, and inversion, and which has dehydrogenase activity which results in synthesis of L-fuculose from L-fucitol.

The nucleotide sequence encoding the amino acid sequence described in SEQ ID NO:16 may include the nucleotide sequence of SEQ ID NO:15. The polynucleotide which is substantially identical to the polynucleotide of SEQ ID NO:15 may be obtained by isolating a polynucleotide which hybridizes with the nucleotide sequence which is complementary to the nucleotide sequence of SEQ ID NO:15, or a probe prepared from the nucleotide sequence under stringent conditions and encodes the protein which has dehydrogenase activity which results in synthesis of L-fuculose from L-fucitol.

That is, the preferable polynucleotides of the present invention may include the following:

(a) a polynucleotide having the nucleotide sequence of SEQ ID NO:15; and (b) a polynucleotide which hybridizes with the nucleotide sequence which is complementary to the nucleotide sequence of SEQ ID NO:15 under stringent conditions and encodes the protein which has dehydrogenase activity which results in synthesis of L-fuculose from L-fucitol.

The probe may be prepared based on the nucleotide sequence of SEQ ID NO:15 by a conventional method. Using the probe, the polynucleotide which hybridizes with this probe may be isolated by conventional method. For example, the DNA probe may be prepared by amplifying the nucleotide sequence cloned into the plasmid or the phage vector, cutting out the desired nucleotide sequence using restriction enzymes, and extracting it. Restriction sites may be chosen depending on the DNA.

As used herein, the "stringent conditions" refers to when a so-called specific hybrid is formed and a non-specific hybrid is not formed. Examples thereof may include when a pair of DNA sequences with high homology, e.g., DNA sequences having the homology of 50% or more, more preferably 80% or more, still more preferably 90% or more, and particularly preferably 95% or more, hybridize to each other, whereas DNAs with lower homology do not hybridize, and with washing conditions typical of an ordinary Southern hybridization, i.e., hybridization at salt concentrations equivalent to 1×SSC and 0.1% SDS at 60° C., and preferably 0.1×SSC and 0.1% SDS at 60° C. The genes which hybridize under these conditions may include those in which a stop codon is present, or an active center has been lost due to mutation. However, these features may be easily removed by ligating the gene to the commercially available vector, expressing it in the appropriate host, and measuring the enzyme activity of the expressed product by the methods described in the following Example.

In the polynucleotide encoding the aforementioned protein (B), and the polynucleotide (b), it is desirable that the polynucleotide encodes the protein which retains the dehydrogenase activity which results in synthesis of L-fuculose from L-fucitol at about a half or more, more preferably 80% or more, and still more preferably 90% as compared to the protein having the amino acid sequence encoded by the nucleotide sequence of SEQ ID NO:1 under the conditions of 30° C. and pH 9.5.

The DNA having the nucleotide sequence of SEQ ID NO:15 may be obtained from the chromosomal DNA or the DNA library of Gluconobacter oxydans IFO 3255 or IFO 3171 by PCR (see Polymerase chain reaction, White, T. J. et al; Trends Genet., 5, 185(1989)) or hybridization. Primers used for PCR may be designed based on an internal amino acid sequence determined based on the purified protein having the peptide-synthesizing activity. The full length coding region of the present protein may be amplified using primers corresponding to the 5' non-translated region and 3' non-translated region in PCR.

The primer may be synthesized using a DNA synthesizer model 380B (Applied Biosystems) and a phosphoamidite method (see Tetrahedron Letters (1981), 22, 1859) in accordance with conventional methods. The PCR reaction may be performed by using Gene Amp PCR System 9600 (PERKIN ELMER) and TaKaRa LA PCR in vitro Cloning Kit (Takara Bio Inc.) in accordance with the instructions supplied by the manufacturer.

The methods for producing the recombinant polynucleotide using an expression vector, and the transformant using the aforementioned polynucleotide are described in the section "1-3. Method using genetically engineered strain".

4. Protein having NADH oxidase activity and polynucleotide encoding the same

As described above, one preferable embodiment of the method for producing L-fuculose may be when NADH oxidase is added to the reaction system. The following are specific examples of NADH oxidase used herein:

(C) a protein having an amino acid sequence of SEQ ID NO:18; and (D) a protein having an amino acid sequence of SEQ ID NO. 18, including one or several amino acid mutations selected from the group consisting of substitutions, deletions, insertions, additions and inversions, and which has NADH oxidase activity.

The aforementioned protein (C) may be isolated from *Gluconobacter oxydans* IFO 3255. The protein of the present invention includes a protein which is substantially identical to (C), such as the protein described in (D). Furthermore, the substantially identical protein may be isolated from the bacterial strains described in Table 1.

The definition of "several", the method for introducing the mutation, and the types of the mutations are described in "3. Protein having dehydrogenase activity to synthesize L-fuculose from L-fucitol and polynucleotide encoding the same". However, the proteins of the present invention specified by the aforementioned sequences are not limited by the source from which they have been isolated.

The polynucleotide encoding the protein for the method for producing L-fuculose of the present invention includes that shown in SEQ ID NO: 18. There can be a plurality of nucleotide sequences which define one amino acid sequence because of codon degeneracy. That is, the polynucleotide of the present invention includes polynucleotides having the nucleotide sequences encoding the following proteins:

(C) a protein having an amino acid sequence of SEQ ID NO:18; or (D) a protein having an amino acid sequence of SEQ ID NO: 18, but including one or several amino acid mutations selected from the group consisting of substitution, deletion, insertion, addition, and inversion, and which has NADH dehydrogenase activity.

An example of the nucleotide sequence encoding the amino acid sequence described in SEQ ID NO:18 is shown in SEQ ID NO:17. That is, the preferable polynucleotides of the present invention may include the following polynucleotides:

(c) a polynucleotide having the nucleotide sequence of SEQ ID NO:17; and (d) a polynucleotide which hybridizes with the the nucleotide sequence which is complementary to the nucleotide sequence of SEQ ID NO: 17 under stringent conditions and encodes the protein which has NADH dehydrogenase activity.

The "stringent conditions", the method for producing the probes and the primers, and the method for isolating DNA using the same are described in "3. Protein having dehydrogenase activity to synthesize L-fuculose from L-fucitol and polynucleotide encoding the same".

When the polynucleotide encoding NADH oxidase is incorporated into a recombinant polynucleotide such as an expression vector, the aforementioned polynucleotide alone may be incorporated, or it may be incorporated with a polynucleotide encoding the protein which has dehydrogenase activity which results in synthesis of L-fuculose from L-fucitol. Furthermore, the protein with NADH oxidase activity and the protein with dehydrogenase activity may be expressed in separate transformants. Alternatively, they may be co-expressed in the same microorganism. However, when NADH oxidase is used with another dehydrogenase in the NAD reproduction system, the dehydrogenase, the NADH oxidase, and NAD must be present in the same reaction system. When the enzymatic reaction using the enzyme or when the treated microbial cell product is used, the dehydrogenase and the NADH oxidase may be produced in separate hosts. However, when the untreated microbial cells are used as a catalyst, it is desirable to co-express both enzymes in the same host.

EXAMPLES

The present invention will be described in more detail hereinbelow with reference to the following non-limiting Examples.

Example 1

A Microorganism which Oxidizes L-Fucitol to Synthesize L-Fuculose

Each of the *acetobacterium* strains was cultured on YPG agar medium (10 g/l glycerol, 0.3 g/l yeast extract, 0.3 g/l peptone, 20 g/l agar, pH 6.5) at 30° C. for 18 to 66 hours, and one platinum loopful of each culture was then seeded into 0.5 mL of a liquid medium containing 10 g/l (61 mM) L-fucitol, 10 g/l glycerol, 3 g/l yeast extract, 3 g/l peptone, and 20 g/l $CaCO_3$ pH 6.5 that had been sterilized by autoclaving at 120° C. for 20 minutes. Cultivation was then performed with shaking at 30° C. for 42 hours. A 96-well microplate having 2 ml volume per well was used for the cultivation. Microbial cells were then removed from the medium by centrifugation. The supernatant was analyzed by high performance liquid chromatography (HPLC) to determine the concentration of L-fuculose. Analysis conditions for HPLC were as follows:

column: Sugar SC1011 supplied from Shodex, diameter: 10 mm, length: 300 mm column temperature: 75° C.

mobile phase: 50 ppm Ca-EDTA in $H_2O$ flow rate: 1.2 ml/minute detection: differential refractive index (R1) detector L-fucose, L-fucitol, and L-fuculose eluted at about 7.6, 11.9 and 13.6 minutes, respectively. Commercially available preparations of L-fucitol and L-fucose supplied from Sigma were used as standards to determine their eluted positions and their concentrations for comparison. For L-fuculose, no commercially available product was available for use as a standard. Thus, a substance produced from L-fucose using L-fucose isomerase, which will be described below in detail, was used as L-fuculose. In this case, the sum of the integral value of the peak (peak area value) of remaining fucose and the integral value of the peak of produced L-fuculose on a chart was scarcely changed and was constant regardless of before and after reacting with L-fucose isomerase. Thus, the peak area value of L-fuculose per unit concentration was regarded to be the same as that of L-fucose, and the concentration of L-fuculose was calculated accordingly in the preparation. The detection limit is about 1 mM in the analyses in the Examples. In many analyses, an unidentified peak appeared which seemed to be a transformed product derived from L-fucitol because of its peak area size. This peak was observed at about 8.0 minutes. The concentration of this unidentified substance (referred to hereinbelow as BP), was calculated using the peak area value of L-fucose per unit concentration, i.e., in the same manner as the calculation of the L-fuculose concentration. Analysis results are shown in Table 1. Note that "*Gluconobacter*" and "*Acetobacter*" are sometimes abbreviated as "G." and "A.", respectively.

TABLE 1

MICROORGANISMS WHICH PRODUCE
L-FUCULOSE FROM L-FUCITOL (1)

| Strain | L-FUCULOSE (mM) | BP (mM) | L-FUCITOL (mM) | L-FUCULOSE/ (L-FUCULOSE + BP) (wt %) |
|---|---|---|---|---|
| *Gluconobacter oxydans* IFO 3171 | 14.4 | 25.5 | 6.9 | 36.1 |
| *G. frateurii* IFO3264 | 14.1 | 27.3 | 16.2 | 34.1 |
| *G. oxydans* ATCC621 | 12.3 | 17.3 | 20.0 | 41.6 |
| *Acetobacter melanogenus* IFO3190 | 12.2 | 17.3 | 20.5 | 41.4 |
| *G. frateurii* IFO3268 | 11.6 | 18.7 | 29.0 | 38.3 |
| *G. roseus* AJ2840 | 10.3 | 13.1 | 22.9 | 44.0 |
| *G. cerinus* IFO3262 | 10.2 | 14.5 | 26.2 | 41.3 |
| *G. oxydans* IFO3255 | 9.1 | 14.5 | 36.4 | 38.6 |
| *G. roseus* AJ2845 | 9.0 | 17.0 | 23.9 | 34.6 |
| *G. oxydans* subsp. *suboxydans* AJ2866 | 7.8 | 21.9 | 23.9 | 26.3 |
| *G. roseus* AJ2843 | 7.7 | 13.8 | 28.1 | 35.8 |
| *G. oxydans* IFO3294 | 7.6 | 15.5 | 28.0 | 32.9 |
| *G. cerinus* IFO3276 | 6.9 | 11.6 | 37.3 | 37.3 |
| *G. suboxydans* AJ2849 | 6.3 | 15.4 | 26.5 | 29.0 |
| *A. melanogenus* AJ2867 | 5.8 | 10.5 | 36.0 | 35.6 |
| *G. cerinus* IFO3267 | 5.5 | 10.2 | 39.4 | 35.0 |
| *G. frateurii* IFO3254 | 4.9 | 8.9 | 46.2 | 35.5 |
| *A. turbidans* AJ2908 | 4.0 | 7.3 | 42.9 | 35.4 |
| *G. suboxydans* AJ2846 | 3.9 | 10.2 | 31.4 | 27.7 |
| *G. xylinus* subsp. *xylinus* ATCC53582 | 3.6 | 0.0 | 54.8 | 100.0 |
| *A. aurantius* IFO3246 | 3.1 | 7.5 | 40.1 | 29.2 |
| *G. melanogenus* AJ2876 | 2.9 | 7.9 | 39.9 | 26.9 |
| *G. oxydans* IFO14819 | 2.4 | 8.9 | 49.0 | 21.2 |
| *G. scleroideus* AJ2838 | 1.4 | 2.5 | 45.3 | 35.9 |
| *G. suboxydans* AJ2841 | 1.3 | 3.6 | 46.2 | 26.5 |
| *G. xylinus* subsp. *xylinus* ATCC23767 | 1.1 | 1.0 | 52.2 | 52.4 |
| *G. oxydans* IFO 3189 | 1.0 | 0.1 | 54.1 | 90.9 |

* The microorganisms which produced 1 mM or more of L-fuculose under the conditions in Example 1 are shown.

Of the aforementioned microorganisms, those having an ATCC number have been deposited with the American Type Culture Collection (P.O. Box 1549 Manassas, Va. 20110, the United States of America), and can be ordered by their reference number. Those having an IFO number were deposited with the Institute for Fermentation Osaka (17-85 Juso-honmachi 2-chome, Yodogawa-ku, Osaka, Japan). However, they were transferred to NITE Biological Resource Center (NBRC) in the Department of Biotechnology, National Institute of Technology and Evaluation (NITE) on Jun. 30, 2002, and the microorganisms are thus available from NBRC.

Example 2

A Microorganism which Oxidizes L-Fucitol to Synthesize L-Fuculose

In order to induce the expression of an enzyme which oxidizes L-fucitol using dulcitol, the structure of which is similar to that of L-fucitol, each of the *acetobacterium* strains was cultured on YP-dulcitol agar medium (10 g/l dulcitol, 0.3 g/l yeast extract, 0.3 g/l peptone, 20 g/l agar, pH 6.5) at 30° C. for 18 to 66 hours, and one loopful of each strain was then seeded into 0.5 mL of the liquid medium containing 10 g/l L-fucitol, 3 g/l yeast extract and 3 g/l peptone pH 6.5 that had been sterilized by autoclaving at 120° C. for 20 minutes. Cultivation was then performed with shaking at 30° C. for 42 hours. This cultured medium was analyzed in the same way as in Example 1. The analysis results are shown in Table 2.

TABLE 2

MICROORGANISMS WHICH PRODUCE
L-FUCULOSE FROM L-FUCITOL (2)

| Strain | L-FUCULOSE (mM) | BP (mM) | L-FUCITOL (mM) | L-FUCULOSE/ (L-FUCULOSE + BP) (wt %) |
|---|---|---|---|---|
| *G. xylinus* subsp. *xylinus* ATCC53582 | 7.8 | 0.0 | 48.5 | 100.0 |
| *Gluconobacter roseus* AJ2840 | 3.8 | 6.9 | 49.9 | 35.5 |
| *G. oxydans* subsup *suboxydans* AJ2866 | 3.6 | 10.4 | 34.5 | 25.7 |

TABLE 2-continued

MICROORGANISMS WHICH PRODUCE
L-FUCULOSE FROM L-FUCITOL (2)

| Strain | L-FUCULOSE (mM) | BP (mM) | L-FUCITOL (mM) | L-FUCULOSE/ (L-FUCULOSE + BP) (wt %) |
|---|---|---|---|---|
| G. oxydans IFO3255 | 1.6 | 6.2 | 41.7 | 20.5 |
| G. oxydans IFO 3189 | 1.6 | 0.1 | 57.6 | 94.1 |

\* The microorganisms which produced 1 mM or more of L-fuculose under the conditions in Example 2 are shown.

In both Examples 1 and 2, a plurality of *acetobacterium* belonging to genus *Gluconobacter* or *Acetobacter* which produce L-fuculose using L-fucitol have been identified, although many of them also simultaneously produced BP. Only one microorganism produced only L-fuculose, strain *Gluconobacter xylinus* subsp. *xylinus* ATCC 53582. *Gluconobacter xylinus* subsp. *xylinus* ATCC 23767 and *Gluconobacter oxydans* IFO 3189, in addition to *Gluconobacter xylinus* subsp. *xylinus* ATCC 53582, were found to produce 50% or more L-fuculose based on the combined total amount of L-fuculose and BP.

Example 3

Identification of Substance Assumed to be L-Fuculose by HPLC Analysis

In order to identify the substance which was assumed to be L-fuculose by HPLC analysis, a bioassay using L-fucose isomerase was conducted.

L-Fucose isomerase (EC 5.3.1.3., referred to hereinbelow as "FucI") catalyzes isomerization between L-fuculose and L-fucose. If the compound assumed to be L-fuculose in Examples 1 and 2 is L-fuculose, this compound should convert to L-fucose in the presence of FucI. Commercially available L-fucose (e.g., Sigma) is available. Utilizing this product as a standard, it is possible to perform HPLC analysis or a colorimetric quantification using L-fucose dehydrogenase described in Patent No. 3132913 Publication.

FucI was isolated from *E. coli* K12 strain. This enzyme has been registered with accession number AAC75844 in the database of National Center for Biotechnology Information. To express this enzyme in large amounts in *E. coli*, and also to insert a histidine tag at the N terminus to facilitate purification, pQE30 (QIAGEN) was used as the expression vector for FucI. In order to insert a FucI gene (fucI) between the SphI and HindIII sites in the multicloning sites of pQE30, PCR primers 1 and 2, shown as SEQ ID NO:1 and SEQ ID NO:2, respectively, were prepared. PCR was performed using a template of genomic DNA from *E. coli* W3100 that had been obtained by the standard method to yield a fragment with a length of about 1.8 kbp. This fragment and the pQE30 vector were digested with SphI and HindIII and purified, and then ligated to produce plasmid pQE30FucIH6 (hereinbelow referred to as FucIH6). The expressed protein contained the His-tag sequence at the N terminus. The entire nucleotide sequence and the deduced amino acid sequence of the expressed fucIH6 are shown in SEQ ID NOS:3 and 4, respectively. *E. coli* JM109 strain was transformed with this plasmid, resulting in FucIH6-expressing strain *E. coli* JM109/pQE30FucIH6.

This bacterial strain was cultured at 37° C. in LB medium, and the expression of fucIH6 was induced by adding IPTG to a final concentration of 1 mM when the absorbance at 600 nm was about 0.4. The cultivation was continued for 2 hours after this induction. Then, the microbial cells were collected by centrifuging the medium, and were washed with 50 mM Tris-HCl (pH 8.0). The washed microbial cells were disrupted by sonication at 200W for 10 minutes. The disrupted product was then centrifuged to obtain a supernatant which was used as a crude enzyme solution. Imidazole to a final concentration of 10 mM and NaCl to a final concentration of 0.3 M were added to this crude enzyme solution, which was then mixed with 1 ml of Ni-NTA resin (QIAGEN) which had been equilibrated with 50 mM Tris-HCl (pH 8.0), 10 mM imidazole, and 0.3 M NaCl (hereinafter, "buffer W"). The mixture was shaken overnight, whereby the protein with the His-tag sequence was bound to the resin. After shaking, the resin was collected by centrifugation. Resin was further washed several times with buffer W, and transferred to a column. Subsequently, the absorbed protein was eluted by adding 0.2 M imidazole. The eluted fraction thus obtained was dialyzed against 50 mM Tris-HCl (pH 8.0), 1 mM 2-mercaptoethanol, and 0.1 mM $MnCl_2$, and further concentrated through a membrane as needed, for subsequent experimentation. The resulting enzyme solution was subjected to SDS-PAGE. As a result, an almost single band with a molecular weight of about 67 kDa, which seemed to be FucIH6, was observed.

The bacterial strains listed in Table 3 were used for the conversion of L-fucitol by *acetobacterium*. One platinum loopful of each refreshed *acetobacterium* strain was seeded into 0.5 mL of a liquid medium of 10 g/l L-fucitol, 10 g/l glycerol, 3 g/l yeast extract, and 3 g/l peptone at pH 6.5, and cultured with shaking at 30° C. for 42 hours. At that time, the medium from which glycerol had been removed was used for only the cultivation of *Gluconobacter xylinus* subsp. *xylinus* ATCC 53582 strain. The 96-well microplate with 2 ml per well was used for the cultivation.

The resulting cultured liquid was centrifuged to remove the microbial cells, and an equivalent volume of 0.2 M potassium phosphate buffer (pH 7.0) containing 2 mM 2-mercaptoethanol, 0.2 mM $MnCl_2$ and 0.4 mg/ml FucIH6 (each final concentration is a half thereof) were added to react at 37° C. for 2 hours. At that time, an experimental group without FucIH6 was made and used as the control.

After completion of the reaction, the reaction solution was analyzed by HPLC. When L-fucose and BP were simultaneously produced, it was difficult to strictly quantify them by HPLC because their elution positions were close. Therefore, L-fucose was also quantified by the calorimetric method using L-fucose dehydrogenase. The quantification was performed by adding L-fucose dehydrogenase (Kikkoman Corporation, NADP-dependent) to the final concentration of 0.2 mg/ml, NADP to the final concentration of 1 mM in 0.1 M glycine-NaOH buffer (pH 9.5) to the appropriately diluted FucIH6 reaction solution to react at 37° C. for 30 minutes. The changes in the absorbance at 340 nm induced by NADPH production were measured. The results are shown in Table 3.

TABLE 3

Conversion by FucIH6 of compound produced by conversion of L-fucitol

| Strain | COLORIMETRIC METHOD L-FUCOSE (mM) | HPLC | | | |
|---|---|---|---|---|---|
| | | L-FUCOSE (mM) | L-FUCULOSE (mM) | BP (mM) | L-FUCITOL (mM) |
| (A) With FucI | | | | | |
| Gluconobacter oxydans IFO 3171 | 7.86 | 6.5 | 0 | 17.7 | 34.1 |
| G. xylinus subsp. xylinus ATCC53582 | 7.52 | 7 | 1.6 | 0 | 51.4 |
| G. oxydans IFO3255 | 7.51 | 6.4 | 0 | 18.5 | 32.8 |
| G. roseus AJ2845 | 7.44 | 6.2 | 0 | 19.6 | 33.5 |
| G. roseus AJ2843 | 7.06 | 6 | 0 | 17.3 | 35.1 |
| G. oxydans ATCC621 | 6.94 | 5.8 | 0 | 25.6 | 29.1 |
| G. frateurii IFO3268 | 6.72 | 5.2 | 0 | 17.3 | 38.3 |
| Acetobacter turbidans AJ2908 | 5.41 | 3.8 | 0 | 9.6 | 44.5 |
| G. oxydans subsp. suboxydans AJ2866 | 5.32 | 3.8 | 0 | 18.6 | 37.2 |
| G. cerinus IFO3267 | 5.27 | 3.5 | 0 | 15.6 | 41.7 |
| G. melanogenus AJ2876 | 2.45 | 1.3 | 0 | 9 | 51.8 |
| (B) Without FucI | | | | | |
| Gluconobacter oxydans IFO 3171 | 0.56 | 0 | 8 | 15.1 | 33.4 |
| G. xylinus subsp. xylinus ATCC53582 | 0.59 | 0.1 | 8.2 | 0 | 51.6 |
| G. oxydans IFO3255 | 0.75 | 0 | 7.3 | 16 | 35.5 |
| G. roseus AJ2845 | 0.76 | 0 | 7.2 | 16.1 | 34.2 |
| G. roseus AJ2843 | 0.41 | 0 | 7.4 | 15.8 | 37.5 |
| G. oxydans ATCC621 | 0.58 | 0 | 7 | 23.7 | 29.1 |
| G. frateurii IFO3268 | 0.41 | 0 | 6.6 | 15.3 | 38.9 |
| Acetobacter turbidans AJ2908 | 0.02 | 0 | 4.4 | 7.8 | 45.8 |
| G. oxydans subsp. suboxydans AJ2866 | 0.49 | 0 | 4.8 | 17.6 | 38.1 |
| G. cerinus IFO3267 | 0.07 | 0 | 4.3 | 12.9 | 45 |
| G. melanogenus AJ2876 | 0.67 | 0 | 1.5 | 6.5 | 52.7 |

As a result, the substance assumed to be L-fuculose by the HPLC analysis was converted into L-fucose by the reaction with FucIH6. Thus, by this result, the substance was identified to be L-fuculose as predicted. At the same time, these results indicate that it is possible to synthesize L-fucose by contacting L-fucose isomerase with L-fuculose synthesized from L-fucitol by the *acetobacterium*. The quantitative capability of L-fucose seemed to be precarious because of the poor separation of BP from L-fucose on HPLC. However, similar results were obtained when quantifying L-fucose using the calorimetric method using L-fucose dehydrogenase, and it was thus confirmed that L-fucose can be easily quantified by HPLC. Meanwhile, BP, which had been believed to be a byproduct, was not converted by the addition of FucIH6, and was identified to be a compound other than L-fuculose or L-fucose since it was not a substrate of FucIH6.

Example 4

Conversion of L-Fucitol by *Acetobacterium* Expressing FucI

In Example 3, it was demonstrated that L-fuculose can be produced from L-fucitol by *acetobacterium*, and L-fuculose can be converted into L-fucose using FucI. As to production of L-fucose using L-fucitol, it is possible to separately produce L-fuculose from L-fucitol and L-fucose from L-fuculose as in Example 3. However, it is advantageous to simultaneously perform these reactions so to simplify the process. In particular, if *acetobacterium* itself could convert L-fuculose to L-fucose, it would become possible to advantageously produce L-fucose from L-fucitol using a single bacterial strain.

Therefore, *G. oxydans* IFO 3171 strain, a typical strain which is able to synthesize L-fuculose from L-fucitol, was transformed to construct a strain which expresses FucI isolated from *E. coli*. As an example of the expression system of the specific protein in the *acetobacterium*, it is possible to utilize the method of using the plasmid pSA19 described in Biosci. Biotechnol. Biochem., 67: 584-591 (2003). A gene fragment encoding the full length FucI derived from *E. coli* was obtained by PCR as in Example 3, and this was inserted into the multicloning sites of pSA19 to yield a FucI expression plasmid, named pSA19FucI. However, unlike Example 3, no His-tag was added to FucI, so the wild-type FucI was expressed. Primers having the sequences of SEQ ID NOs:5 and 6 were used in PCR to clone from *E. coli*. This means that the predicted amino acid sequence of the expressed FucI and the fucI gene inserted into pSA19FucI are identical to the wild-type enzyme. *G. oxydans* IFO 3171 strain was transformed with pSA19FucI using the method of the aforementioned reference.

Figure 2:
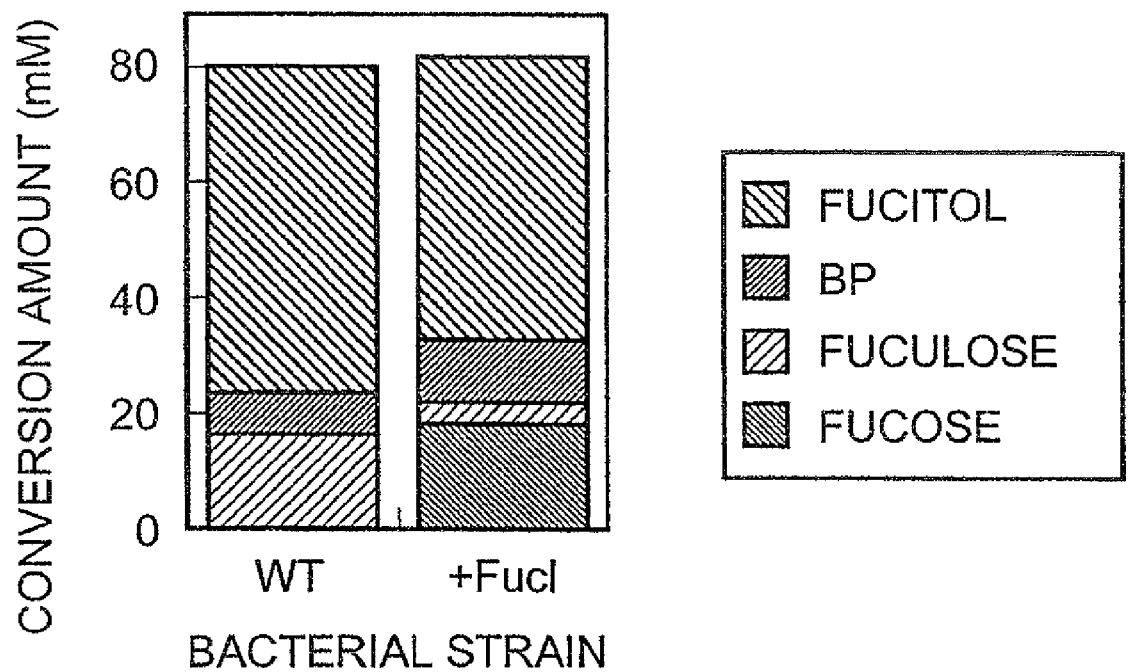
FIG. 2 shows the amount of L-fucitol converted by FucI-expressing *acetobacterium*.

After refreshing *G. oxydans* IF03171/pSA19FucI on YPG agar medium, one platinum loopful thereof was seeded into 3 ml of the liquid medium containing 10 g/l L-fucitol, 10 g/l glycerol, 3 g/l yeast extract, and 3 g/l peptone pH 6.5, and cultured with shaking at 30° C. for 18 hours. Microbial cells were collected by centrifuging 1 ml of the medium, and then washed with 0.1 M Tris-HCl buffer (pH 8.0). The washed microbial cells were resuspended in 0.5 ml of the same buffer. L-fucitol was added to a final concentration of 10 g/l, and the mixture was reacted at 30° C. for 90 hours in the 96-well microplate having 2 ml volume per well. After the reaction, the microbial cells were removed from the medium by centrifugation, and the supernatant was subjected to HPLC analysis. The combined concentrations of the product and the remaining substrate exceeded the substrate concentration at the onset of the conversion reaction. This appeared to be due to the evaporation of the reaction solution during conversion. The analysis results are shown in FIG. 2. In FIG. 2, WT and +FucI represent the wild-type strain and the FucI-expressing strain, respectively.

As a result, the effect as anticipated was observed. That is, L-fuculose which was synthesized by the conversion with the wild-type strain was further converted into L-fucose in the FucI-expressing strain. This enabled production of L-fucose from L-fucitol with the *acetobacterium* strain alone.

Example 5

Reduction of Byproduct (BP) During Production of L-Fuculose from L-Fucitol by Controlling the pH of the Reaction To reduce problematic BP during the production of L-fuculose from L-fucitol, the reaction pH was examined.

Figure 3:
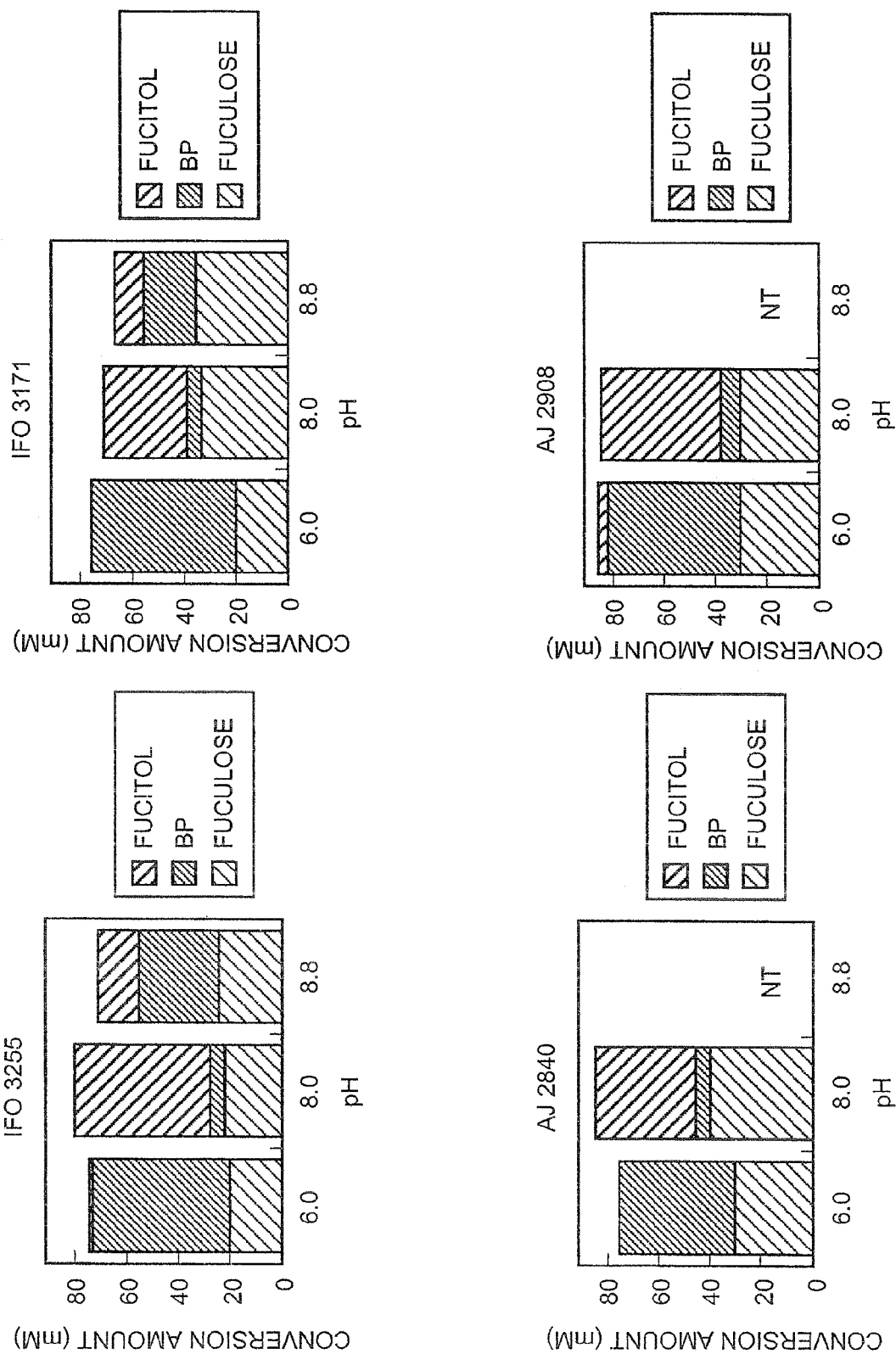
FIG. 3 shows the amounts of byproducts (BP) which are produced during the production of L-fuculose from L-fucitol under different pH conditions.

G. oxydans IFO 3255 strain, G. oxydans IFO 3171 strain, G. roseus AJ 2840 strain, and A. turbidans AJ 2908 strain were used in the experiments. One platinum loopful of the bacterial strain that had been refreshed on YPG agar medium was seeded into a sterilized liquid medium containing 10 g/l glycerol, 10 g/l L-fucitol, 0.3 g/l yeast extract, 0.3 g/l peptone, and 20 g/l $CaCO_3$ pH 6.5, and cultured in a test tube at 30° C. for 42 hours. Subsequently, 1 ml of the cultured medium was dispensed. The microbial cells were collected by centrifugation, and then washed with 0.1M potassium phosphate buffer (pH 6.0) or 0.1 M Tris-HCl buffer (pH 8.0) or 0.1 M glycine NaOH buffer (pH 8.8). The washed microbial cells were resuspended in 0.5 ml of each buffer. L-fucitol was added to a final concentration of 10 g/l, and the mixture was reacted at 30° C. for 66 hours in the 96-well microplate having 2 ml volume per well. After the reaction, the microbial cells were removed by centrifugation, and the supernatant was subjected to HPLC analysis. The results are shown in FIG. 3. In the figure, NT indicates that the experiment was not performed.

As a result, with any of the bacterial strains, the amount of L-fuculose produced increased as the reaction pH was increased, whereas the amount of BP produced was minimal at pH 8.

Example 6

Reduction of Byproduct (BP) During Production of L-Fuculose from L-Fucitol by the Addition of EDTA For the purpose of reducing problematic BP during production of L-fuculose from L-fucitol, EDTA was added to the reaction solution, and its effect was examined.

Figure 4:
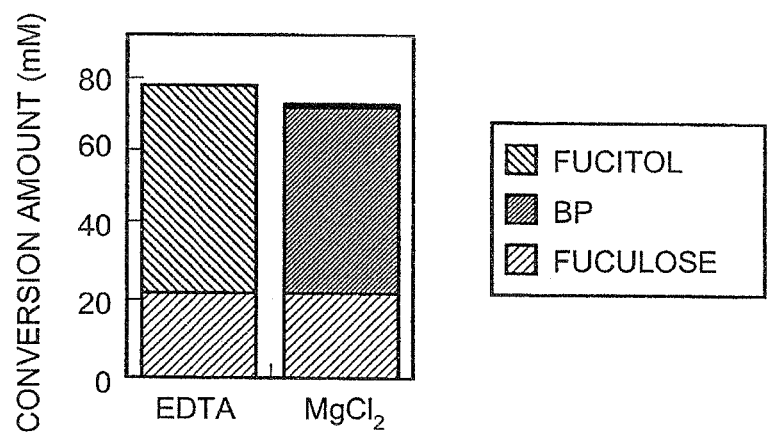
FIG. 4 shows the amounts of byproducts (BP) which are produced when L-fuculose is produced from L-fucitol in the presence of EDTA.

G. oxydans IFO 3255 strain was used in the experiments. The cultured liquid was obtained in the same way as in Example 5 (except that $CaCO_3$ was not added to the cultivation medium), and 1 ml of the cultured liquid was dispensed. The microbial cells were collected by centrifugation and washed with 0.1 M potassium phosphate buffer (pH 6.0). The washed microbial cells were resuspended in 0.5 ml of the same buffer. L-fucitol to a final concentration of 10 g/l and EDTA or $MgCl_2$ to a final concentration of 10 mM were added thereto, and the mixture was reacted at 30° C. for 90 hours in the 96-well microplate having 2 ml volume per well. After the reaction, the microbial cells were removed by centrifugation, and the supernatant was subjected to HPLC analysis. The results are shown in FIG. 4.

As a result, the addition of EDTA did not affect the amount of L-fuculose produced, whereas the addition of EDTA remarkably reduced the amount of BP produced to almost zero.

Example 7

Reduction of Byproduct (BP) During Production of L-Fuculose from L-Fucitol by Knocking Out the sldA Gene It was demonstrated that the methods shown in Examples 5 and 6 are effective for controlling the amount of BP production when L-fuculose is produced using L-fucitol.

From the results of Examples 5 and 6, it is likely that the enzyme responsible for the synthesis of L-fuculose from L-fucitol and the enzyme responsible for the synthesis of BP are present independently. Therefore, it would most likely be effective to delete the enzyme which controls the synthesis of BP.

The conversion of L-fucitol using *acetobacterium* strains is documented in the literature. For example, see the Journal of American Chemical Society 72: 4934-4937 (1950) and Canadian Journal of Chemistry 45: 741-744 (1967). These references disclose that L-fucitol is oxidized by a *acetobacterium* strain which consequently produces 1-deoxy-D-glycero-3-hexulose. In the work of the current inventors, L-fucitol and the unidentified substance (BP) were detected as oxides of L-fucitol produced by the *acetobacterium* strain. Thus, it is the unidentified substance (BP) is likely to be 1-deoxy-D-glycero-3-hexulose described in the literature. The possibility that the enzymes producing these substances are independently present has been discussed in the literature. However, their independent existence has not been proven and the enzymes which control the respective reactions have not been identified.

Biosci. Biotechnol. Biochem. 65: 2755-2762 (2001) reports that D-arabitol dehydrogenase which is present on the *acetobacterium* membrane controls the oxidation of many sugar compounds. In this reference, the oxidation of L-fucitol is not described. However, because of its broad substrate specificity, the enzyme possibly catalyzes the oxidation of L-fucitol to produce either L-fuculose or BP which seemed to be 1-deoxy-D-glycero-3-hexulose. In the latter case, it was predicted that the production of BP could be essentially eliminated by knocking out this D-arabitol dehydrogenase. Based on this hypothesis, an attempt was made to produce a bacterial strain in which the D-arabitol dehydrogenase was defective, as described below.

D-Arabitol dehydrogenase present on the cell membrane has also been referred to as glycerol dehydrogenase or D-sorbitol dehydrogenase because of the broadness of its substrate specificity. In the literature, for example in JP H8-242850 A, this enzyme has been referred to as D-sorbitol dehydrogenase, and its gene has been cloned and its nucleotide sequence has been determined. In accordance with information, the gene encoding a D-arabitol dehydrogenase catalytic subunit is hereinbelow designated as sldA, and the protein encoded by sldA is hereinbelow designated as SldA. For producing a SldA-defected strain, a DNA fragment which lacks an internal partial sequence of sldA was prepared. This fragment was introduced into an *acetobacterium* to induce homologous recombination of sldA on the chromosomal DNA. To detect the mutant strain, a kanamycin resistant gene Kmr was introduced with the defective sldA fragment. Thus, the mutant strain was easily detected by growing on a medium containing kanamycin.

First, to prepare a fragment containing a homologous recombination region, a fragment containing an internal partial sequence of sldA was obtained by PCR using the primers shown in SEQ ID NOS:7 and 8 (having KpnI and PstI recognition sites, respectively). As the template, genomic DNA prepared from *Gluconobacter oxydans* IFO 3255 strain whose sldA nucleotide sequence had been reported was used. In addition, when genomic DNA prepared from *Gluconobacter oxydans* IFO 3171 strain was used, the fragment having the anticipated length was also amplified. This result was due to the high homology of the sequence. With each fragment, analysis by treating with the restriction enzymes revealed that one recognition site each of BamHI and BalII were present. Thus, the sldA sequence which lies between these sites was removed, and instead, the Kmr gene was inserted in this site. The Kmr gene was obtained by PCR using the template plasmid pHSG298 (Takara Bio Inc.) bearing Kmr, and the primers shown in SEQ ID NOS:9 and 10.

The fragment obtained by PCR with the template of the *acetobacterium* genomic DNA was digested with KpnI and PstI and purified, and then subcloned into pUC18 (Takara Bio Inc.) that had been digested with KpnI and PstI and purified. *E. coli* JM 109 strain was transformed with this plasmid, and cultured. Subsequently, the plasmid was extracted, purified, and digested with BamHI and BglII and purified. The fragment prepared by PCR with pHSG298 containing Kmr was ligated thereto to yield a novel plasmid. *E. coli* JM109 strain was transformed with this plasmid, and cultured. Subsequently, the plasmid was extracted, purified, further digested with KpnI and PstI, and purified to yield a sldA fragment with the Kmr gene inserted therein. Each of these fragments derived from IFO 3255 strain and IFO 3171 strain was introduced into IFO 3255 strain and IFO 3171 strain, respectively, by electroporation (electrode interval: 0.5 mm, 14.0 kV/cm). The strains capable of growing on a kanamycin-containing plate were selected to yield *G. oxydans* IFO 3255 sldA:Kmr strain and *G. oxydans* IFO 3171 sldA:Kmr strain.

Figure 5:
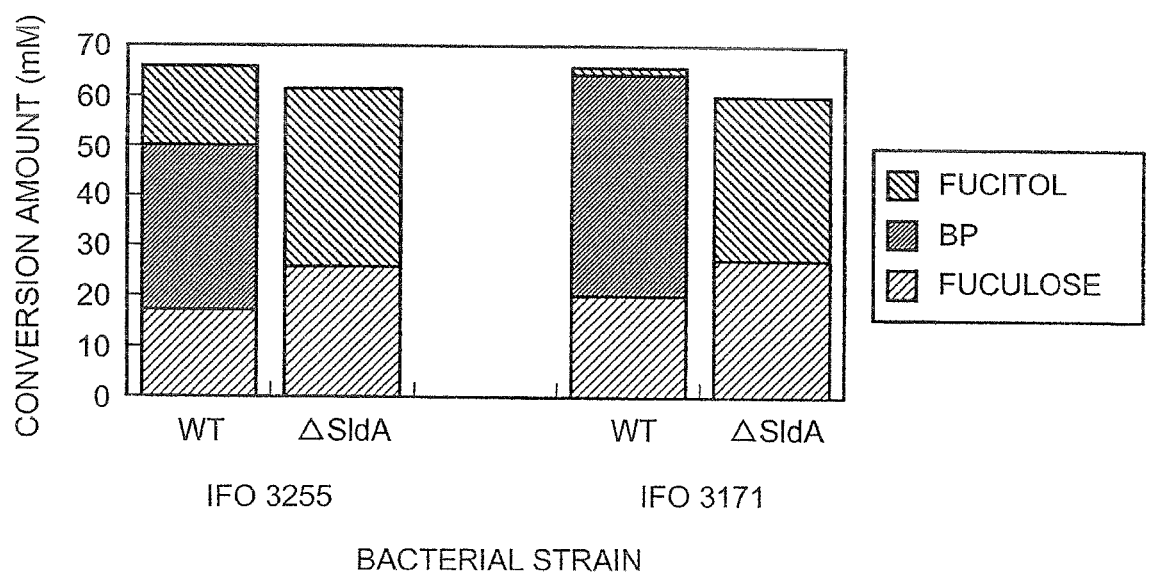
FIG. 5 shows the amounts of byproducts (BP) which are produced when L-fuculose is produced from L-fucitol using a knock-out sidA gene.

Using these mutant strains, L-fucitol conversion was performed. 1 mL of the cultured medium obtained as in Example 6 was dispensed. The microbial cells were collected by centrifugation and washed with 0.1 M glycine NaOH buffer (pH 8.8). Then, the cells were resuspended in 0.5 ml of the same buffer. L-fucitol to a final concentration of 10 g/l and $MgCl_2$ to a final concentration of 10 mM were added thereto, and the mixture was reacted at 30° C. for 66 hours in the 96-well microplate having 2 ml volume per well. After the reaction, the microbial cells were removed by centrifugation, and the supernatant was subjected to HPLC analysis. The results are shown in FIG. 5. In FIG. 5, WT and ΔSldA indicate the wild-type strain and the sldA gene-knockout strain, respectively.

As a result, these mutant strains produced L-fuculose but no BP at all. This result demonstrates that the synthesis of BP from L-fucitol is catalyzed by SldA, and that the enzyme which synthesizes L-fuculose from L-fucitol is present independently of SldA. Using the SldA-defect strain does not require control of the pH and/or addition of EDTA, and is effective to produce 1-fuculose from L-fucitol without producing the byproduct from L-fucitol.

Example 8

The Enzyme Activity which Synthesizes L-Fuculose from L-Fucitol

Since it was demonstrated in Example 7 that an enzyme other than SldA which synthesizes L-fuculose from L-fucitol was present, a search for this enzyme activity was conducted.

A candidate of the enzyme of interest seemed to be NAD (P)-dependent dehydrogenase because synthesis of L-fuculose from L-fucitol involves oxidation. It has been reported that D-arabitol dehydrogenase derived from red algae *Galdieria sulphuraria* catalyzes the oxidation of L-fucitol in an NAD-dependent manner (Planta 202: 487-493 (2003)). However, this activity is weak, and no product has been identified. Thus, whether L-fuculose is formed or a product other than L-fuculose is produced as in the case of SldA has not been examined.

First, it was examined whether the *acetobacterium* strain has the activity to oxidize L-fucitol in an NAD(P)-dependent manner. After refreshing sldA:Kmr mutant strain derived from *G. oxydans* on YPG agar medium, one platinum loopful thereof was seeded into the liquid medium containing 10 μl glycerol, 0.3 g/l yeast extract, and 0.3 g/l peptone pH 6.5, and cultured in a test tube at 30° C. for 24 hours. Subsequently, 1 ml of the medium was added to 50 ml of the same liquid medium, and cultured at 30° C. for 18 hours using a 500 ml Sakaguchi flask. The microbial cells were collected by centrifuging this medium, washed with 9 g/l of NaCl, and sonicated with 200 W for 10 minutes to yield the disrupted microbial cells. These cells were further centrifuged at 15,000 g for 15 minutes to yield the supernatant, which was then used as a cell-free extract. Using this cell-free extract as an enzyme source, L-fucitol and NAD(P) at final concentrations of 10 mM and 1 mM, respectively, were reacted in the presence of 0.1 M glycine NaOH buffer (pH 8.8) or 0.1 M potassium phosphate buffer (pH 6.0) at 30° C., to measure the L-fucitol oxdation activity. The experiment was also performed without L-fucitol as the control. The oxidation activity was quantified by the increase in absorbance at 340 nm caused by the production of NAD(P)H. One activity unit was defined as the activity to oxidize 1 μmol of the substrate in one minute. The results are shown in Table 4.

As a result, L-fucitol dehydrogenase using NAD as the coenzyme was detected. This activity was higher at pH 8.8 than at pH 6.0. Although this product has not been identified as L-fuculose, the results correspond with that observed in Example 5, i.e., the amount of L-fuculose produced increased at a higher pH. Thus, this activity might be involved in the synthesis of L-fuculose.

TABLE 4

NAD(P)-dependent L-fucitol oxidation activity in cell free extract of *G. oxydans* IFO 3255 sldA:Kmr mutant strain

| | | Dehydrogenase activity ($\times 10^{-3}$ U/mg) | | | |
|---|---|---|---|---|---|
| | Coenzyme | NAD | | NADP | |
| SUBSTRATE | pH | 6.0 | 8.8 | 6.0 | 8.8 |
| $H_2O$ | | 0.0 | 0.0 | 0.0 | 0.0 |
| L-FUCITOL | | 3.1 | 18.4 | 0.0 | 1.9 |

Example 9

L-Fucitol Conversion Using an *Acetobacterium* Cell-Free Extract

Since the L-fucitol oxidation activity was present in the *acetobacterium* cell-free extract, L-fucitol conversion was was attempted.

As the enzyme source, the cell-free extract obtained in Example 8 was added to 0, 0.8, 1.6, and 4.0 mg/ml as the total protein final concentrations to the reaction solution, and left to stand with 10 g/l L-fucitol, 0.1M glycine NaOH (pH 8.8), 0.03 mM FAD, 1 mg/ml BSA, and 2 mM NAD at 30° C. for 90 hours. Subsequently, the product was subjected to HPLC analysis. In order to identify NAD dependency of the L-fucitol conversion, a control without added NAD, and a control with added NADH oxidase for the purpose of supplying NAD were used. NADH oxidase caused synthesis of NAD and hydrogen peroxide from NADH and oxygen (Nacalai Tesque, derived from *Bacillus liqueniformis*). NADH produced during the reaction would most likely be reconverted into NAD by NADH oxidase, and the NAD would then be reused for the oxidation of L-fucitol. NADH oxidase was added to a final concentration of 0.1 U/ml. Catalase to a final concentration of 10 U/ml was also added for the purpose of consuming the hydrogen peroxide. The results are shown in Table 5.

The conversion of L-fucitol by the *acetobacterium* cell-free extract was observed in any group with added NAD depending on the amount of added NAD. However, the conversion was not observed at all in the group without added NAD. Thus, it was confirmed that this conversion proceeds in a NAD-dependent manner, which supports the result in Example 8. Therefore, the activity which is involved in this conversion was attributed to the dehydrogenase which was identified in Example 8. The products of this conversion were L-fuculose and L-fucose, and BP was not observed at all. Therefore, it was confirmed that the L-fucitol oxidation enzyme present in this cell-free extract was an L-fuculose-forming enzyme. Only a trace amount of L-fucose was observed. Thus, enzymes such as L-fucose isomerase which synthesizes L-fucose from L-fuculose or L-fucitol oxidase which directly synthesizes L-fucose from L-fucitol was present in the cell-free extract. Furthermore, the amount of L-fuculose which was produced exceeded the amount of added NAD regardless of the presence of NAD oxidase. This result implies that the activity to reconvert NADH that had been produced from NAD by the oxidation reaction into NAD was also present in the cell free extract. This activity appears to be, for example, NADH oxidase activity.

TABLE 5

L-fucitol conversion experiments using cell free extract of *G. oxydans* IFO 3255 sldA:Kmr mutant strain

| Extract (mg/ml) | NAD (mM) | NADH oxidase, Catalase | L-FUCULOSE (mM) | L-FUCOSE (mM) | BP (mM) | L-FUCITOL (mM) |
|---|---|---|---|---|---|---|
| 0.0 | 2 | + | 0.0 | 0.0 | 0.0 | 61.6 |
| 0.8 | 2 | + | 6.1 | 0.4 | 0.0 | 35.9 |
| 1.6 | 2 | + | 8.0 | 2.2 | 0.0 | 29.4 |
| 4.0 | 2 | + | 13.3 | 2.6 | 0.0 | 21.9 |
| 0.0 | 2 | − | 0.0 | 0.0 | 0.0 | 55.8 |
| 0.8 | 2 | − | 2.8 | 0.0 | 0.0 | 36.2 |
| 1.6 | 2 | − | 6.6 | 1.7 | 0.0 | 29.3 |
| 4.0 | 2 | − | 12.6 | 1.9 | 0.0 | 22.5 |
| 0.8 | 0 | + | 0.0 | 0.0 | 0.0 | 53.0 |

Example 10

NADH Oxidase Activity in the *Acetobacterium* Cell-Free Extract

Since it was suggested in Example 9 that NADH oxidase activity (NADH oxidation) was present in the *acetobacterium* cell-free extract, the detection of this enzyme was attempted.

As the enzyme source, the cell-free extract obtained in Example 8 was reacted with NADH and FAD at final concentrations of 0.2 mM and +0.03 mM, respectively, in the presence of 0.1M Tris-HCl buffer (pH 8.0) or 0.1M glycine NaOH buffer (pH 8.8) at 30° C., to measure the NADH oxidation activity. The group without the extract was used as a control. The oxidation activity was quantified by measuring the decrease in absorbance at 340 nm caused by the conversion of NADH to NAD. One activity unit was defined as the activity to oxidize 1 μmol of NADH in one minute at 30° C. The results are shown in Table 6.

As a result, NADH oxidation activity was detected in both buffers at pH 8.0 and 8.8. At pH 8.0, the addition of FAD facilitated this activity. The activity of many known NADH oxidases has been reported to be FAD-dependent. Thus, the NADH oxidation activity present in the extract used in this experiment might be due to a similar NADH oxidase.

TABLE 6

NADH oxidase activity in cell free extract of *G. oxydans* IFO 3255 sldA:Kmr mutant strain

| Extract | pH | FAD (mM) | ACTIVITY ($\times 10^{-3}$ U/mg) |
|---|---|---|---|
| + | 8.0 | 0 | 3.6 |
| + | 8.0 | 0.03 | 26.3 |
| − | 8.0 | 0.03 | 0.0 |
| + | 8.0 | 0.03 | 22.5 |
| − | 8.0 | 0.03 | 0.0 |

Example 11

Determination of the Enzyme Source and the Cultivation Conditions for Producing the Enzyme To isolate and purify L-fuculose-producing L-fucitol dehydrogenase (FcDH), a bacterial strain as a potential source and its cultivation conditions were studied.

Bacterial strain: *Gluconobacter oxydans* IFO 3255 or IFO 3171 strain

Medium: 10 g/l carbon source, 5 g/l yeast extract, 5 g/l peptone (pH 6.5)

carbon source: glycerol, D-mannitol, D-arabitol, xylitol

Cultivation temperature: 30° C.

Cultivation time period: 20 hours or 66 hours

Methods:

The bacterial strain was refreshed by culturing on YPG medium (3 g/l peptone, 3 g/l yeast extract, 1 g/l glycerol, pH 6.5) containing 20 g/l agar at 30° C. for two nights. These refreshed microbial cells were inoculated into a test tube containing 3 ml of autoclaved medium, and cultured with shaking at 30° C. for 24 or 66 hours. After the cultivation, the microbial cells were collected by centrifuging 3 ml of the cultured liquid, washed with 25 mM Tris-HCl buffer (pH 8.0), and resuspended in 0.3 ml of the same buffer. This was then subjected to sonication to disrupt the microbial cells, and then centrifuged at 200,000 g for 30 minutes to yield the supernatant. This was used as a sample to measure enzyme activity.

The enzyme activity of FcDH was measured by appropriately adding the enzyme solution to 0.2 M Glycine NaOH (pH 9.5), 1 mM $MgCl_2$, 10 mM L-fucitol, and 1 mM NAD, and reacting the mixture at 30° C. The activity was quantified by monitoring the change in absorbance at 340 nm to detect the production of NADH from NAD caused by oxidation. The measurement was started when NAD was added. The change in absorbance in the first minute was taken as the initial rate, and the activity was calculated therefrom. The group without L-fucitol was used as a blank. As to the FcDH activity, the activity to oxidize 1 μmol of L-fucitol in one minute at 30° C. was defined as one unit (U). Calculation was performed with the absorbance coefficient of NADH $e_{340}=0.63$ $mM^{-1}cm^{-1}$. The measurement was performed consecutively three times. Their mean value was taken and is shown in the figure with the standard deviation.

Results: The measurement results are shown in Table 7. Using both the FcDH specific activity per unit protein weight and the activity quantity obtained from the unit amount of the cultured liquid as indicators, G. oxydans IFO 3255 was used as the FcDH-producing bacterial strain in the following medium: 10 g/l D-mannitol, 5 g/l yeast extract, 5 g/l peptone (pH 6.5), for 24 hours.

the microbial cells. Subsequently, the supernatant (crude extract) was obtained by centrifuging at 200,000 g for 30 minutes. From approximately 3L of the cultured medium, 934 mg of the protein was yielded in the crude extract.

Subsequently, a fraction of this crude extract was obtained by fractionation with 30% to 60% saturated ammonium sulfate. The fraction was dialyzed against the buffer (50 mM Tris-HCl, pH 8.0, 1.2 M $(NH_4)_2SO_4$, 1 mM $MnCl_2$) overnight. The sample thus obtained was applied to Phenyl Sepharose HP 26/10 (Amersham Biosciences) that had been equilibrated with the same buffer. The protein which absorbed onto the carrier was eluted by decreasing the $(NH_4)_2SO_4$ concentration in the buffer from 1.2 M to 0 M. The FcDH activity was detected in the fraction having a $(NH_4)_2SO_4$ concentration of about 0.2 M. The fraction containing the FcDH activity was collected, concentrated, dialyzed against 50 mM potassium phosphate buffer (pH 6.0), and applied to Q-Sepharose 16/10 (Amersham Biosciences) that had been equilibrated with the same buffer. The protein which absorbed onto the carrier was eluted by increasing the NaCl concentration in the buffer from 0 M to 0.5 M. The FcDH activity was detected in the fraction having a NaCl concen-

TABLE 7

| BACTERIAL STRAIN | CARBON SOURCE | CULTIVATION TIME PERIOD (h) | PROTEIN (mg/ml) | FcDH SPECIFIC ACTIVITY (mU/ml) | (mU/ml) |
|---|---|---|---|---|---|
| G. oxydans IFO 3255 | GLYCEROL | 24 | 7.8 | 6.1 | 46.9 |
| G. oxydans IFO 3255 | GLYCEROL | 66 | 6.6 | 4.2 | 28.0 |
| G. oxydans IFO 3255 | D-MANNITOL | 24 | 4.1 | 18.7 | 77.5 |
| G. oxydans IFO 3255 | D-MANNITOL | 66 | 2.8 | 16.7 | 46.6 |
| G. oxydans IFO 3255 | D-MANNITOL | 24 | 5.1 | 17.6 | 89.6 |
| G. oxydans IFO 3255 | XYLITOL | 66 | 5.0 | 10.5 | 52.4 |
| G. oxydans IFO 3255 | XYLITOL | 24 | 7.2 | 13.9 | 100.2 |
| G. oxydans IFO 3255 | GLYCEROL | 66 | 3.8 | 9.4 | 35.9 |
| G. oxydans IFO 3171 | GLYCEROL | 24 | 5.4 | 5.7 | 31.1 |
| G. oxydans IFO 3171 | D-MANNITOL | 66 | 5.0 | 0.4 | 2.0 |
| G. oxydans IFO 3171 | D-MANNITOL | 24 | 7.6 | 2.7 | 20.4 |
| G. oxydans IFO 3171 | D-MANNITOL | 66 | 7.5 | 1.9 | 14.0 |
| G. oxydans IFO 3171 | D-ARABITOL | 24 | 9.2 | 1.8 | 16.0 |
| G. oxydans IFO 3171 | XYLITOL | 66 | 6.6 | 0.9 | 5.8 |
| G. oxydans IFO 3171 | XYLITOL | 24 | 7.3 | 4.7 | 34.3 |
| G. oxydans IFO 3171 | XYLITOL | 66 | 8.4 | 0.5 | 4.2 |

Example 12

Purification of FcDH

Figure 6:
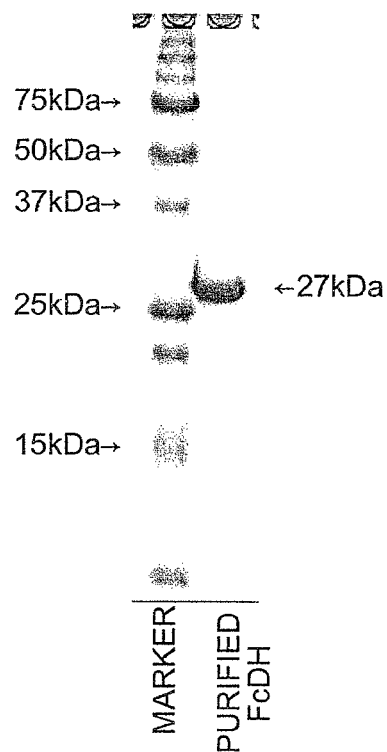
FIG. 6 shows an SDS-PAGE profile of purified FcDH.

The stored G. oxydans IFO 3255 strain was refreshed by culturing in the YPG agar medium at 30° C. for two nights. These refreshed microbial cells were inoculated into the test tube containing 3 ml of autoclaved medium, and cultured with shaking at 30° C. for 18 hours. This was seeded at 1% (v/v) in the 500 ml Sakaguchi flask containing 100 ml of the same autoclaved medium, and cultured at 30° C. for 24 hours. After the cultivation, the microbial cells were collected by centrifugation, washed with 25 mM Tris-HCl buffer (pH 8.0), and suspended in the same buffer at ⅕ the volume of the cultured medium. This was subjected to sonication to disrupt tration of about 0.4 M. The fraction containing the FcDH activity was collected, concentrated, and then applied onto Superdex 200 16/60 (Amersham Biosciences) that had been equilibrated with 50 mM potassium phosphate buffer (pH 6.0). As a result, FcDH eluted at a position at which the molecular weight was estimated as 102 kDa. The fraction containing the FcDH activity was collected, and concentrated. Its purity was then examined on SDS-PAGE. As a result, FcDH was observed as a single band whose molecular weight was estimated to be about 27 kDa (FIG. 6). By this series of purification steps, the specific activity of FcDH was increased 520 times from 0.015 U/mg in the crude extract to 7.8 U/mg. The amount of purified FcDH thus obtained was 0.60 mg, and the recovery of the activity was 34% (Table 8).

TABLE 8

| STEP | PROTEIN (mg/ml) | ACTIVITY (U) | RECOVERY RATE (%) | SPECIFIC ACTIVITY (U/mg) | PURIFICATION (-fold) |
|---|---|---|---|---|---|
| CRUDE EXTRACT | 934 | 14 | 100 | 0.015 | 1.0 |
| AMMONIUM SULFATE DIALYSIS | 535 | 11 | 79 | 0.020 | 1.4 |
| CHROMATOGRAPHY (Phenyl Sepharose) | 64 | 7.1 | 51 | 0.11 | 7.4 |
| CHROMATOGRAPHY (Q-Sepharose) | 1.1 | 7.0 | 50 | 6.4 | 427 |
| CHROMATOGRAPHY (Superdex) | 0.60 | 4.7 | 34 | 7.8 | 520 |

Example 13

Purification of NADH Oxidase (Hereinafter "NOX")

The stored G. oxydans IFO 3255 strain was refreshed by culturing in the YPG agar medium at 30° C. for two nights. These refreshed microbial cells were inoculated into the test tube containing 3 ml of autoclaved medium, and cultured with shaking at 30° C. for 18 hours. This was seeded at 1% (v/v) in a 500 ml Sakaguchi flask containing 100 ml of the same autoclaved medium, and cultured at 30° C. for 24 hours. After the cultivation, the microbial cells were collected by centrifugation, washed with 25 mM Tris-HCl (pH 8.0), and suspended in the same buffer at ⅟25 the volume of the cultured medium. This was subjected to sonication to disrupt the microbial cells. Subsequently, the supernatant (crude extract) was obtained by centrifuging at 200,000 g for 30 minutes. From approximately 4 L of the cultured medium, 1253 mg of the protein was obtained in the crude extract.

Figure 7:
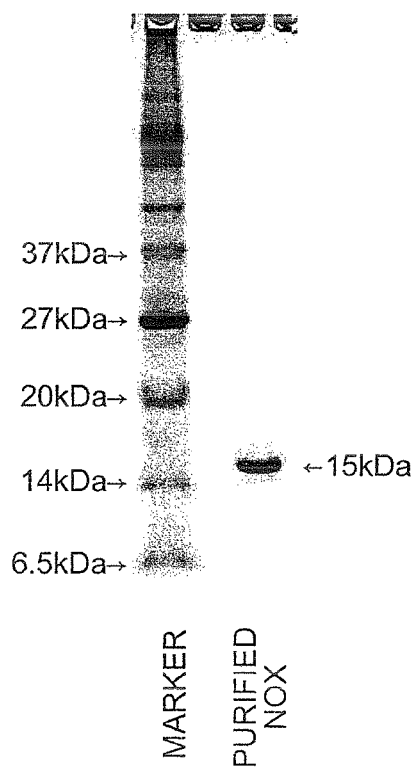
FIG. 7 shows an SDS-PAGE profile of purified NOX.

Subsequently, a fraction of this crude extract was obtained by fractionation with 30% to 60% saturated ammonium sulfate. The fraction was dialyzed against the buffer (50 mM potassium phosphate, pH 6.0, 1 mM DTT, 0.5 mM EDTA) overnight. The sample thus obtained was applied onto Q-Sepharose 26/10 that had been equilibrated with the same buffer. The protein which absorbed onto the carrier was eluted by increasing the NaCl concentration in the buffer from 0 M to 0.5 M. The NOX activity was detected in the fraction having a NaCl concentration of about 0.25 M. The fraction containing the NOX activity was collected, concentrated, dialyzed against the following buffer (50 mM Tris-HCl, pH 8.0, 0.6 M $(NH_4)_2SO_4$), and applied onto Phenyl Sepharose 16/10 that had been equilibrated with the same buffer. The protein which absorbed onto the carrier was eluted by decreasing the $(NH_4)_2SO_4$ concentration in the buffer from 0.6 M to 0 M. The NOX activity was detected in the fraction having a $(NH_4)_2SO_4$ $(NH_4)_2SO_4$ concentration of about 0.2 M. The fraction containing NOX activity was collected, concentrated, dialyzed against 50 mM Tris-HCl (pH 8.0), then concentrated, and subsequently applied to 1.5 ml of a FAD-agarose resin (Sigma) that had been equilibrated with the same buffer. The unabsorbed proteins were thoroughly washed with the same buffer. The absorbed protein was then eluted with a buffer of 50 mM Tris-HCl and 1 mM FAD. NOX was absorbed specifically to the resin, and subsequently eluted by the addition of the buffer containing FAD. This eluted fraction was collected, and concentrated. Its purity was then examined on SDS-PAGE. As a result, NOX was observed as a single band whose molecular weight was estimated to be about 15 kDa (FIG. 7).

Using these purification steps, the specific activity of NOX was increased 6763 times from 0.029 U/mg in the crude extract to 196 U/mg. The amount of purified NOX thus obtained was 0.014 mg, and the recovery was 7.3% (Table 9).

TABLE 9

| STEP | PROTEIN (mg/ml) | ACTIVITY (U) | RECOVERY RATE (%) | SPECIFIC ACTIVITY (U/mg) | PURIFICATION (-fold) |
|---|---|---|---|---|---|
| CRUDE EXTRACT | 1253 | 37 | 100 | 0.029 | 1.0 |
| AMMONIUM SULFATE DIALYSIS | 486 | 20 | 54 | 0.041 | 1.4 |
| CHROMATOGRAPHY (Phenyl Sepharose) | 87 | 10 | 26 | 0.11 | 3.8 |
| CHROMATOGRAPHY (Q-Sepharose) | 4.2 | 3.3 | 8.9 | 0.79 | 27 |
| CHROMATOGRAPHY (FAD agarose) | 0.014 | 2.7 | 7.3 | 196 | 6763 |

The purified NOX solution was applied to Superdex 200 16/60 that had been equilibrated with 50 mM Tris-HCl (pH 8.0). Consequently, NOX was eluted at a position at which the molecular weight was estimated to be 34 kDa. In the subsequent experiments, the sample obtained by purifying NOX as a single band on SDS-PAGE and eluting through Superdex 200 16/60 was used as a purified enzyme preparation.

The NOX activity was measured in accordance with the following standard procedure. The enzyme was appropriately added to 0.1M Tris-HCl (pH 8.0), 30 μM FAD, 5 mM EDTA, 2 mM DTT, 0.2 mM NADH, and reacted at 30° C. The activity was quantified by monitoring reduction in absorbance at 340 nm caused by the production of NAD from NADH. The measurement was started at the addition of NADH. The change in absorbance in the first minute was taken as an initial rate, and the activity was calculated therefrom. The experimental group without the enzyme source was used as a blank. As to the NOX activity, the activity to oxidize 1 μmol NADH in one minute at 30° C. was defined as one unit (U). The measurement was taken three consecutive times. Their mean value was taken and is shown in the figure with the standard deviation.

Example 14

Characterization of FcDH

Using the FcDH preparation purified in Example 12 as the enzyme source, the protein was characterized.

4-1) Optimal Reaction pH

Figure 8:
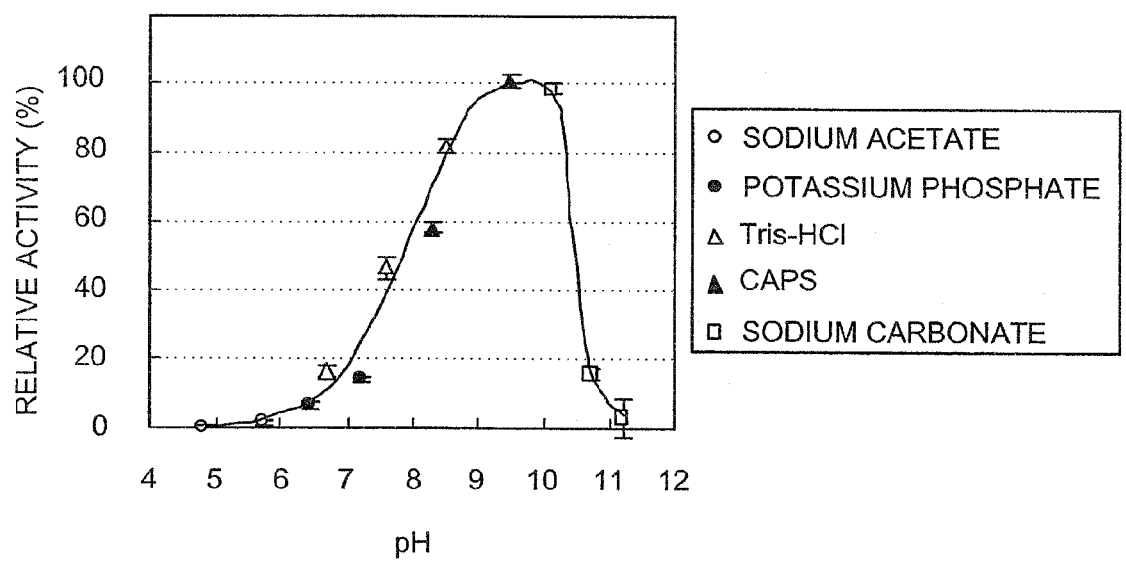
FIG. 8 shows the optimal pH when purifying FcDH.

The reaction was performed in a solution containing 0.1M pH buffer, 1 mM $MgCl_2$, 10 mM L-fucitol, 1 mM NAD, and 1.1 μg/ml purified FcDH at 30° C., and the production of NADH was determined from the measurement of $A_{340}$. As pH buffers, sodium acetate buffer (pH 4.8, 5.7), potassium phosphate buffer (pH 6.4, 7.2), Tris-HCl buffer (pH 6.7, 7.6, 8.5), CAPS-NaOH buffer (Sodium cyclohexylaminopropanesulfonate) (pH 8.3, 9.5) and sodium carbonate buffer (pH 10.1, 10.7, 11.2) were used. The specific activity of FcDH measured at each pH (FIG. 8) is reported as the relative percentage as compared to the specific activity at pH 9.5 (maximum specific activity).

4-2) pH Stability

Figure 9:
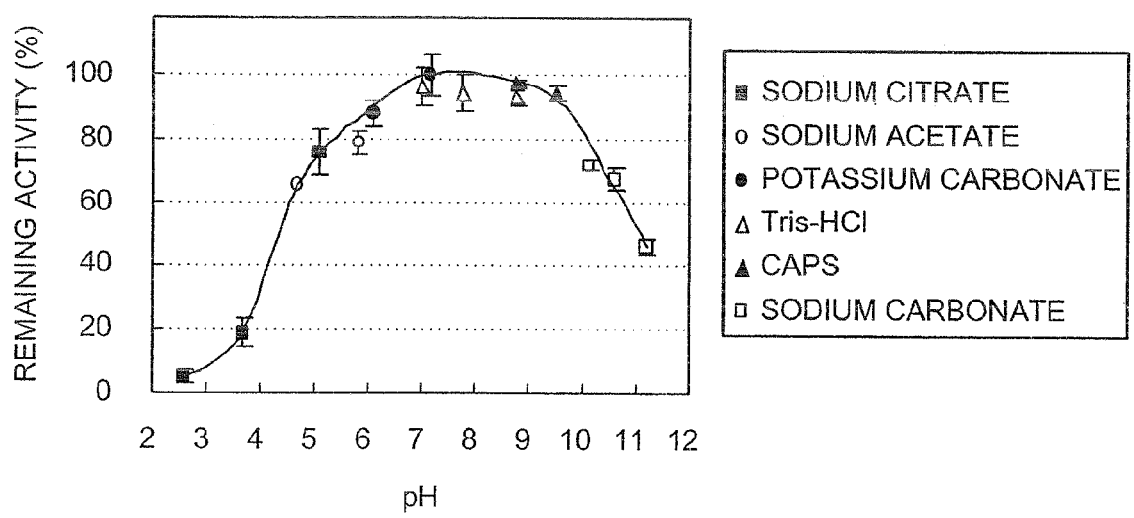
FIG. 9 shows the pH stability of purified FcDH.

A solution containing 0.1M pH buffer and 80 μg/ml purified FcDH was left to stand on ice for 30 minutes, and subsequently the solution was diluted to a final FcDH concentration of 1.6 μg/ml. The reaction was performed under standard conditions, and the remaining FcDH activity was measured. As the pH buffers, sodium citrate buffer (pH 2.6, 3.7, 5.1), sodium acetate buffer (pH 4.7, 5.8), potassium phosphate buffer (pH 6.1, 7.2), Tris-HCl buffer (pH 7.0, 7.8, 8.8), CAPS-NaOH buffer (pH 8.8, 9.5) and sodium carbonate buffer (pH 10.1, 10.6, 11.2) were used. The remaining activity of FcDH was measured at each pH (FIG. 9), and is reported as the relative percentage as compared to the remaining activity at pH 7.2 (maximum stability). As a result, 80% or more remaining activity was observed at pH of about 5 to 10.

4-3) Optimal Reaction Temperature

Figure 10:
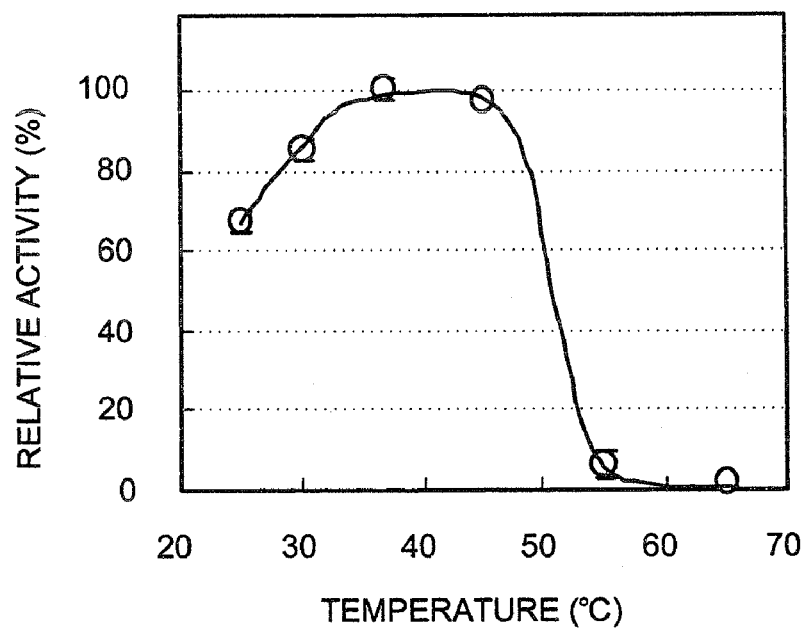
FIG. 10 shows the optimal temperature when purifying FcDH.

A solution containing Gly-NaOH (pH 9.5), $MgCl_2$, fucitol, and purified FcDH was preincubated at each temperature (25, 30, 37, 45, 55, or 65° C.) for 3 minutes, and then NAD that had been separately preincubated at each temperature was added thereto to start the reaction. The final concentrations in the reaction solution were adjusted to the standard conditions for activity measurement, and the final concentration of FcDH was 1.6 μg/ml. The specific activity of FcDH measured at each temperature (FIG. 10) is reported as the relative percentage as compared to the specific activity at 37° C. (maximum specific activity).

4-4) Temperature Stability

Figure 11:
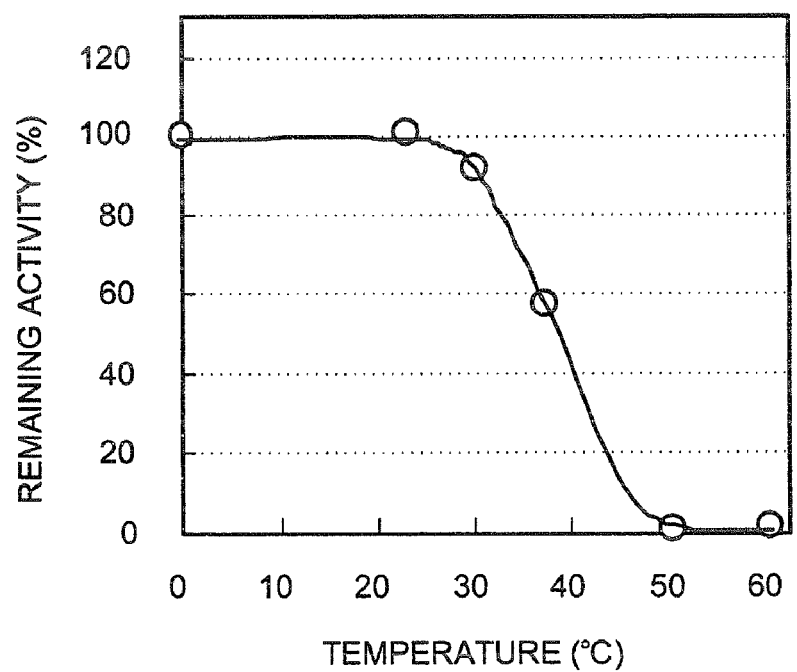
FIG. 11 shows the temperature stability of purified FcDH.

A solution containing Gly-NaOH (pH 9.5) and 80 μg/ml purified FcDH was left to stand at 0, 25, 30, 37, 50 or 60° C. for 30 minutes. The solution was then diluted so that the final concentration of FcDH was 1.6 μg/ml. The reaction was performed under standard conditions, and the remaining FcDH activity was measured. The remaining activity of FcDH measured at each temperature is reported (FIG. 11) as the relative percentage as compared to the remaining activity when left to stand at 0° C. Up to 30° C., 80% or more remaining activity was observed.

4-5) Substrate Specificity

Reactivity of FcDH to various sugar alcohols including L-fucitol was measured. Values of $k_{cat}$ and $K_m$ for each substrate were obtained by measuring the initial rate of the reaction with various substrate concentrations and drawing a Lineweaver-Burk plot of the results. The results are shown in Table 10. As a result, FcDH had oxidation activity for various sugar alcohols including L-fucitol, and the $k_{cat}$ and $K_m$ values were large in the order of D-arabitol>L-fucitol>xylitol>D-sorbitol>D-mannitol>ribitol>dulcitol>glycerol.

TABLE 10

|  | Kcat (U · mg−1) | Km (mM) | kcat/Km (U · mg$^{-1}$ · mM$^{-1}$) |
| --- | --- | --- | --- |
| D-ARABITOL | 32.9 | 1.3 | 25.19 |
| L-FUCITOL | 33.8 | 31.9 | 1.06 |
| XYLITOL | 9.3 | 31.9 | 0.29 |
| D-SORBITOL | 4.2 | 22.4 | 0.19 |
| D-MANNITOL | 4.7 | 30.2 | 0.16 |
| RIBITOL | 2.9 | 20.4 | 0.14 |
| DULCITOL | 3.1 | 30.5 | 0.10 |
| GLYCEROL | 0.9 | 10.1 | 0.09 |

Figure 12:
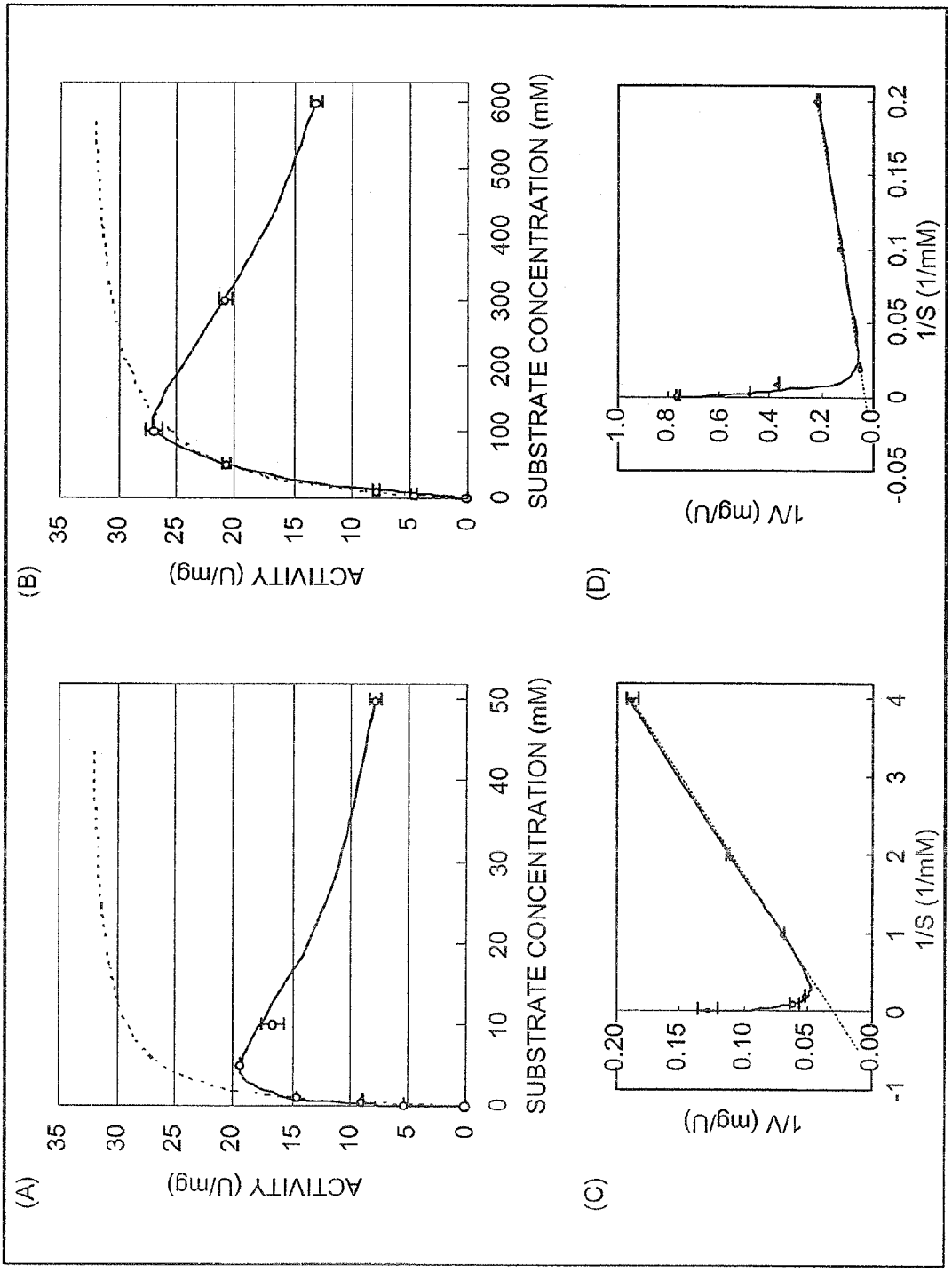
FIG. 12 shows the specific activity of purified FcDH at various concentrations of D-arabitol (A) and L-fucitol (B).

The results of measuring the specific activity of the purified FcDH are shown in FIG. 12. For D-arabitol and L-fucitol, reaction inhibition by the substrate was observed at a high concentration of the substrate. A reduction of the specific activity was observed at 5 mM or more of D-arabitol (A) and at 100 mM or more of L-fucitol (B). Lineweaver-Burk plots of the results in (A) and (B) are shown in FIG. 12 (C) and (D), respectively. The $K_m$ and $k_{cat}$ values were calculated from the range in which substrate inhibition was not observed, i.e., from a straight line represented by a broken line in FIG. 12 (C) and (D). Thus, in the cases of these substrates, the $k_{cat}$ and $K_m$ values were calculated within the range of substrate concentrations at which no inhibitory effect was observed. For other sugar alcohols, no inhibitory effect by the substrate was observed up to the substrate concentration of 100 mM.

Figure 13:
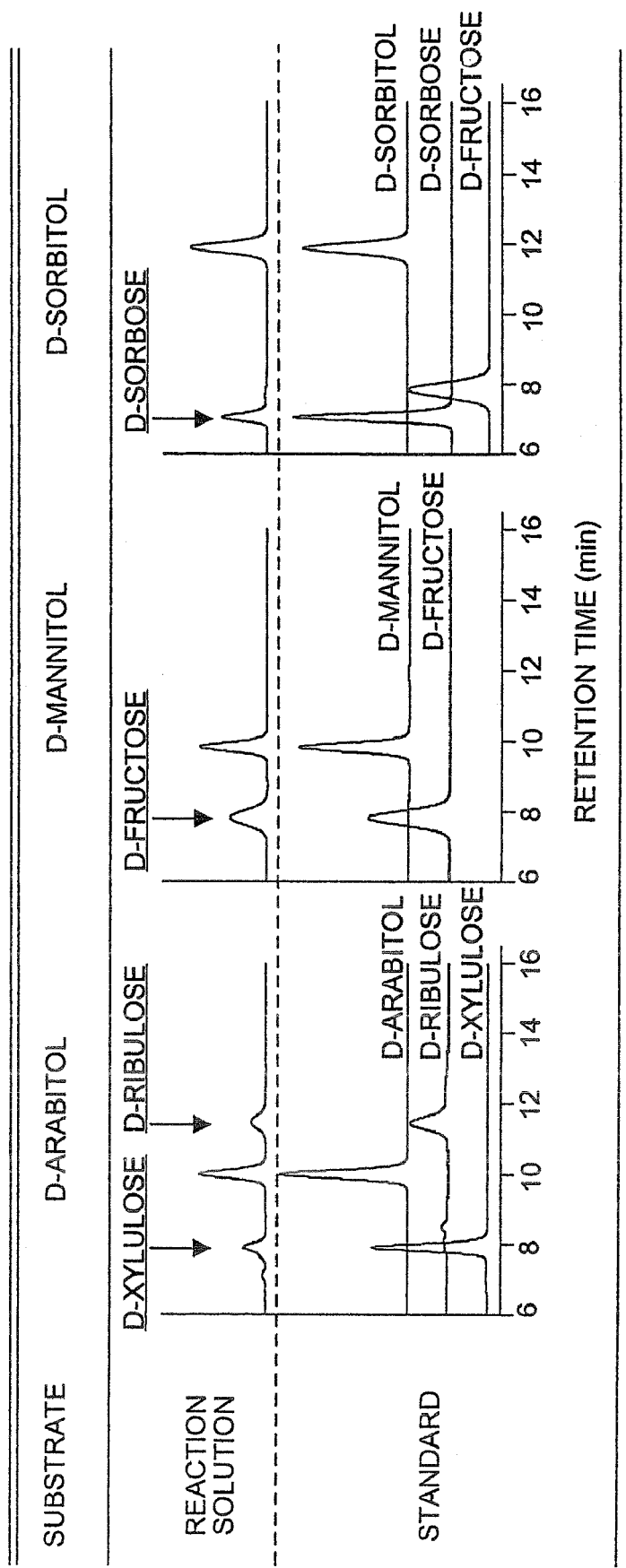
FIG. 13 shows the FcDH-oxidized products of D-arabitol, D-mannitol and D-sorbitol, as measured by HPLC analysis.

Among the substrates recognized by FcDH, the oxidation product of L-fucitol is L-fuculose, and the oxidation products of the other substrates were examined. The substrates used were D-arabitol, D-mannitol and D-sorbitol. A reaction solution containing 0.5 g/dl of the substrate, 50 mM Gly-NaOH (pH 9.5), 1 mM NAD, 30 mM FAD, 5 mM $MgCl_2$, 0.6 U/ml purified FcDH, 0.2 U/ml NOX, and 0.1 mg/ml catalase was reacted at 30° C. for 16 hours, and analyzed by HPLC (FIG. 13). As a result, the products D-ribulose and D-xylulose from D-arabitol were identified, the product D-fructose from D-mannitol was identified, and the product L-sorbose from D-sorbitol was identified.

Bivalent Metal Ion Specificity

Since it was found that the induction of FcDH activity required the addition of a bivalent ion, availability of various bivalent ions by FcDH was measured. A solution containing Gly-NaOH (pH 9.5), purified FcDH, and various bivalent metal ions (or EDTA) was left to stand on ice for 30 minutes, and then L-fucitol and NAD were added thereto to start the reaction. In the reaction solution, the final concentrations of the bivalent metal ion or EDTA were adjusted to 5 mM and the concentration of FcDH was adjusted to 1.6 μg/ml. The others were adjusted to the standard conditions. Each specific activity measured is shown in Table 11 as the relative percentage as compared to the specific activity when $MnCl_2$ was added, or the maximum specific activity. As a result, the activation effect on FcDH was almost equally observed for $Mn^{2+}$, $Mg^{2+}$ and $Ca^{2+}$ ions. However, $Ni^{2+}$ and $Co^{2+}$ ions had no effect. Conversely, $Zn^{2+}$ and $Cu^{2+}$ ions had an inhibitory effect.

When the bivalent metal ion was chelated by EDTA, the activity of FcDH nearly disappeared.

TABLE 11

| ADDED REAGENT | RELATIVE ACTIVITY (%) |
|---|---|
| none | 35.1 ± 0.5 |
| $MnCl_2$ | 100.0 ± 6.9 |
| $MgCl_2$ | 93.7 ± 2.9 |
| $CaCl_2$ | 89.9 ± 3.4 |
| $NiCl_2$ | 42.4 ± 0.7 |
| $CoCl_2$ | 34.8 ± 1.1 |
| $ZnSO_4$ | 11.7 ± 0.5 |
| $CuCl_2$ | 5.0 ± 0.5 |
| EDTA | 3.2 ± 0.7 |

4-7) NAD and NADP Specificity

Figure 14:
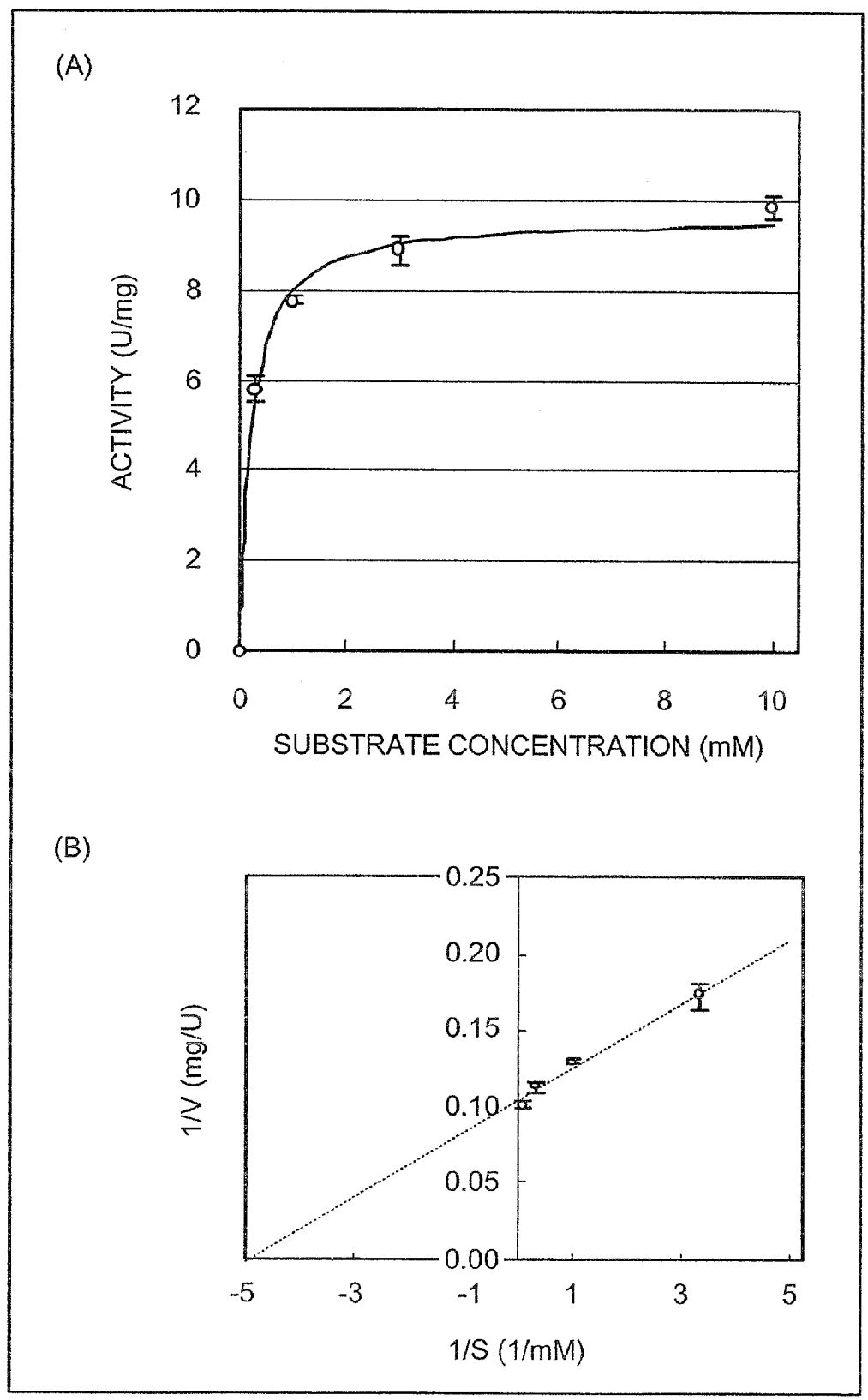
FIG. 14 shows the specific activity of purified FcDH at various NAD concentrations.

Since FcDH uses NAD as a coenzyme, the availability of NAD and NADP was measured. The activity was measured by adding NAD or NADP at various concentrations under standard conditions. The $K_m$ value for each coenzyme was calculated by drawing a Lineweaver-Burk plot of the results (FIG. 14 (B)). As a result, as shown in FIG. 14, the $K_m$ value for NAD was determined to be 0.20 mM. Meanwhile, when NADP was used as the coenzyme, no significant activity was observed (data not shown).

Example 15

Characterization of NOX

Using the NOX preparation purified in Example 13 as the enzyme source, the protein was characterized.

15-1) Optimal Reaction pH

Figure 15:
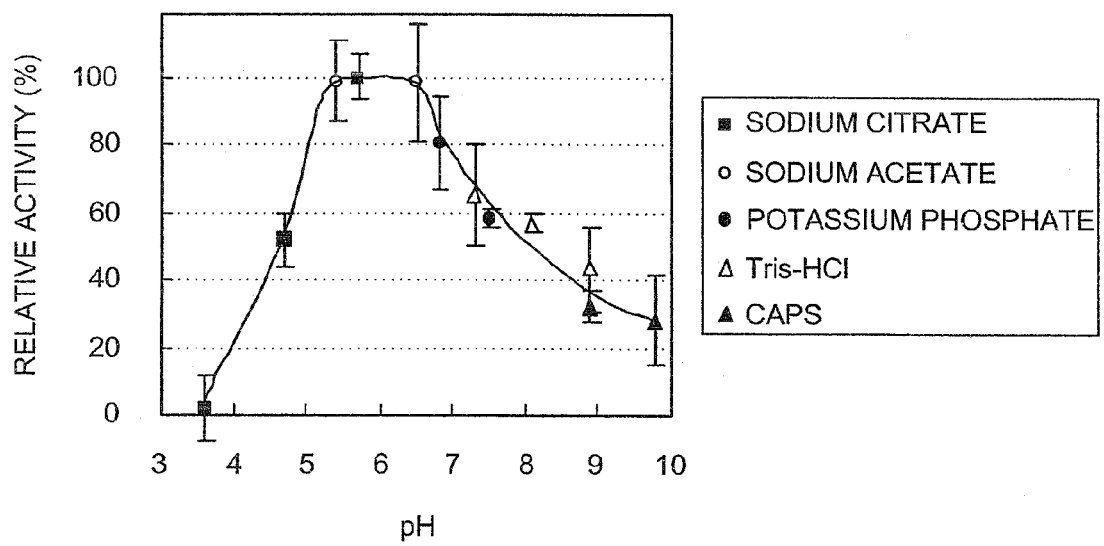
FIG. 15 shows the optimal pH when purifying NOX.

The reaction was performed in a solution containing 0.1M pH buffer, 30 μM FAD, 5 mM EDTA, 2 mM DTT, 0.2 mM NADH and 0.055 μg/ml purified NOX at 30° C., and the reduction of NADH was determined from the measurement at $A_{340}$. As pH buffers, sodium citrate buffer (pH 3.6, 4.7, 5.7), sodium acetate buffer (pH 4.8, 5.7), potassium phosphate buffer (pH 6.4, 7.2), Tris-HCl buffer (pH 6.7, 7.6, 8.5), and CAPS-NaOH buffer (pH 8.3, 9.5) were used. The specific activity of NOX measured at each pH (FIG. 15) is reported as the relative percentage as compared to the specific activity at pH 5.7, or the maximum specific activity.

pH Stability

Figure 16:
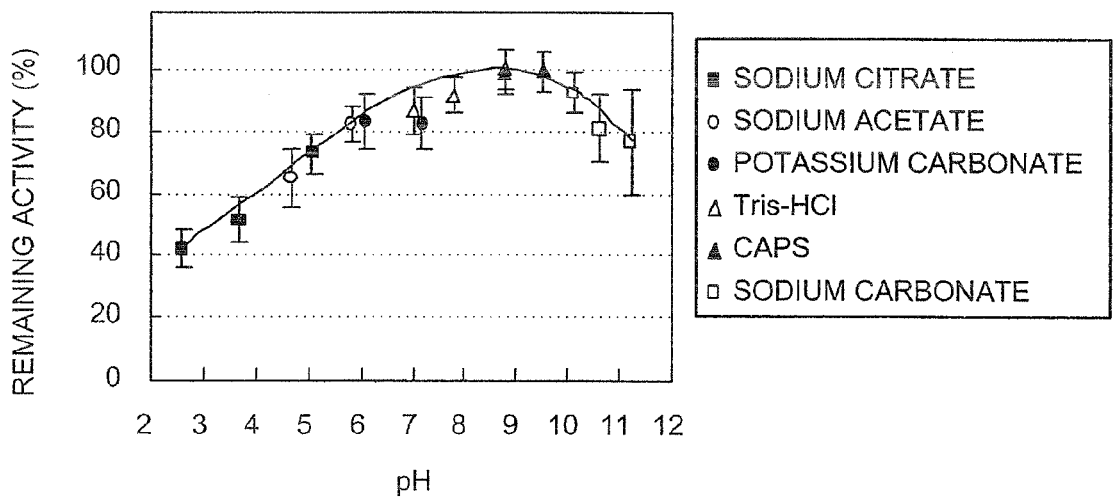
FIG. 16 shows the pH stability of purified NOX.

A solution containing 0.1M pH buffer, 30 μM FAD, 5 mM EDTA, 2 mM DTT, and 100 μg/ml purified NOX was left to stand on ice for 30 minutes, and subsequently the solution was diluted so that the final concentration of FcDH was 0.055 μg/ml. The reaction was performed under standard conditions, and the remaining NOX activity was measured. As the pH buffers, sodium citrate buffer (pH 2.6, 3.7, 5.1), sodium acetate buffer (pH 4.7, 5.8), potassium phosphate buffer (pH 6.1, 7.2), Tris-HCl buffer (pH 7.0, 7.8, 8.8), CAPS-NaOH buffer (pH 8.8, 9.5) and sodium carbonate buffer (pH 10.1, 10.6, 11.2) were used. The remaining activity of NOX measured at each pH (FIG. 16) is reported as the relative percentage as compared to the remaining activity at pH 8.8, or maximum stability. As a result, 80% or more remaining activity was observed at pH of about 6 to 11.

15-3) Optimal Reaction Temperature

Figure 17:
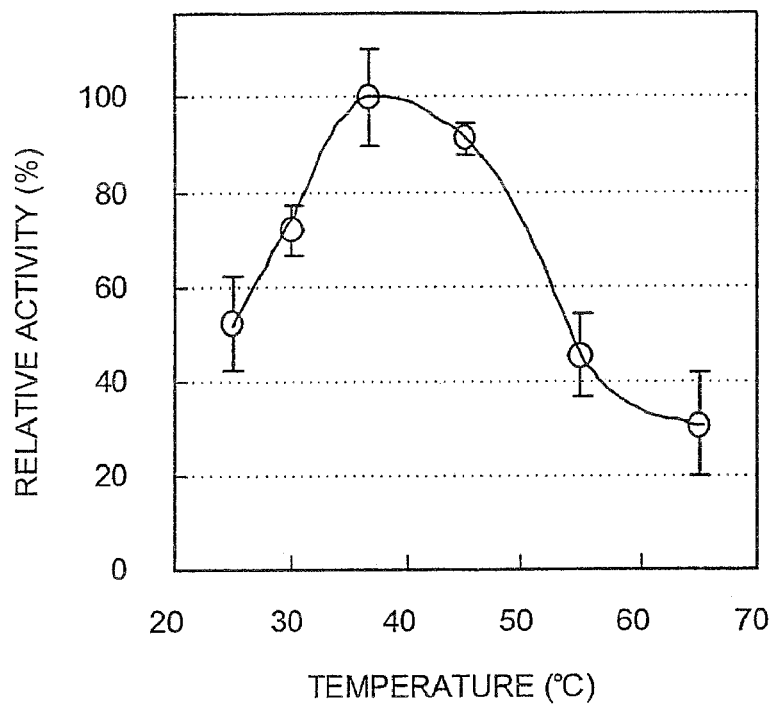
FIG. 17 shows the optimal temperature when purifying NOX.

A solution containing Tris-HCl (pH 8.0), FAD, EDTA, DTT, and purified NOX was preincubated at each temperature (25, 30, 37, 45, 55 or 65° C.) for 3 minutes, and then NADH that had been separately preincubated at each temperature was added thereto to start the reaction. The final concentrations in the reaction solution were adjusted to standard conditions of the activity measurement, and the final concentration of NOX was 0.055 μg/ml. The specific activity of NOX measured at each temperature (FIG. 17) is reported as the relative percentage (remaining activity) as compared to the specific activity at 37° C., or maximum specific activity.

15-4) Temperature Stability

Figure 18:
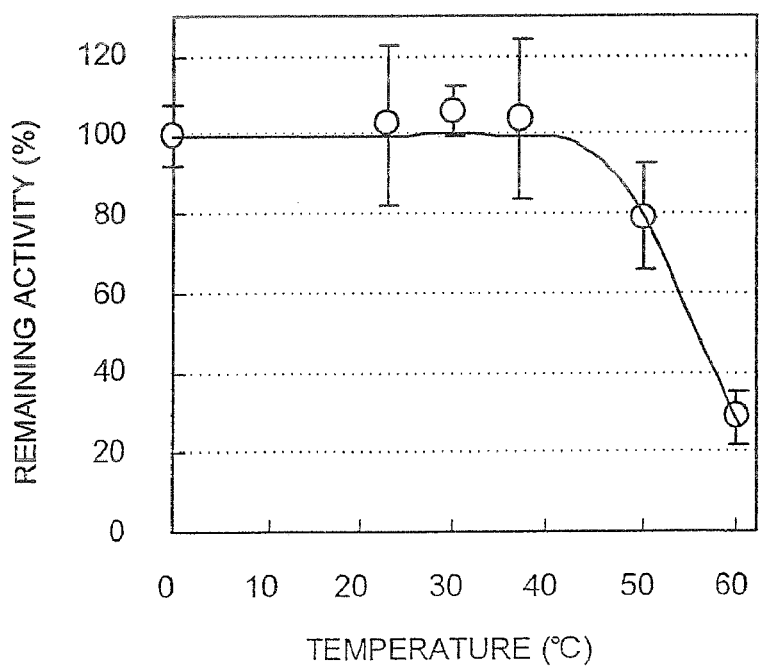
FIG. 18 shows the temperature stability of purified NOX.

The solution containing 0.1M Tris-HCl (pH 8.0), 30 μM FAD, 5 mM EDTA, 2 mM DTT, and 100 μg/ml purified NOX was left to stand at 0, 25, 30, 37, 50 or 60° C. for 30 minutes. The solution was then diluted so that the final concentration of NOX was 0.055 μg/ml. The reaction was performed under standard conditions, and the remaining NOX activity was measured. The remaining activity of NOX measured at each temperature (FIG. 18) is reported as the relative percentage as compared to the remaining activity when left to stand at 0° C. Up to 50° C., 80% or more remaining activity was observed.

15-5) Flavin Coenzyme Specificity

Figure 19:
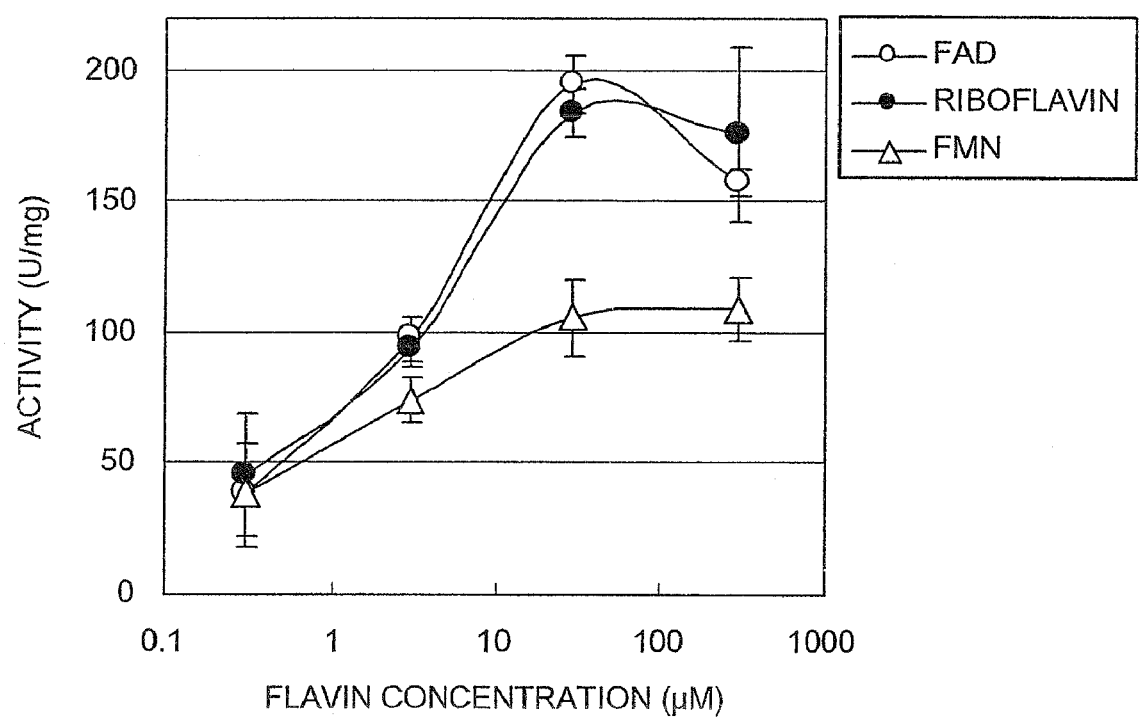
FIG. 19 shows the specific activity of purified NOX at various concentrations of flavin coenzymes (FAD, riboflavin and FMN).

Since it was found that the induction of NOX activity required the addition of a flavin coenzyme, the availability of various flavin coenzymes was measured. The solution containing Tris-HCl (pH 8.0), FAD, EDTA, DTT, purified NOX, and any of various flavin coenzymes was left to stand on ice for 30 minutes, and then NADH was added thereto to start the reaction. The concentration of flavin in the reaction solution was 0 to 300 μM, and the others were adjusted to standard conditions. The results are shown in FIG. 19. As a result, the NOX activation effect was observed for FAD, riboflavin, and FMN, and the effect was almost equal with FAD and riboflavin, and relatively weaker with FMN.

15-6) NADH and NADPH Specificity

Figure 20:
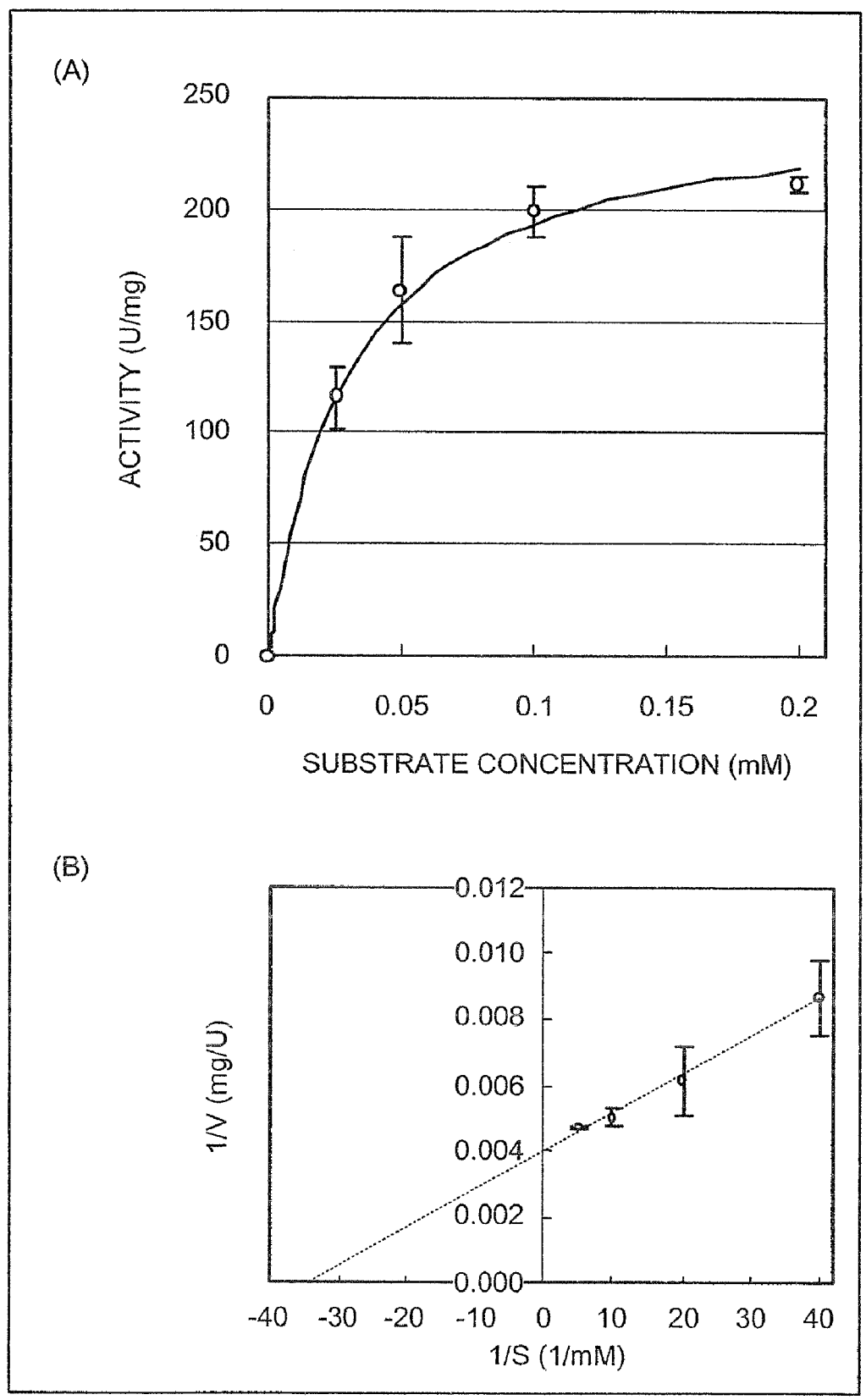
FIG. 20 shows the specific activity of purified NOX at various concentrations of NADH (FIG. 20 (A)).

Since it was found that NOX had NADH oxidation activity, the substrate specificity for NADH and NADPH was measured. The $K_m$ value for the substrate was calculated by measuring the activity with a variety of substrate concentrations and drawing a Lineweaver-Burk plot of the results. As a result, the $K_m$ value for NADH was determined to be 29 μM (FIG. 20). Meanwhile, when NADPH was used as the substrate, no significant activity was observed (data not shown).

Example 16

Determination of Partial Amino Acid Sequences of FcDH and NOX

Using the purified FcDH and NOX, partial amino acid sequences were determined. Both enzymes were subjected to SDS-PAGE, the part of the gel containing the band was cut out, and the protein contained therein was used as the sample. In accordance with standard methods, the protein was fragmented by treatment with trypsin, and then separated by reverse phase HPLC to yield several fractions. These fractions were subjected to the protein sequencer. The sequences are shown in SEQ ID NOS:11 to 14.

Example 17

Cloning of Genes Encoding FcDH and NOX

In order to clone the gene encoding FcDH or NOX, DNA primers corresponding thereto were synthesized from the peptide sequences obtained in Example 16. PCR was performed using genomic DNA prepared from *G. oxydans* IFO 3255 as the template in accordance with standard methods. The resulting fragment was purified and its nucleotide sequence was analyzed by the DNA sequencer. As a result, the DNA sequences encoding the peptide sequences obtained in Example 16 were determined.

Subsequently, Southern hybridization and colony hybridization were performed using this DNA fragment as a probe in accordance with standard methods. The plasmids were prepared from the resulting clones, and their DNA sequences were analyzed to obtain a FcDH-encoding gene (fcdh) consisting of 774 bases (including the termination codon) shown in SEQ ID NO:15 and a NOX-encoding gene (nox) consisting of 474 bases (including the termination codon) shown in SEQ ID NO:17. The entire amino acid sequence of FcDH consisting of 257 amino acid residues (SEQ ID NO:16) and the entire amino acid sequence of NOX consisting of 157 amino acid residues (SEQ ID NO:18) were determined from these nucleotide sequences. These included the peptide sequences determined in Example 6. The molecular weights estimated from the amino acid sequences were 27,522 Da for FcDH and 16,777 Da for NOX, which were almost identical to the molecular weights determined with SDS-PAGE.

Example 18

Preparation of Strains Expressing FcDH, FcDH+NOX, or FcDH+NOX+FucI, and Cultivation Thereof For the expression of FcDH, PCR was performed with the genomic DNA from *G. oxydans* IFO 3255 strain as the template and the synthetic primers shown in SEQ ID NOS:19 and 20, to yield a fragment of 858 bp including the fcdh gene. The resulting PCR product was digested with EcoRI and PstI and inserted into the corresponding position in the plasmid pUC18 (Takara Bio Inc.) to prepare the plasmid pFEX3052 for the expression of FcDH.

Subsequently in order to obtain the nox gene, PCR was performed with the genomic DNA from *G. oxydans* IFO 3255 strain as the template and the synthetic primers shown in SEQ ID NOS:21 and 22, to yield a fragment of 605 bp including the nox gene. The resulting PCR product was digested with PstI and HindIII, and inserted into the corresponding position in the plasmid pFEX3052 to prepare the plasmid pFNEX4105 for the co-expression of FcDH and NOX.

PCR was performed with plasmid pFNEX4105 as the template and the synthetic primers shown in SEQ ID NOS: 19 and 23, to yield a fragment of 1390 bp including a gene fragment in which the fcdh gene and the nox gene had been ligated in tandem. The resulting PCR product was digested with EcoRI and KpnI, and subsequently inserted into the corresponding position in the plasmid pUC18 to prepare pFNEX4502.

Subsequently, in order to obtain the fucI gene encoding FucI, PCR was performed with the genomic DNA obtained from *E. coli* W3110 strain and the primers shown in SEQ ID NOS:24 and 25 synthesized based on the fucI gene sequence described in Accession No. NC_000913, to yield a fragment of 1873 bp including the fucI gene. The resulting PCR product was digested with KpnI and SalI, and subsequently inserted into the corresponding position in the plasmid pFNEX4502 to prepare the plasmid pFNIEX5706 for the co-expression of FcDH, NOX and FucI. Because of the need to provide FucI for the subsequent experiments, the plasmid pIEX11 for the expression of FucI alone was prepared. This was prepared by performing PCR similar to above using the synthetic primers shown in SEQ ID NOS:26 and 27 to yield the fucI gene, digesting the resulting product with EcoRI and PstI, and inserting it into the corresponding position in the plasmid pUC18.

*Escherichia coli* JM 109 strain (supplied from Takara Bio Inc.) was transformed with the constructed plasmids pFEX3052, pFNEX4105, pFNIEX570 or pIEX11 to produce FcDH-expressing strain *E. coli*/pFEX3052, FcDH and NOX co-expressing strain *E. coli*/pFNEX4105, FcDH, NOX, and FucI co-expressing strain *E. coli*/pFNIEX5706 and FucI-expressing strain *E. coli*/pIEXI11.

These strains and *E. coli*/pUC18 transformed with unmodified pUC18 as a control were refreshed by culturing on LB/Amp plates at 37° C. LB/Amp liquid medium was used for the liquid cultivation, and the cultivation was performed at 37° C. After inoculating the refreshed microbial cells, IPTG was added to a final concentration of 1 mM. The microbial cells were cultured for 6 to 18 hours and then collected by centrifugation. The collected microbial cells were washed with 25 mM Tris-HCl buffer (pH 8.0) and used in subsequent experiments. TB medium (12 g/l trypton, 24 g/l yeast extract, 4 g/l glycerol, 2.3 g/l $KH_2PO_4$, 12.5 g/l $K_2HPO_4$) was used instead of LB medium in some cases, and they were not essentially different, except that a larger amount of microbial cells was obtained.

Example 19

Figure 21:
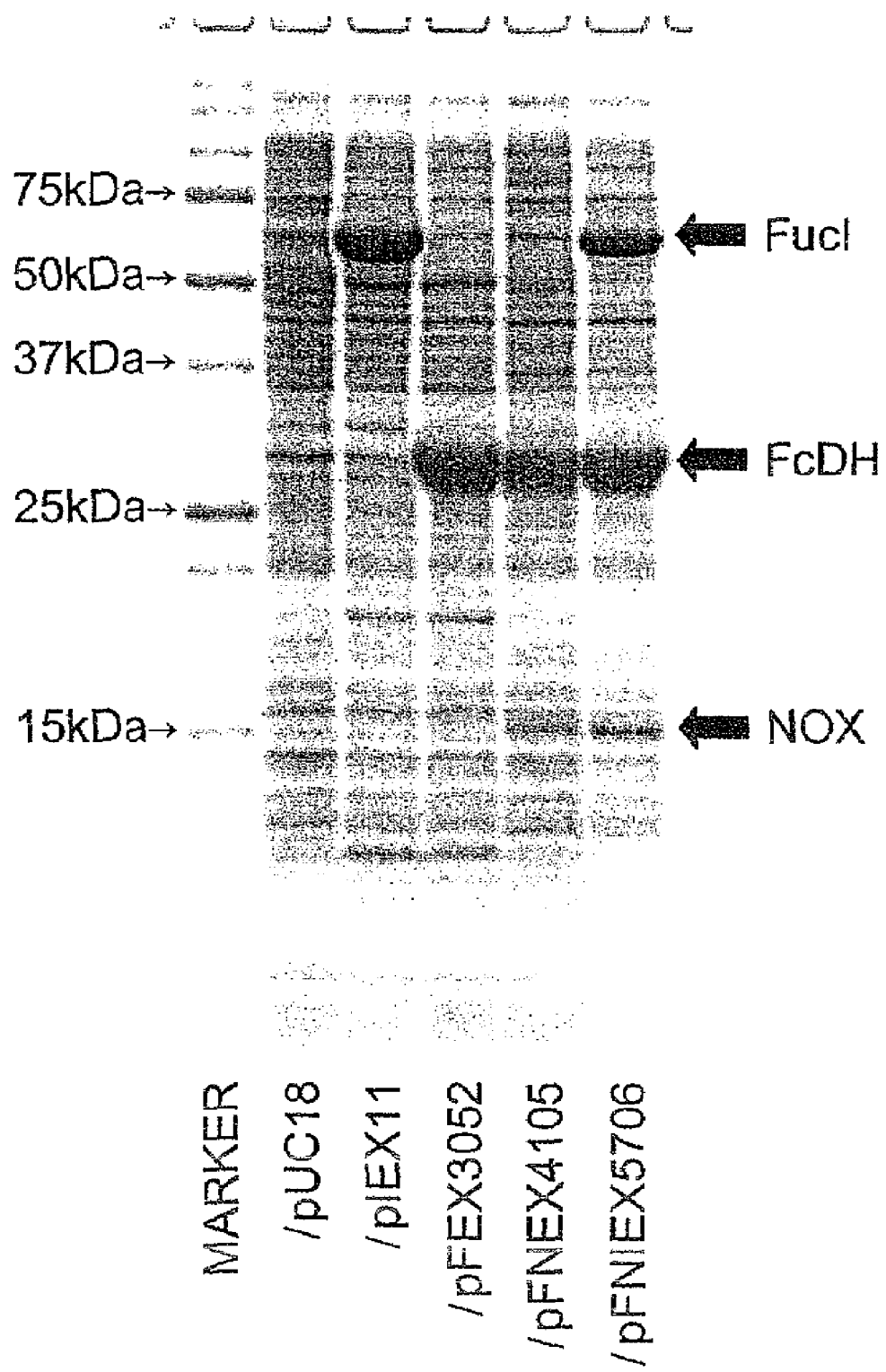
FIG. 21 shows the SDS-PAGE profiles of cell free extracts prepared from *E. coli*/pUC18, *E. coli*/pIEX11, *E. coli*/pFEX3052, *E. coli*/pFNEX4105 and *E. coli*/pFNIEX5706.

Preparation of Cell-Free Extract and Purification of Expressed Protein (19-1) Preparation of Cell-Free Extract The washed microbial cells were resuspended in 25 mM Tris-HCl (pH 8.0), and disrupted by sonication (200 W, 10 minutes). Then the supernatant was obtained by centrifugation at 14,000 g for 15 minutes, and this was used as the cell-free extract in the various experiments. The result of analysis of the cell-free extracts obtained from *E. coli*/pUC18, *E. coli*/pIEX11, *E. coli*/pFEX3052, *E. coli*/pFNEX4105 and *E. coli*/pFNIEX5706 on SDS-PAGE is shown in FIG. 21. FucI was produced with *E. coli*/pIEX11. FcDH was produced with *E. coli*/pFEX3052. FcDH and NOX were produced with *E. coli*/pFNEX4105. FucI, FcDH, and NOX were produced with *E. coli*/pFNIEX5706. Each band was observed at the position of the corresponding molecular weight. When the expressed protein was purified, this cell-free extract was further subjected to ultracentrifugation at 200,000 g for 30 minutes, and the resulting supernatant was used.

(19-2) Purification of Expressed Recombinant FcDH (rFcDH)

Figure 22:
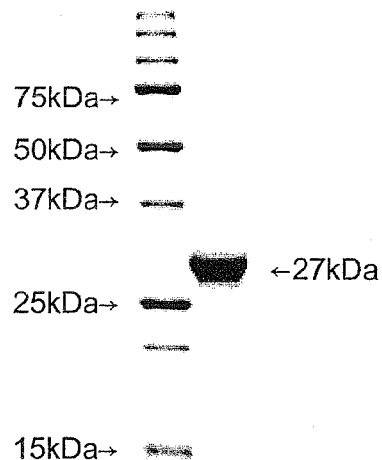
FIG. 22 shows the SDS-PAGE profile of rFcDH purified from *E. coli*/pFEX3052.

The supernatant obtained by ultracentrifugation of the cell-free extract obtained from *E. coli*/pFEX3052 was purified. The crude enzyme solution was dialyzed against 50 mM potassium phosphate buffer (pH 6.0), and applied onto Q-Sepharose 16/10 that had been equilibrated with the same buffer. The protein which absorbed onto the carrier was eluted by increasing the NaCl concentration from 0 M to 0.5 M in the buffer. The fraction containing the FcDH activity was collected, concentrated, and then applied onto Superdex 200 16/60 that had been equilibrated with 50 mM potassium phosphate buffer (pH 6.0). The fraction containing the FcDH activity was collected, concentrated, and its purity was then examined on SDS-PAGE. As a result, rFcDH was observed as a single band whose molecular weight was determined to be about 27 kDa (FIG. 22).

(19-3) Purification of Expressed Recombinant NOX (rNOX)

Figure 23:
FIG. 23 shows the SDS-PAGE profile of rNOX purified from *E. coli*/pFNEX4105.

The supernatant obtained by ultracentrifugation of the cell-free extract of *E. coli*/pFNEX4105 was purified. The crude enzyme solution was applied onto FAD-agarose resin that had been equilibrated with 50 mM Tris-HCl (pH 8.0), and unabsorbed proteins were thoroughly washed with the same buffer. The absorbed protein was then eluted with the buffer containing 50 mM Tris-HCl (pH 8.0) and 1 mM FAD. NOX was specifically absorbed onto the resin, and eluted by the addition of the buffer containing FAD. The fraction containing the NOX activity was collected, concentrated, and then applied onto Superdex 200 16/60 that had been equilibrated with 50 mM Tris-HCl (pH 8.0), to collect the fraction containing the NOX activity. This was concentrated, and its purity was then examined on SDS-PAGE. As a result, rNOX was observed as a single band whose molecular weight was determined to be about 15 kDa (FIG. 23).

(19-4) Measurement of Enzyme Activity

The activity of FcDH, NOX, and FucI in the cell-free extracts obtained from E. coli/pUC18, E. coli/pIEX11, E. coli/pFEX3052, E. coli/pFNEX4105, and E. coli/pFNIEX5706 was measured (Table 12). The activity of the purified preparations of rFcDH and rNOX that had been purified as described above was also measured. The specific activity of rFcDH was 11.1 U/mg, and that of rNOX was 175 U/mg. These values are sufficiently similar to the specific activities 7.8 U/mg of FcDH and 196 U/mg of NOX purified from G. oxydans.

TABLE 12

| Plasmids | ENZYME ACTIVITY (U/mg) | | |
|---|---|---|---|
| | FcDH | NOX | FucI |
| pUC18 | ND* | 0.03 | ND* |
| pIEX11 | NT** | NT** | 0.84 |
| pFEX3052 | 3.08 | 0.04 | ND* |
| pFNEX4105 | 2.95 | 5.90 | ND* |
| pFNIEX5706 | 3.55 | 6.08 | 0.27 |

*ND, Not detected
**NT, Not tested

The FucI activity was measured as follows. The enzyme solution was appropriately added to 0.1M L-fucose, 0.1M Tris-HCl (pH 8.0), and 5 mM $MgCl_2$, and reacted at 30° C. The activity was quantified by measuring the amount of L-fuculose produced by the isomerization of L-fucose by HPLC. The activity was calculated from the range in which the amount of produced L-fuculose did not exceed 3 mM. As to the FucI activity, the activity to produce L-fuculose by isomerizing 1 μmol of L-fucose in one minute at 30° C. was defined as 1 U.

The relationship between the expressed gene and the measured enzyme activity was reasonable, and the fcdh gene and the nox gene encoded FcDH and NOX, respectively. A subtle level of nox activity was observed in the experimental group in which nox had not been expressed, which was thought to be derived from the host E. coli.

Example 20

Conversion of L-Fucitol by Enzyme Reaction (20-1) Conversion by a Purified Enzyme Prepared from G. oxydans IFO 3255

Using purified FcDH and NOX prepared from G. oxydans, the conversion of L-fucitol to L-fuculose or L-fucose was attempted. The enzymatic conversion from L-fuculose to L-fucose requires L-fucose isomerase. FucIH6 prepared from E. coli/pQE30FucIH6 was used. As the enzymes having NOX activity, an $H_2O$ producing type and an $H_2O_2$ producing type have been reported. In the case of the $H_2O_2$ producing type, as NADH is oxidized, $H_2O_2$ is produced. Generally, $H_2O_2$ is usally able to inhibit the activity of many enzymes. Thus, to avoid this, catalase was added to convert $H_2O_2$ into $H_2O$. As catalase, a commercially available preparation (Nacalai Tesque, derived from bovine liver) was used. As standard reaction conditions, a reaction solution containing 62 mM L-fucitol, 0.1M Gly-NaOH (pH 9.5), 2 mM NAD, 30 μM FAD, 1 mM $MgCl_2$, 0.1 U/ml purified FcDH, 0.1 U/ml purified NOX, 0.2 mg/ml purified FucIH6, and 0.1 mg/ml catalase was reacted at 30° C. with shaking while sampling was appropriately performed. L-fucitol, L-fuculose, and L-fucose were quantified by HPLC. The experimental groups and the results after the reaction for 48 hours are shown in Table 13. The conversion time course in each experimental group is shown in FIG. 24.

TABLE 13

| EXPERI-MENTAL GROUP | CONDITION | AFTER CONVERSION FOR 48 HOURS | | |
|---|---|---|---|---|
| | | L-FUCOSE (mM) | L-FUCULOSE (mM) | L-FUCITOL (mM) |
| A | NO ADDITION OF ENZYME | 0.0 | 0.0 | 67.1 |
| B | STANDARD CONDITION | 54.2 | 6.4 | 3.3 |
| C | NO ADDITION OF FucIH6 | 0.0 | 45.7 | 13.4 |
| D | NO ADDITION OF FcDH | 0.2 | 0.0 | 64.2 |
| E | NO ADDITION OF NOX | 3.9 | 0.7 | 57.4 |
| F | NO ADDITION OF CATALASE | 26.1 | 6.0 | 29.0 |

Figure 24:
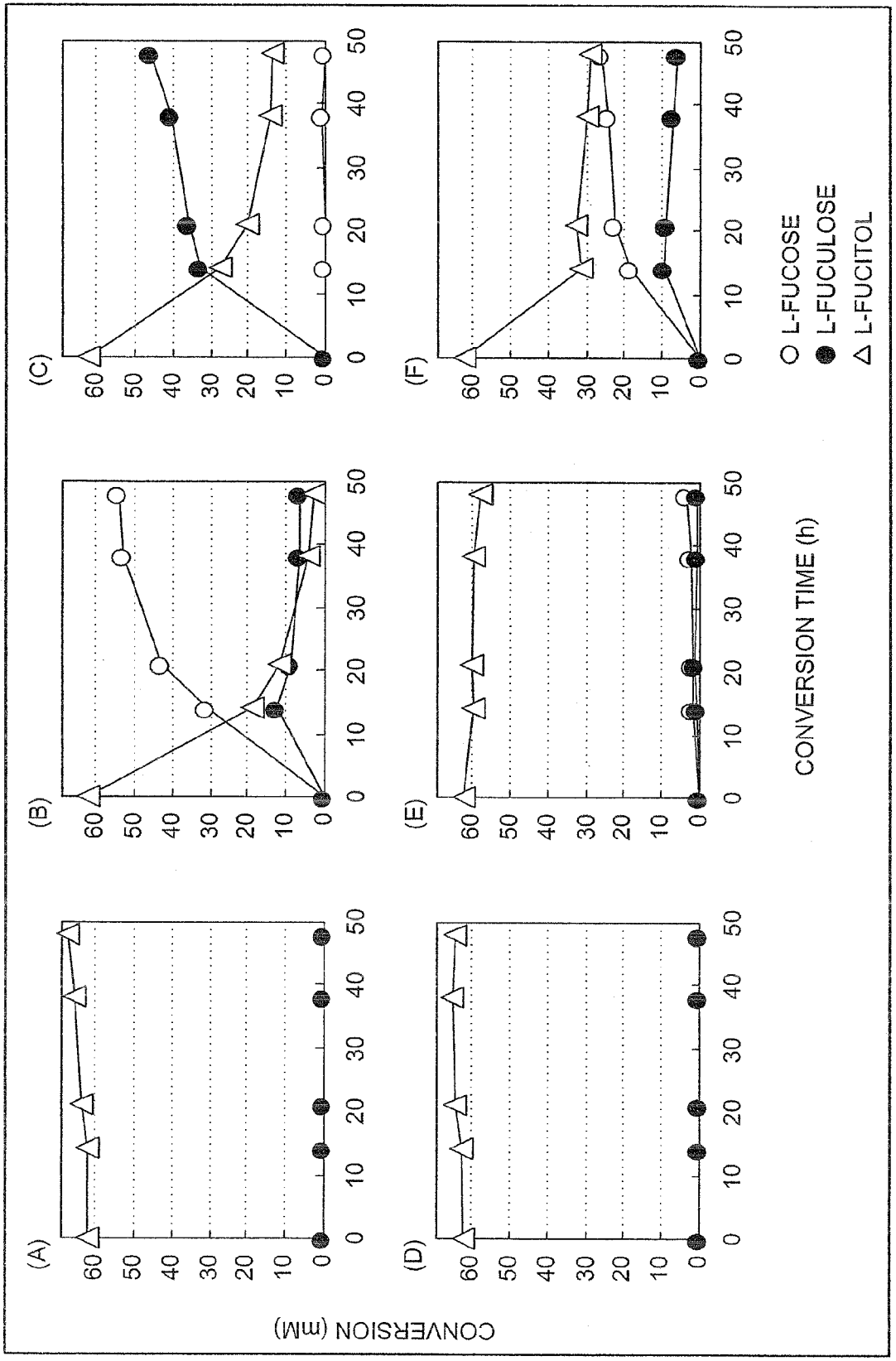
FIG. 24 shows the time courses of L-fucitol conversion using FcDH and NOX purified from *G. oxydans*.

In each plot in FIG. 24, open circles, solid circles, and open triangles represent the concentrations of L-fucose, L-fuculose, and L-fucitol, respectively. (B) shows the result under standard conditions (62 mM L-fucitol, 0.1M Gly-NaOH (pH 9.5), 2 mM NAD, 30 μM FAD, 1 mM $MgCl_2$, 0.1 U/ml purified FcDH, 0.1 U/ml purified NOX, 0.2 mg/ml purified FucIH6, and 0.1 mg/ml catalase). (A) shows the result without any addition of the enzymes, (C) shows the result without addition of FucIH6, (D) shows the result without addition of FcDH, (E) shows the result without addition of NOX and (F) shows the result without addition of catalase.

From the results shown in Table 13 and FIG. 24, the presence of both enzymes FcDH and NOX enabled the recycling of NAD(H), and the addition of 2 mM NAD led to the production of 50 mM or more L-fuculose from L-fucitol. By the additional presence of the FucI enzyme, the L-fuculose which was produced was converted into L-fucose, and consequently it was possible to produce L-fucose from L-fucitol. The inhibition of the conversion was observed in the group in which catalase was not added. Thus, it was suggested that NOX used here was the $H_2O_2$ producing type since $H_2O_2$ inhibited the oxidation of L-fucitol and the $H_2O_2$ which was produced could be removed by the addition of catalase.

(20-2) Conversion by Expressed Recombinant Enzyme Prepared from E. coli

Using rFcDH and rNOX purified after expression in E. coli, the enzymatic conversion of L-fucitol was attempted in the same way as in (20-1). As the standard reaction conditions, a reaction solution containing 120 mM L-fucitol, 0.1M Gly-NaOH (pH 9.5), 2 mM NAD, 30 μM FAD, 1 mM $MgCl_2$, 1 U/ml purified rFcDH, 1 U/ml purified rNOX, 0.2 mg/ml purified FucIH6, and 0.1 mg/ml catalase was reacted at 30° C. with shaking, while sampling was appropriately performed. L-fucitol, L-fuculose, and L-fucose were quantified by HPLC. The experimental groups and the results after 40 hours are shown in Table 14. The conversion time course in each experimental group is shown in FIG. 25.

TABLE 14

| EXPERI-MENTAL GROUP | CONDITION | AFTER CONVERSION FOR 40 HOURS | | |
|---|---|---|---|---|
| | | L-FUCOSE (mM) | L-FUCULOSE (mM) | L-FUCITOL (mM) |
| A | STANDARD CONDITION | 113.0 | 14.8 | 0.0 |
| B | NO ADDITION OF NAD | 0.2 | 0.0 | 121.2 |
| C | NO ADDITION OF FAD | 62.3 | 13.0 | 48.7 |
| D | NO ADDITION OF CATALASE | 91.5 | 23.6 | 14.2 |
| E | NO ADDITION OF FucIH6 | 0.0 | 95.6 | 28.0 |

Figure 25:
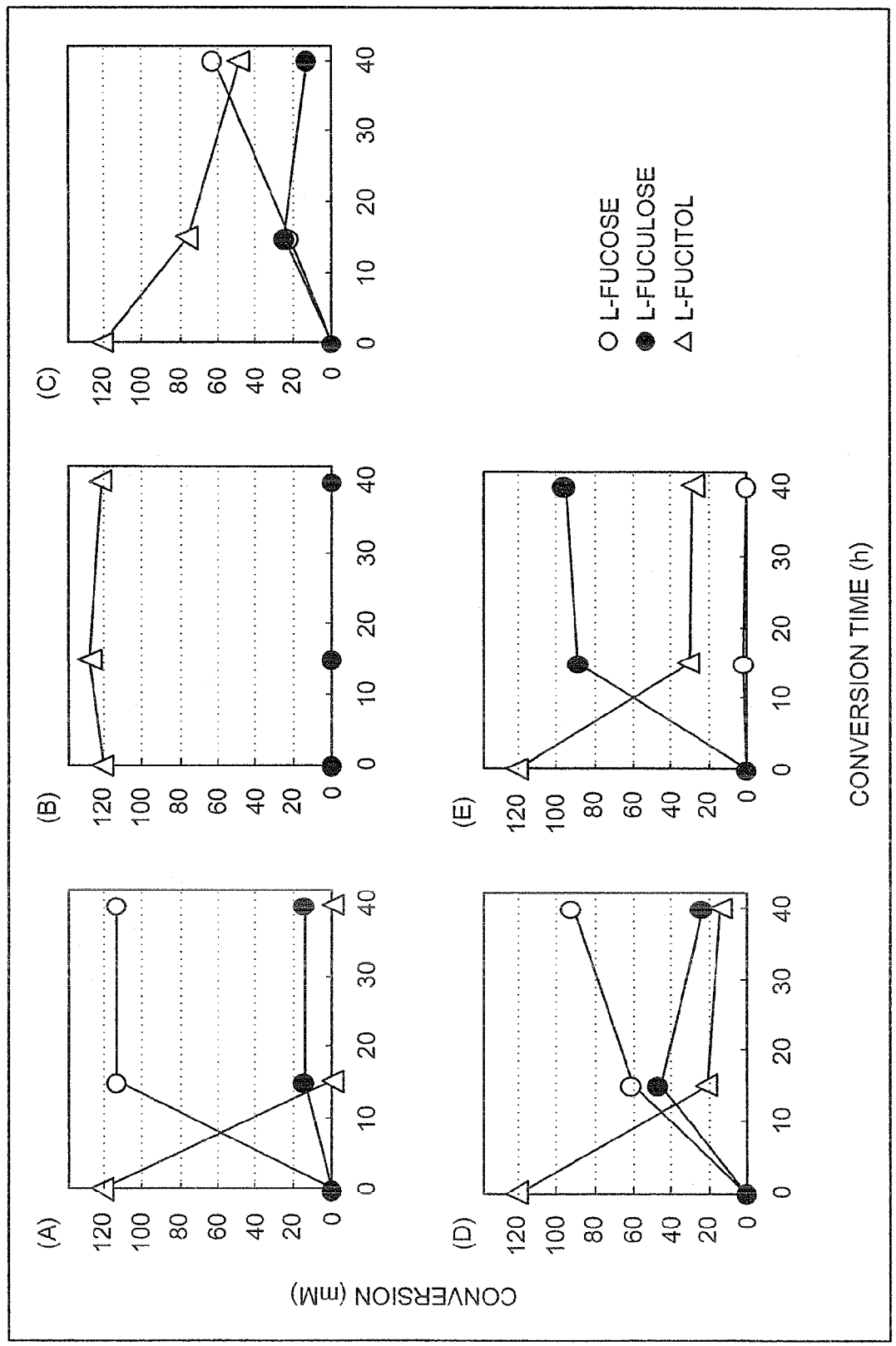
FIG. 25 shows the time courses of L-fucitol conversion using rFcDH and rNOX prepared from recombinant *E. coli*.

In each plot in FIG. 25, open circles, solid circles, and open triangles represent the concentrations of L-fucose, L-fuculose, and L-fucitol, respectively. (A) shows the result under standard conditions (120 mM L-fucitol, 0.1M Gly-NaOH (pH 9.5), 2 mM NAD, 30 µM FAD, 1 mM $MgCl_2$, 1 U/ml purified rFcDH, 1 U/ml purified rNOX, 0.2 mg/ml purified FucIH6, and 0.1 mg/ml catalase). (B) shows the result without addition of NAD, (C) shows the result without addition of FAD, (D) shows the result without addition of catalase, and (E) shows the result without addition of FucIH6.

From the results shown in Table 14 and FIG. 25, the presence of both enzymes rFcDH and rNOX enabled the recycling of NAD(H), similar to FcDH and NOX prepared from *G. oxydans*, and the addition of 2 mM NAD led to production of 100 mM or more L-fuculose from L-fucitol. In the presence of the FucI enzyme, L-fuculose which was produced was converted into L-fucose, and consequently L-fucose could be produced from L-fucitol. The effect of catalase addition was observed as in the above (20-1). In the present experiment, the necessity of the addition of the coenzymes NAD and FAD was also examined. In the experimental group in which NAD was not added, the conversion of L-fucitol did not proceed at all even though both enzymes FcDH and NOX were present. Thus, the addition of NAD at least in a catalytic amount was necessary for the conversion. In the experimental group in which FAD was not added, although the conversion proceeds, the conversion rate was delayed compared with the group in which FAD was added. Thus, as shown in Example 15-5, it was shown that the activation of NOX by the addition of the flavin coenzyme was effective for the conversion.

Example 21

Conversion of L-Fucitol by Recombinant *E. coli*

The experiment was performed to convert L-fucitol by intact microbial cells without purifying the produced enzyme from the microbial cells. The bacterial strains, *E. coli*/pUC18, *E. coli*/pIEX11, *E. coli*/pFEX3052, *E. coli*/pFNEX4105 and *E. coli*/pFNIEX5706 were used alone or in combination. As the standard reaction conditions, a reaction solution containing 120 mM L-fucitol, 0.2 M Gly-NaOH (pH 9.5), 50 µM riboflavin, 1 mM $MgCl_2$, and the washed microbial cells (adjusted to a final concentration in the reaction solution of $A_{610}$=5.0) was reacted at 30° C. with shaking, while sampling was appropriately performed. L-fucitol, L-fuculose, and L-fucose were quantified by HPLC. *E. coli*/pUC18, *E. coli*/pFEX3052, *E. coli*/pFNEX4105, and *E. coli*/pFNIEX5706 were used in the reactions having a single type of microbial cells. *E. coli*/pIEX11 was used as an additional second type of microbial cells. In the latter case, the final concentration of the first type of microbial cells was $A_{610}$=5.0, and the final concentration of *E. coli*/pIEX11 was $A_{610}$=2.5. The experimental groups and the results after 40 hours are shown in Table 15. The conversion time course in each experimental group is shown in FIG. 26.

TABLE 15

| EXPERI-MENTAL GROUP | BACTERIAL STRAIN | AFTER CONVERSION FOR 40 HOURS | | |
|---|---|---|---|---|
| | | L-FUCOSE (mM) | L-FUCULOSE (mM) | L-FUCITOL (mM) |
| A | *E. coli*/pUC18 | 0.0 | 0.0 | 123.8 |
| B | *E. coli*/pFEX3052 | 0.1 | 10.3 | 112.5 |
| C | *E. coli*/pFNEX4105 | 1.7 | 37.6 | 72.9 |
| D | *E. coli*/pUC18 + /pIEX11 | 0.3 | 0.0 | 128.9 |
| E | *E. coli*/pFEX3052 + /pIEX11 | 12.9 | 0.7 | 110.3 |
| F | *E. coli*/pFNEX4105 + /pIEX11 | 45.3 | 7.7 | 63.9 |
| G | *E. coli*/pFNIEX5706 | 95.7 | 13.0 | 12.2 |

Figure 26:
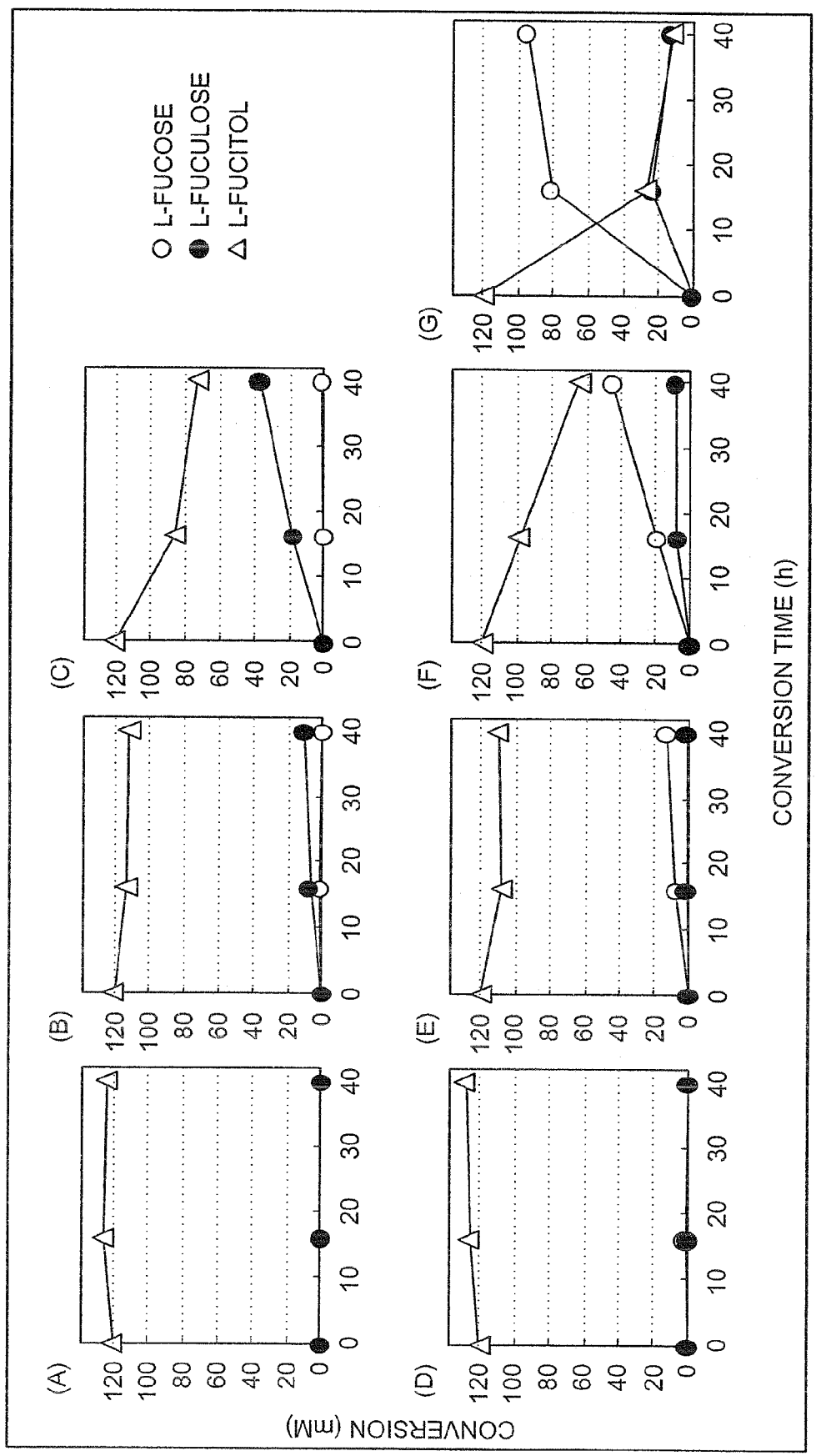
FIG. 26 shows the time courses of L-fucitol conversion by recombinant *E. coli* intact cells.

In each plot in FIG. 26, open circles, solid circles, and open triangles represent the concentrations of L-fucose, L-fuculose, and L-fucitol, respectively. The reaction solution was composed of 120 mM L-fucitol, 0.2 M Gly-NaOH (pH 9.5), 50 µM riboflavin, 1 mM $MgCl_2$, and the washed microbial cells adjusted to a final concentration in the reaction solution of $A_{610}$=5.0. (A) and (D) show the results using *E. coli*/pUC18, (B) and (E) show the results using *E. coli*/pFEX3052, (C) and (F) show the results using *E. coli*/pFNEX4105, and (G) shows the results using *E. coli*/pFNIEX5706. In (D), (E), and (F), the washed microbial cells of *E. coli*/pIEX11 adjusted to be $A_{610}$=2.5 were added in addition to the aforementioned composition.

As a result, as shown in the experimental group (B), the production of L-fuculose by the FcDH-expressing strain *E. coli*/pFEX3052 was observed whereas, as shown in the experimental group (A), L-fucitol was not converted at all by the control strain *E. coli*/pUC18. This demonstrates that NAD present in the host microbial cell can work as the coenzyme in the reaction by the intact microbial cell, and that the host has a slight NOX activity. The productivity of L-fuculose was enhanced in the experimental group (C) of the FcDH and NOX expressing strain *E. coli*/pFNEX4105 compared with the group of the FcDH expressing strain, suggesting that the expression of NOX might efficiently recycle NAD(H). As shown in the experimental groups (E) and (F), it was observed that L-fuculose which was produced was converted into L-fucose in the presence of FucI expressing strain *E. coli*/pIEX11 in the conversion by *E. coli*/pFEX3052 or *E. coli*/pFNEX4105. Furthermore, as shown in the experimental group (G), in the conversion using *E. coli*/pFNIEX5706 which expresses the three enzymes, FcDH, NOX and FucI, it was demonstrated that L-fucitol was converted into L-fucose by a single bacterial strain.

Example 22

Preparation of FcDH+NOX+FucI+KatE-Expressing Strain and Cultivation Thereof

The production of $H_2O_2$ derived from the NOX activity inhibited the conversion of L-fucitol, and the addition of catalase reversed this inhibition. Thus, a catalase gene was further introduced into the FcDH+NOX+FucI co-expressing strain, to obtain a bacterial strain which further co-expresses catalase. KatE protein derived from E. coli was used as catalase. The gene encoding this enzyme has been registered as accession number M55161 in the database in National Center for Biotechnology Information. To express large amounts of this enzyme in E. coli, the following PCR primers (SEQ ID NOS:28 and 29) were prepared. PCR was performed with the genomic DNA derived from E. coli W3110 strain as the template, to yield a fragment of about 2.5 kbp. The PCR product was digested with SalI and PstI, and introduced into the corresponding position into the plasmid pSTV28 (Takara Bio Inc.) to yield the plasmid pKEX5804 for KatE expression. E. coli/pFNIEX5706 strain was transformed with this plasmid to make the bacterial strain E. coli/FNIC7001, which has both plasmids pFNIEX5706 and pCEX8401.

This strain was refreshed by culturing on LB/Amp+Cm (chloramphenicol 0.03 mg/ml) plates at 37° C. The liquid cultivation was performed at 37° C. using the LB/Amp+Cm liquid medium. After inoculating the refreshed microbial cells, IPTG was added to a final concentration of 1 mM. The microbial cells were cultured for 6 to 18 hours, and then collected by centrifugation. The collected microbial cells were washed with 25 mM Tris-HCl buffer (pH 8.0), and used in the subsequent experiments. The TB medium (12 g/l trypton, 24 g/l yeast extract, 4 g/l glycerol, 2.3 g/l $KH_2PO_4$, 12.5 g/l $K_2HPO_4$) was used instead of the LB medium in some cases, and they were not essentially different except that a larger amount of the microbial cells was obtained.

Example 23

Measurement of Enzyme Activity in the Cell-Free Extract of the E. coli/FNIC7001 Strain After culturing at 30° C. or 37° C. using the TB medium, the microbial cells were collected. The washed microbial cells were resuspended in 25 mM Tris-HCl (pH 8.0), disrupted by sonication (200 W, 10 minutes), and centrifuged at 14,000 g for 15 minutes to yield the supernatant. This cell-free extract was used as the enzyme source to measure enzyme activity. E. coli/pFNIEX5706 strain was also used as a control.

The KatE activity was measured under standard condition. That is, 0.5 volume of 59 mM $H_2O_2$ was added to one volume of the enzyme solution appropriately diluted with 0.1M Tris-HCl (pH 8.0), and reacted at 30° C. The activity was quantified by monitoring the reduction of absorbance at 240 nm caused by the reduction of $H_2O_2$. As the absorbance coefficient of $H_2O_2$, $e_{240}=43.6 M^{-1} cm^{-1}$ was used. The measurement was started when $H_2O_2$ was added, and the activity was calculated by taking the change in absorbance in the first minute as the initial rate. The experimental group without the enzyme source was the blank. The KatE activity to consume 1 µmol $H_2O_2$ in one minute at 30° C. was defined as 1 U. The enzyme activity is shown in Table 16. At both 30° C. and 37° C., E. coli/FNIC7001 strain having pKEX5804 had higher KatE activity than E. coli/pFNIEX5706 strain.

TABLE 16

| Strain | Plasmid | CULTIVATION TEMPERATURE (° C.) | KatE ACTIVITY (U/mg) |
|---|---|---|---|
| E. coli/ pFNIEX5706 | pFNIEX5706 NO ADDITION OF NAD | 30 37 | 3.2 2.5 |
| E. coli/ FNIC7001 | pFNIEX5706 +pKEX5804 | 30 37 | 51.4 55.0 |

Example 24

Conversion of L-Fucitol by E. coli/FNIC7001 Strain

Figure 27:
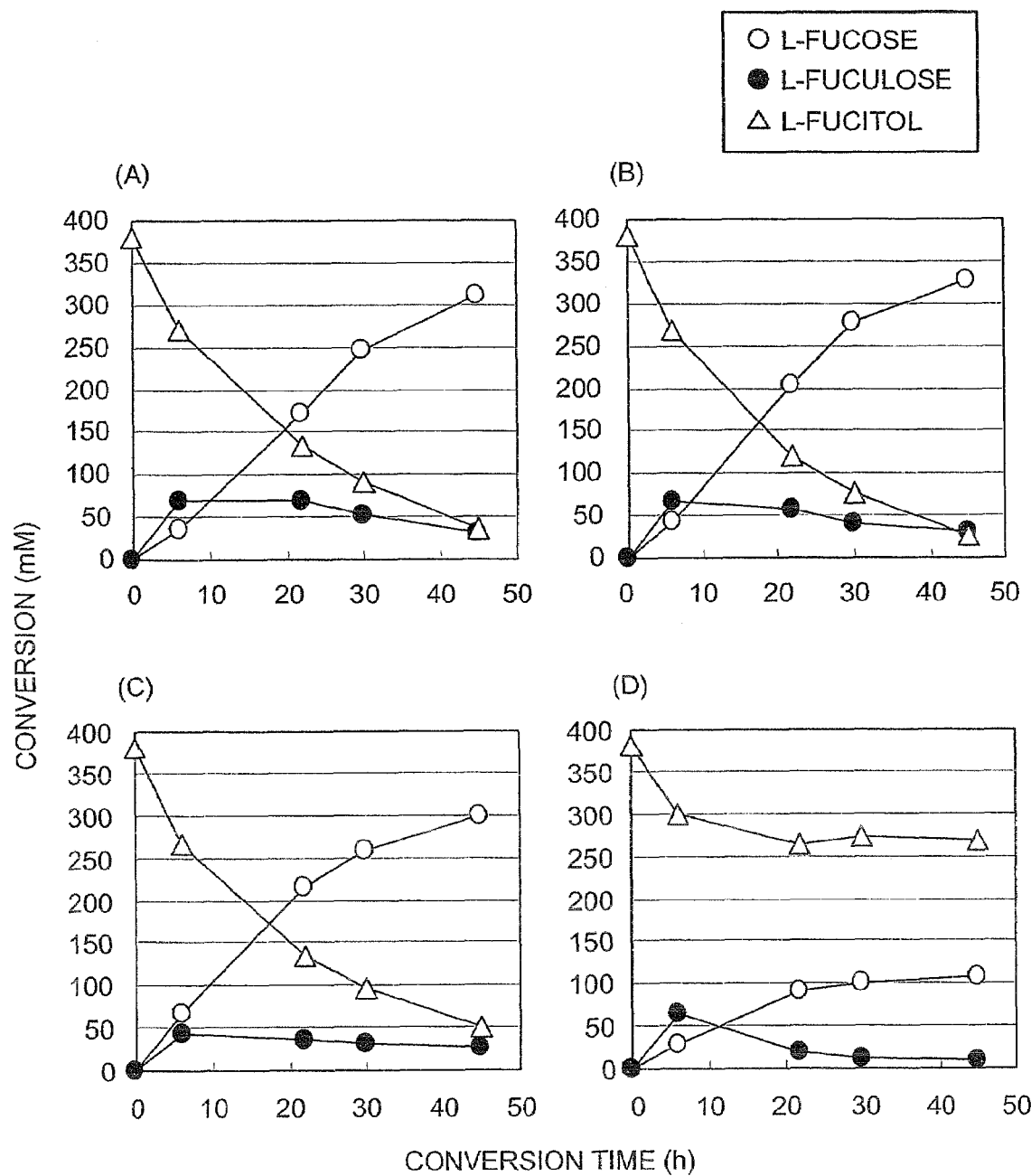
FIG. 27 shows the time courses of L-fucitol conversion in the presence of catalase.

The conversion experiment of L-fucitol by the washed intact microbial cells of E. coli/FNIC7001 strain cultured at 27, 30, 33, or 37° C. using TB/Amp+Cm was performed. The reaction solution containing 380 mM L-fucitol, 0.2 M Gly-NaOH (pH 9.5), 50 µM riboflavin, 1 mM $MnCl_2$, 0.1 mg/ml Amp, 0.03 mg/ml Cm, and washed microbial cells (adjusted so that the final concentration in the reaction solution was $A_{610}=10.0$) was reacted at 30° C. with shaking, while sampling was appropriately performed. L-fucitol, L-fuculose, and L-fucose were quantified by HPLC. The experimental groups and the analysis results after 45 hours are shown in Table 17, and the conversion time course in each experimental group is shown in FIG. 27. The enzyme activity in the cell-free extract prepared from the microbial cells cultured at each temperature is shown in Table 18.

TABLE 17

| EXPERIMENTAL GROUP | CULTIVATION TEMPERATURE OF BACTERIAL STRAIN (° C.) | AFTER CONVERSION FOR 45 HOURS | | |
| | | L-FUCOSE (mM) | L-FUCULOSE (mM) | L-FUCITOL (mM) |
|---|---|---|---|---|
| A | 27 | 312.2 | 31.3 | 36.2 |
| B | 30 | 327.1 | 30.3 | 26.9 |
| C | 33 | 299.4 | 27.4 | 50.3 |
| D | 37 | 108.5 | 9.0 | 269.3 |

TABLE 18

| CULTIVATION TEMPERATURE (°C.) | ENZYME ACTIVITY (U/mg) | | | |
|---|---|---|---|---|
| | FcDH | NOX | FucI | KatE |
| 27 | 0.57 | 1.32 | 0.41 | 51.3 |
| 30 | 0.65 | 1.62 | 0.42 | 52.0 |
| 33 | 1.63 | 4.71 | 0.87 | 57.3 |
| 37 | 2.05 | 6.49 | 0.92 | 50.8 |

In each plot in FIG. 27, open circles, solid circles, and open triangles represent the concentration of L-fucose, L-fuculose, and L-fucitol, respectively. The reaction solution was composed of 380 mM L-fucitol, 0.2 M Gly-NaOH (pH 9.5), 50 µM riboflavin, 1 mM $MgCl_2$, 0.1 mg/ml Amp, 0.03 mg/ml Cm, and the washed microbial cells adjusted so that the final concentration in the reaction solution was $A_{610}$=10.0. The microbial cells cultured at 27° C. (FIG. A) 30° C. (FIG. B), 33° C. (FIG. C) or 37° C. (FIG. D) were used for the conversion reaction.

As a result, the higher the microbial cell culture temperature, the higher the enzyme activity per unit protein amount. However, in the conversion reaction using the intact microbial cells, the conversion rate was faster when culturing at 27, 30 or 33° C. than at 37° C.

INDUSTRIAL APPLICABILITY

The present invention is suitable for the industrial production of L-fucose. The present invention is expected to contribute to various fields utilizing L-fucose.

SEQUENCE LISTING EXPLANATION

SEQ ID NO:1 5' Primer for obtaining fucI gene
SEQ ID NO:2 3' Primer for obtaining fucI gene
SEQ ID NO:3 Nucleotide sequence of fucI gene derived from *E. coli*
SEQ ID NO:4 Amino acid sequence of FucI derived from *E. coli*
SEQ ID NO:5 PCR primer for obtaining fucI gene
SEQ ID NO:6 PCR primer for obtaining fucI gene
SEQ ID NO:7 5' Primer for obtaining sldA gene
SEQ ID NO:8 3' Primer for obtaining sldA gene
SEQ ID NO:9 5' Primer for obtaining Kmr gene
SEQ ID NO:10 3' Primer for obtaining Kmr gene
SEQ ID NO:11 Amino acid sequence of peptide fragment F1 derived from FcDH
SEQ ID NO:12 Amino acid sequence of peptide fragment F2 derived from FcDH
SEQ ID NO:13 Amino acid sequence of peptide fragment N1 derived from NOX
SEQ ID NO:14 Amino acid sequence of peptide fragment N2 derived from NOX
SEQ ID NO:15 Nucleotide sequence of gene fcdh encoding FcDH
SEQ ID NO:16 Amino acid sequence of FcDH
SEQ ID NO:17 Nucleotide sequence of gene nox encoding NOX
SEQ ID NO:18 Amino acid sequence of NOX
SEQ ID NO:19 5' Primer for obtaining fcdh
SEQ ID NO:20 3' Primer for obtaining fcdh
SEQ ID NO:21 5' Primer for obtaining nox
SEQ ID NO:22 3' Primer for obtaining nox
SEQ ID NO:23 3' Primer for obtaining fcdh+nox
SEQ ID NO:24 5' Primer for obtaining fucI
SEQ ID NO:25 3' Primer for obtaining fucI
SEQ ID NO:26 5' Primer for obtaining fucI (single expression)
SEQ ID NO:27 3' Primer for obtaining fucI (single expression)
SEQ ID NO:28 5' Primer for obtaining KatE
SEQ ID NO:29 3' Primer for obtaining KatE

The invention claimed is:

1. An isolated polynucleotide selected from the group consisting of:
   (A) a polynucleotide comprising the nucleotide sequence of SEQ ID NO: 15,
   (B) a polynucleotide which hybridizes with a polynucleotide comprising a nucleotide sequence which is complementary to the full-length of the nucleotide sequence of SEQ ID NO:15 under stringent conditions comprising 1×SSC and 0.1% SDS at 60° C. and encodes a protein having a dehydrogenase activity which results in the synthesis L-fuculose from L-fucitol,
   (C) a polynucleotide which encodes a protein comprising the amino acid sequence of SEQ ID NO:16, and
   (D) a polynucleotide which encodes a protein comprising the amino acid sequence of SEQ ID No. 16, wherein said sequence includes one or several amino acid mutations selected from the group consisting of substitution, deletion, insertion, and addition, and wherein said sequence is at least 90% homologous to SEQ ID NO: 16, and said protein has a dehydrogenase activity which results in the synthesis of L-fuculose from L-fucitol.

2. The isolated polynucleotide of claim 1, wherein said polynucleotide is recombinant.

3. An isolated host cell comprising the polynucleotide according to claim 2, which is capable of expressing a protein having a dehydrogenase activity which results in the synthesis of L-fuculose from L-fucitol.

4. A method for producing a protein comprising culturing the host cell according to claim 3 in a medium, wherein the host cell is a microorganism, and wherein said protein accumulates in the medium and/or in the microorganism.

5. A method for producing L-fuculose comprising adding to a reaction system containing L-fucitol, a composition comprising the host cell according to claim 3, wherein L-fuculose is synthesized from L-fucitol.

6. A method for producing L-fucose comprising:
   synthesizing L-fuculose by adding to a reaction system containing L-fucitol, a composition comprising the host cell according to claim 3, and
   synthesizing L-fucose by contacting L-fuculose with a protein having L-fucose isomerase activity which results in the synthesis L-fucose from L-fuculose.

7. The isolated polynucleotide according to claim 1, wherein said polynucleotide in (D) encodes a protein comprising the amino acid sequence of SEQ ID NO: 16, wherein said sequence includes one or several amino acid mutations selected from the group consisting of substitution, deletion, insertion, and addition, and wherein said sequence is at least 95% homologous to SEQ ID NO: 16, and said protein has a dehydrogenase activity which results in the synthesis of L-fuculose from L-fucitol.

8. The isolated polynucleotide according to claim 7, wherein said polynucleotide is recombinant.

9. An isolated host cell comprising the polynucleotide according to claim 8, which is capable of expressing a protein having a dehydrogenase activity which results in the synthesis of L-fuculose from L-fucitol.

10. The isolated host cell according to claim 9, wherein said host cell is *Escherichia coli*.

11. A method for producing a protein comprising culturing the host cell according to claim 10 in a medium, wherein said protein accumulates in the medium and/or in the host cell.

12. A method for producing L-fuculose comprising adding to a reaction system containing L-fucitol, a composition comprising the host cell according to claim 10, wherein L-fuculose is synthesized from L-fucitol.

13. A method for producing L-fucose comprising:
synthesizing L-fuculose by adding to a reaction system containing L-fucitol, a composition comprising the host cell according to claim 10, and
synthesizing L-fucose by containing L-fuculose with a protein having L-fucose isomerase activity which results in the synthesis L-fucose from L-fuculose.

14. The isolated polynucleotide according to claim 1,
wherein said polynucleotide is selected from the group consisting of
(A) a polynucleotide comprising the nucleotide sequence of SEQ ID NO: 15, and
(C) a polynucleotide which encodes a protein comprising the amino acid sequence of SEQ ID NO:16.

15. The isolated polynucleotide according to claim 14, wherein said polynucleotide is recombinant.

16. An isolated host cell comprising the polynucleotide according to claim 15, which is capable of expressing a protein having a dehydrogenase activity which results in the synthesis of L-fuculose from L-fucitol.

17. The isolated host cell according to claim 16, wherein said host cell is *Escherichia coli*.

18. A method for producing a protein comprising culturing the host cell according to claim 17 in a medium, wherein said protein accumulates in the medium and/or in the host cell.

19. A method for producing L-fuculose comprising adding to a reaction system containing L-fucitol, a composition comprising the host cell according to claim 17, wherein L-fuculose is synthesized form L-fucitol.

20. A method for producing L-fucose comprising:
synthesizing L-fuculose by adding to a reaction system containing L-fucitol, a composition comprising the host cell according to claim 17, and
synthesizing L-fucose by containing L-fuculose with a protein having L-fucose isomerase activity which results in the synthesis L-fucose from L-fuculose.

21. The isolated host cell according to claim 3, wherein said host cell is *Escherichia coli*.

22. A method for producing a protein comprising culturing the host cell according to claim 21 in a medium, and wherein said protein accumulates in the medium and/or in the host cell.

23. A method for producing L-fuculose comprising adding to a reaction system containing L-fucitol, a composition comprising the host cell according to claim 21, wherein L-fuculose is synthesized from L-fucitol.

24. A method for producing L-fucose comprising:
synthesizing L-fuculose by adding to a reaction system containing L-fucitol, a composition comprising the host cell according to claim 21, and
synthesizing L-fucose by containing L-fuculose with a protein having L-fucose isomerase activity which results in the synthesis L-fucose from L-fuculose.

* * * * *

SEQUENCE LISTING

```
<160> NUMBER OF SEQ ID NOS: 29

<210> SEQ ID NO 1
<211> LENGTH: 30
<212> TYPE: DNA
<213> ORGANISM: Artificial
<220> FEATURE:
<223> OTHER INFORMATION: 5' primer to obtain fucI gene

<400> SEQUENCE: 1
gaagcatgca tgaaaaaaat cagcttaccg                                      30

<210> SEQ ID NO 2
<211> LENGTH: 30
<212> TYPE: DNA
<213> ORGANISM: artificial
<220> FEATURE:
<223> OTHER INFORMATION: 3' primer to obtain fucI gene

<400> SEQUENCE: 2
tgttcaggcc cggaagcttg agcgaccggg                                      30

<210> SEQ ID NO 3
<211> LENGTH: 1818
<212> TYPE: DNA
```

<213> ORGANISM: Escherichia coli
<220> FEATURE:
<221> NAME/KEY: CDS
<222> LOCATION: (1)..(1818)
<223> OTHER INFORMATION: fucIH6

<400> SEQUENCE: 3

```
atg aga gga tcg cat cac cat cac cat cac gga tcc gca tgc atg aaa      48
Met Arg Gly Ser His His His His His His Gly Ser Ala Cys Met Lys
1               5                   10                  15 aaa atc agc tta ccg aaa att ggt atc cgc ccg gtt att gac ggt cgt      96
Lys Ile Ser Leu Pro Lys Ile Gly Ile Arg Pro Val Ile Asp Gly Arg
            20                  25                  30 cgc atg ggt gtt cgt gag tcg ctt gaa gaa caa aca atg aat atg gcg     144
Arg Met Gly Val Arg Glu Ser Leu Glu Glu Gln Thr Met Asn Met Ala
        35                  40                  45 aaa gct acg gcc gca ctg ctg acc gag aaa ctg cgc cat gcc tgc gga     192
Lys Ala Thr Ala Ala Leu Leu Thr Glu Lys Leu Arg His Ala Cys Gly
    50                  55                  60 gct gcc gtc gag tgt gtc att tcc gat acc tgt atc gcg ggt atg gct     240
Ala Ala Val Glu Cys Val Ile Ser Asp Thr Cys Ile Ala Gly Met Ala
65                  70                  75                  80 gaa gcc gct gct tgc gaa gaa aaa ttc agc agt cag aat gta ggc ctc     288
Glu Ala Ala Ala Cys Glu Glu Lys Phe Ser Ser Gln Asn Val Gly Leu
                85                  90                  95 acc att acg gta acg cct tgc tgg tgc tat ggc agt gaa acc atc gac     336
Thr Ile Thr Val Thr Pro Cys Trp Cys Tyr Gly Ser Glu Thr Ile Asp
            100                 105                 110 atg gat cca acc cgc ccg aag gcc att tgg ggc ttt aac ggc act gaa     384
Met Asp Pro Thr Arg Pro Lys Ala Ile Trp Gly Phe Asn Gly Thr Glu
        115                 120                 125 cgc ccc ggc gct gtt tac ctg gca gcg gct ctg gca gct cac agc cag     432
Arg Pro Gly Ala Val Tyr Leu Ala Ala Ala Leu Ala Ala His Ser Gln
    130                 135                 140 aaa ggc atc cca gca ttc tcc att tac ggt cat gac gtt cag gat gcc     480
Lys Gly Ile Pro Ala Phe Ser Ile Tyr Gly His Asp Val Gln Asp Ala
145                 150                 155                 160 gat gac aca tcg att cct gcc gat gtt gaa gaa aaa ctg ctg cgc ttt     528
Asp Asp Thr Ser Ile Pro Ala Asp Val Glu Glu Lys Leu Leu Arg Phe
                165                 170                 175 gcc cgc gcc ggt ttg gcc gtc gcc agc atg aaa ggt aaa agc tat ctg     576
Ala Arg Ala Gly Leu Ala Val Ala Ser Met Lys Gly Lys Ser Tyr Leu
            180                 185                 190 tcg ctg ggc ggc gtt tcg atg ggt atc gcc ggt tcc att gtt gat cac     624
Ser Leu Gly Gly Val Ser Met Gly Ile Ala Gly Ser Ile Val Asp His
        195                 200                 205 aac ttc ttt gaa tcc tgg ctg gga atg aaa gtc cag gcg gtg gat atg     672
Asn Phe Phe Glu Ser Trp Leu Gly Met Lys Val Gln Ala Val Asp Met
    210                 215                 220 acc gaa ctg cgt cgc cgt atc gat cag aag att tac gac gaa gcc gaa     720
Thr Glu Leu Arg Arg Arg Ile Asp Gln Lys Ile Tyr Asp Glu Ala Glu
225                 230                 235                 240 ttg gaa atg gca ctg gcc tgg gct gat aaa aac ttc cgc tat ggc gaa     768
Leu Glu Met Ala Leu Ala Trp Ala Asp Lys Asn Phe Arg Tyr Gly Glu
                245                 250                 255 gat gaa aat aac aaa cag tat caa cgt aat gcc gag caa agc cgc gca     816
Asp Glu Asn Asn Lys Gln Tyr Gln Arg Asn Ala Glu Gln Ser Arg Ala
            260                 265                 270 gtt ctg cgc gaa agt tta ctg atg gcg atg tgt atc cgc gac atg atg     864
Val Leu Arg Glu Ser Leu Leu Met Ala Met Cys Ile Arg Asp Met Met
        275                 280                 285
```

-continued

```
caa ggc aac agc aaa ctg gcc gat att ggt cgc gtg gaa gaa tca ctt       912
Gln Gly Asn Ser Lys Leu Ala Asp Ile Gly Arg Val Glu Glu Ser Leu
        290                 295                 300 ggc tac aac gcc atc gct gcg ggc ttc cag ggg caa cgt cac tgg acc       960
Gly Tyr Asn Ala Ile Ala Ala Gly Phe Gln Gly Gln Arg His Trp Thr
305                 310                 315                 320 gat caa tat ccc aat ggt gac acc gcc gaa gcg atc ctc aac agt tca      1008
Asp Gln Tyr Pro Asn Gly Asp Thr Ala Glu Ala Ile Leu Asn Ser Ser
                325                 330                 335 ttt gac tgg aat ggc gtg cgc gaa ccc ttt gtc gtg gcg acc gaa aac      1056
Phe Asp Trp Asn Gly Val Arg Glu Pro Phe Val Val Ala Thr Glu Asn
            340                 345                 350 gac agt ctt aac ggc gtg gca atg cta atg ggt cac cag ctc acc ggc      1104
Asp Ser Leu Asn Gly Val Ala Met Leu Met Gly His Gln Leu Thr Gly
        355                 360                 365 acc gct cag gta ttt gcc gat gtg cgt acc tac tgg tca cca gaa gca      1152
Thr Ala Gln Val Phe Ala Asp Val Arg Thr Tyr Trp Ser Pro Glu Ala
370                 375                 380 att gag cgt gta acg ggg cat aaa ctg gat gga ctg gca gaa cac ggc      1200
Ile Glu Arg Val Thr Gly His Lys Leu Asp Gly Leu Ala Glu His Gly
385                 390                 395                 400 atc atc cat ttg atc aac tcc ggt tct gct gcg ctg gac ggt tcc tgt      1248
Ile Ile His Leu Ile Asn Ser Gly Ser Ala Ala Leu Asp Gly Ser Cys
                405                 410                 415 aaa caa cgc gac agc gaa ggt aac ccg acg atg aag cca cac tgg gaa      1296
Lys Gln Arg Asp Ser Glu Gly Asn Pro Thr Met Lys Pro His Trp Glu
            420                 425                 430 atc tct cag caa gag gct gac gct tgc ctc gcc gct acc gaa tgg tgc      1344
Ile Ser Gln Gln Glu Ala Asp Ala Cys Leu Ala Ala Thr Glu Trp Cys
        435                 440                 445 ccg gcg atc cac gaa tac ttc cgt ggc ggt ggt tac tct tcc cgc ttc      1392
Pro Ala Ile His Glu Tyr Phe Arg Gly Gly Gly Tyr Ser Ser Arg Phe
450                 455                 460 ctt acc gaa ggc ggc gtc ccg ttc acc atg act cgt gtc aac atc atc      1440
Leu Thr Glu Gly Gly Val Pro Phe Thr Met Thr Arg Val Asn Ile Ile
465                 470                 475                 480 aaa ggc ctg gga ccg gta ctg caa atc gcg gaa ggc tgg agc gtg gaa      1488
Lys Gly Leu Gly Pro Val Leu Gln Ile Ala Glu Gly Trp Ser Val Glu
                485                 490                 495 ttg ccg aag gat gtg cat gac atc ctc aac aaa cgc acc aac tca acc      1536
Leu Pro Lys Asp Val His Asp Ile Leu Asn Lys Arg Thr Asn Ser Thr
            500                 505                 510 tgg cca acc acc tgg ttt gca ccg cgc ctc acc ggt aaa ggg ccg ttt      1584
Trp Pro Thr Thr Trp Phe Ala Pro Arg Leu Thr Gly Lys Gly Pro Phe
        515                 520                 525 acg gat gtg tac tcg gta atg gcg aac tgg ggc gct aac cat ggg gtt      1632
Thr Asp Val Tyr Ser Val Met Ala Asn Trp Gly Ala Asn His Gly Val
530                 535                 540 ctg acc atc ggc cac gtt ggc gca gac ttt atc act ctc gcc tcc atg      1680
Leu Thr Ile Gly His Val Gly Ala Asp Phe Ile Thr Leu Ala Ser Met
545                 550                 555                 560 ctg cgt atc ccg gta tgt atg cac aac gtt gaa gag acc aaa gtg tat      1728
Leu Arg Ile Pro Val Cys Met His Asn Val Glu Glu Thr Lys Val Tyr
                565                 570                 575 cgt cct tct gcc tgg gct gcg cac ggc atg gat att gaa ggc cag gat      1776
Arg Pro Ser Ala Trp Ala Ala His Gly Met Asp Ile Glu Gly Gln Asp
            580                 585                 590 tac cgc gct tgc cag aac tac ggt ccg ttg tac aag cgt taa              1818
Tyr Arg Ala Cys Gln Asn Tyr Gly Pro Leu Tyr Lys Arg
```

```
            595                 600                 605

<210> SEQ ID NO 4
<211> LENGTH: 605
<212> TYPE: PRT
<213> ORGANISM: Escherichia coli

<400> SEQUENCE: 4

Met Arg Gly Ser His His His His His Gly Ser Ala Cys Met Lys
1               5                   10                  15

Lys Ile Ser Leu Pro Lys Ile Gly Ile Arg Pro Val Ile Asp Gly
                20                  25                  30

Arg Met Gly Val Arg Glu Ser Leu Glu Glu Gln Thr Met Asn Met Ala
            35                  40                  45

Lys Ala Thr Ala Ala Leu Leu Thr Glu Lys Leu Arg His Ala Cys Gly
50                  55                  60

Ala Ala Val Glu Cys Val Ile Ser Asp Thr Cys Ile Ala Gly Met Ala
65                  70                  75                  80

Glu Ala Ala Ala Cys Glu Glu Lys Phe Ser Ser Gln Asn Val Gly Leu
                85                  90                  95

Thr Ile Thr Val Thr Pro Cys Trp Cys Tyr Gly Ser Glu Thr Ile Asp
                100                 105                 110

Met Asp Pro Thr Arg Pro Lys Ala Ile Trp Gly Phe Asn Gly Thr Glu
                115                 120                 125

Arg Pro Gly Ala Val Tyr Leu Ala Ala Ala Leu Ala Ala His Ser Gln
            130                 135                 140

Lys Gly Ile Pro Ala Phe Ser Ile Tyr Gly His Asp Val Gln Asp Ala
145                 150                 155                 160

Asp Asp Thr Ser Ile Pro Ala Asp Val Glu Glu Lys Leu Leu Arg Phe
                165                 170                 175

Ala Arg Ala Gly Leu Ala Val Ala Ser Met Lys Gly Lys Ser Tyr Leu
                180                 185                 190

Ser Leu Gly Gly Val Ser Met Gly Ile Ala Gly Ser Ile Val Asp His
                195                 200                 205

Asn Phe Phe Glu Ser Trp Leu Gly Met Lys Val Gln Ala Val Asp Met
        210                 215                 220

Thr Glu Leu Arg Arg Arg Ile Asp Gln Lys Ile Tyr Asp Glu Ala Glu
225                 230                 235                 240

Leu Glu Met Ala Leu Ala Trp Ala Asp Lys Asn Phe Arg Tyr Gly Glu
                245                 250                 255

Asp Glu Asn Asn Lys Gln Tyr Gln Arg Asn Ala Glu Gln Ser Arg Ala
                260                 265                 270

Val Leu Arg Glu Ser Leu Leu Met Ala Met Cys Ile Arg Asp Met Met
                275                 280                 285

Gln Gly Asn Ser Lys Leu Ala Asp Ile Gly Arg Val Glu Glu Ser Leu
        290                 295                 300

Gly Tyr Asn Ala Ile Ala Ala Gly Phe Gln Gly Gln Arg His Trp Thr
305                 310                 315                 320

Asp Gln Tyr Pro Asn Gly Asp Thr Ala Glu Ala Ile Leu Asn Ser Ser
                325                 330                 335

Phe Asp Trp Asn Gly Val Arg Glu Pro Phe Val Val Ala Thr Glu Asn
                340                 345                 350

Asp Ser Leu Asn Gly Val Ala Met Leu Met Gly His Gln Leu Thr Gly
        355                 360                 365
```

```
Thr Ala Gln Val Phe Ala Asp Val Arg Thr Tyr Trp Ser Pro Glu Ala
    370                 375                 380

Ile Glu Arg Val Thr Gly His Lys Leu Asp Gly Leu Ala Glu His Gly
385                 390                 395                 400

Ile Ile His Leu Ile Asn Ser Gly Ser Ala Ala Leu Asp Gly Ser Cys
                405                 410                 415

Lys Gln Arg Asp Ser Glu Gly Asn Pro Thr Met Lys Pro His Trp Glu
            420                 425                 430

Ile Ser Gln Gln Glu Ala Asp Ala Cys Leu Ala Thr Glu Trp Cys
        435                 440                 445

Pro Ala Ile His Glu Tyr Phe Arg Gly Gly Tyr Ser Ser Arg Phe
    450                 455                 460

Leu Thr Glu Gly Gly Val Pro Phe Thr Met Thr Arg Val Asn Ile Ile
465                 470                 475                 480

Lys Gly Leu Gly Pro Val Leu Gln Ile Ala Glu Gly Trp Ser Val Glu
                485                 490                 495

Leu Pro Lys Asp Val His Asp Ile Leu Asn Lys Arg Thr Asn Ser Thr
            500                 505                 510

Trp Pro Thr Thr Trp Phe Ala Pro Arg Leu Thr Gly Lys Gly Pro Phe
        515                 520                 525

Thr Asp Val Tyr Ser Val Met Ala Asn Trp Gly Ala Asn His Gly Val
    530                 535                 540

Leu Thr Ile Gly His Val Gly Ala Asp Phe Ile Thr Leu Ala Ser Met
545                 550                 555                 560

Leu Arg Ile Pro Val Cys Met His Asn Val Glu Thr Lys Val Tyr
                565                 570                 575

Arg Pro Ser Ala Trp Ala Ala His Gly Met Asp Ile Glu Gly Gln Asp
            580                 585                 590

Tyr Arg Ala Cys Gln Asn Tyr Gly Pro Leu Tyr Lys Arg
        595                 600                 605

<210> SEQ ID NO 5
<211> LENGTH: 30
<212> TYPE: DNA
<213> ORGANISM: Artificial
<220> FEATURE:
<223> OTHER INFORMATION: primer for obtaining fucI gene

<400> SEQUENCE: 5
aactgaattc attttccgaa taaagtgagg                                  30

<210> SEQ ID NO 6
<211> LENGTH: 30
<212> TYPE: DNA
<213> ORGANISM: Artificial
<220> FEATURE:
<223> OTHER INFORMATION: primer for obtaining fucI gene

<400> SEQUENCE: 6
gttcaggccc tgcagccgga gcgaccgggc                                  30

<210> SEQ ID NO 7
<211> LENGTH: 35
<212> TYPE: DNA
<213> ORGANISM: artificial
<220> FEATURE:
<223> OTHER INFORMATION: 5' primer to obtain a internal sequence of sldA

<400> SEQUENCE: 7
```

```
gccggcggta ccttctagca acagccgcag gactc                                    35
```

<210> SEQ ID NO 8
<211> LENGTH: 35
<212> TYPE: DNA
<213> ORGANISM: artificial
<220> FEATURE:
<223> OTHER INFORMATION: 3' primer to obtain a internal sequence of sldA

<400> SEQUENCE: 8

```
acaccttgtc tgcagcatca ctacgcaggg cgctg                                    35
```

<210> SEQ ID NO 9
<211> LENGTH: 35
<212> TYPE: DNA
<213> ORGANISM: artificial
<220> FEATURE:
<223> OTHER INFORMATION: 5' primer to obtain kmr gene

<400> SEQUENCE: 9

```
taaaactgga tccttacata aacagtaata caagg                                    35
```

<210> SEQ ID NO 10
<211> LENGTH: 35
<212> TYPE: DNA
<213> ORGANISM: artificial
<220> FEATURE:
<223> OTHER INFORMATION: 3' primer to obtain Kmr gene

<400> SEQUENCE: 10

```
atgctctgcc agatctacaa ccaattaacc aattc                                    35
```

<210> SEQ ID NO 11
<211> LENGTH: 12
<212> TYPE: PRT
<213> ORGANISM: Gluconobacter oxydans

<400> SEQUENCE: 11

```
Ser Leu Ala Ala Glu Trp Ala Pro Tyr Gly Ile Arg
1               5                   10
```

<210> SEQ ID NO 12
<211> LENGTH: 15
<212> TYPE: PRT
<213> ORGANISM: Gluconobacter oxydans

<400> SEQUENCE: 12

```
Phe Gly Met Glu Lys Pro Glu Leu Tyr Asp Ala Trp Ala Ile Gly
1               5                   10                  15
```

<210> SEQ ID NO 13
<211> LENGTH: 15
<212> TYPE: PRT
<213> ORGANISM: Gluconobacter oxydans

<400> SEQUENCE: 13

```
Phe Gly Leu Ser Ile Leu Asn Asn Ser His Lys Asp Val Ala Met
1               5                   10                  15
```

<210> SEQ ID NO 14
<211> LENGTH: 15
<212> TYPE: PRT
<213> ORGANISM: Gluconobacter oxydans

<400> SEQUENCE: 14

```
Pro Thr Ser Ile Thr Val Arg Asp Glu Ala Pro Leu Leu Tyr Phe
1               5                   10                  15

<210> SEQ ID NO 15
<211> LENGTH: 774
<212> TYPE: DNA
<213> ORGANISM: Gluconobacter oxydans
<220> FEATURE:
<221> NAME/KEY: CDS
<222> LOCATION: (1)..(774)
<223> OTHER INFORMATION: gene for fudh

<400> SEQUENCE: 15 atg tac atg gaa aaa ctt cgt ctc gat ggc cgc acc gca gtt gtc act        48
Met Tyr Met Glu Lys Leu Arg Leu Asp Gly Arg Thr Ala Val Val Thr
1               5                   10                  15 ggc ggc gca cag aac atc ggt ctg gcc tgc gtg acg gca ctg gcc gaa        96
Gly Gly Ala Gln Asn Ile Gly Leu Ala Cys Val Thr Ala Leu Ala Glu
            20                  25                  30 gcc ggg gcg cgt gtt gtg att gcg gat ctg gat gag gcc atg gcc gca       144
Ala Gly Ala Arg Val Val Ile Ala Asp Leu Asp Glu Ala Met Ala Ala
        35                  40                  45 caa tct gcg gag gaa ctc tgc gca gag ggc ctg gac gtc aga agc atc       192
Gln Ser Ala Glu Glu Leu Cys Ala Glu Gly Leu Asp Val Arg Ser Ile
    50                  55                  60 cgc atg gat gtc acg agc atg gaa aat gtt cag gca gcc atc aag acc       240
Arg Met Asp Val Thr Ser Met Glu Asn Val Gln Ala Ala Ile Lys Thr
65                  70                  75                  80 ctg cac gag cag gaa ggc cat ctg gat att ctg gtg gcc tgt gcg ggg       288
Leu His Glu Gln Glu Gly His Leu Asp Ile Leu Val Ala Cys Ala Gly
                85                  90                  95 atc tgc att tcc gaa gtc aaa gct gag gac atg acg gaa ggt cag tgg       336
Ile Cys Ile Ser Glu Val Lys Ala Glu Asp Met Thr Glu Gly Gln Trp
            100                 105                 110 ctc aag cag gtc gat atc aac ctg aac ggc atg ttc cgt tgc tgt cag       384
Leu Lys Gln Val Asp Ile Asn Leu Asn Gly Met Phe Arg Cys Cys Gln
        115                 120                 125 gcc gtg ggt cgc atc atg ctt gag cag aag aaa ggc gcg att gtc gcc       432
Ala Val Gly Arg Ile Met Leu Glu Gln Lys Lys Gly Ala Ile Val Ala
    130                 135                 140 atc gga tcc atg tcc ggg caa atc gtc aac cgc cca cag cag cag gcc       480
Ile Gly Ser Met Ser Gly Gln Ile Val Asn Arg Pro Gln Gln Gln Ala
145                 150                 155                 160 gcc tat aat gcc tcc aag gcg ggt gtg cac cag tat atc cgc tca ctt       528
Ala Tyr Asn Ala Ser Lys Ala Gly Val His Gln Tyr Ile Arg Ser Leu
                165                 170                 175 gcg gcg gaa tgg gcg cct tat ggt atc cgt gcc aat gca gtt gct ccg       576
Ala Ala Glu Trp Ala Pro Tyr Gly Ile Arg Ala Asn Ala Val Ala Pro
            180                 185                 190 acc tac atc gaa aca aca ctg aca cgc ttc ggt atg gaa aag ccg gaa       624
Thr Tyr Ile Glu Thr Thr Leu Thr Arg Phe Gly Met Glu Lys Pro Glu
        195                 200                 205 ctg tat gat gcg tgg att gcc gga aca ccg atg ggg cgc gtg ggg cag       672
Leu Tyr Asp Ala Trp Ile Ala Gly Thr Pro Met Gly Arg Val Gly Gln
    210                 215                 220 ccc gac gaa gtc gcc tcc gtc gtg cac ttt ctg gcc tcg gat gcc gca       720
Pro Asp Glu Val Ala Ser Val Val His Phe Leu Ala Ser Asp Ala Ala
225                 230                 235                 240 agc ctg atg acg ggt tcc atc gtc aac gtg gat gct ggt ttc acc gtc       768
Ser Leu Met Thr Gly Ser Ile Val Asn Val Asp Ala Gly Phe Thr Val
                245                 250                 255
```

```
tgg taa                                                              774
Trp
```

<210> SEQ ID NO 16
<211> LENGTH: 257
<212> TYPE: PRT
<213> ORGANISM: Gluconobacter oxydans

<400> SEQUENCE: 16

```
Met Tyr Met Glu Lys Leu Arg Leu Asp Gly Arg Thr Ala Val Val Thr
1               5                   10                  15

Gly Gly Ala Gln Asn Ile Gly Leu Ala Cys Val Thr Ala Leu Ala Glu
            20                  25                  30

Ala Gly Ala Arg Val Val Ile Ala Asp Leu Asp Glu Ala Met Ala Ala
        35                  40                  45

Gln Ser Ala Glu Glu Leu Cys Ala Glu Gly Leu Asp Val Arg Ser Ile
    50                  55                  60

Arg Met Asp Val Thr Ser Met Glu Asn Val Gln Ala Ala Ile Lys Thr
65                  70                  75                  80

Leu His Glu Gln Glu Gly His Leu Asp Ile Leu Val Ala Cys Ala Gly
                85                  90                  95

Ile Cys Ile Ser Glu Val Lys Ala Glu Asp Met Thr Glu Gly Gln Trp
            100                 105                 110

Leu Lys Gln Val Asp Ile Asn Leu Asn Gly Met Phe Arg Cys Cys Gln
        115                 120                 125

Ala Val Gly Arg Ile Met Leu Glu Gln Lys Lys Gly Ala Ile Val Ala
    130                 135                 140

Ile Gly Ser Met Ser Gly Gln Ile Val Asn Arg Pro Gln Gln Gln Ala
145                 150                 155                 160

Ala Tyr Asn Ala Ser Lys Ala Gly Val His Gln Tyr Ile Arg Ser Leu
                165                 170                 175

Ala Ala Glu Trp Ala Pro Tyr Gly Ile Arg Ala Asn Ala Val Ala Pro
            180                 185                 190

Thr Tyr Ile Glu Thr Thr Leu Thr Arg Phe Gly Met Glu Lys Pro Glu
        195                 200                 205

Leu Tyr Asp Ala Trp Ile Ala Gly Thr Pro Met Gly Arg Val Gly Gln
    210                 215                 220

Pro Asp Glu Val Ala Ser Val Val His Phe Leu Ala Ser Asp Ala Ala
225                 230                 235                 240

Ser Leu Met Thr Gly Ser Ile Val Asn Val Asp Ala Gly Phe Thr Val
                245                 250                 255

Trp
```

<210> SEQ ID NO 17
<211> LENGTH: 474
<212> TYPE: DNA
<213> ORGANISM: Gluconobacter oxydans
<220> FEATURE:
<221> NAME/KEY: CDS
<222> LOCATION: (1)..(474)
<223> OTHER INFORMATION: gene for nox

<400> SEQUENCE: 17

```
atg acg ata ctg aat gag cag gac ttt cgc cgg gcc atg tcc cat ttc      48
Met Thr Ile Leu Asn Glu Gln Asp Phe Arg Arg Ala Met Ser His Phe
1               5                   10                  15 gcg acg ggt gtg gct gtt gtg aca gcc aag gga agc gaa ggc gag caa      96
Ala Thr Gly Val Ala Val Val Thr Ala Lys Gly Ser Glu Gly Glu Gln
```

```
                20                  25                  30
ggg gcg acc atc agc gcc ctg aca tct gtt tcc cta gac ccg ctg ctg     144
Gly Ala Thr Ile Ser Ala Leu Thr Ser Val Ser Leu Asp Pro Leu Leu
         35                  40                  45 ctg ctg atc tgc ctg cat cgt ggc agc tcg act tac aag gcg att gct     192
Leu Leu Ile Cys Leu His Arg Gly Ser Ser Thr Tyr Lys Ala Ile Ala
 50                  55                  60 gag gca ggc cgt ttc ggt ctc agc att ctg aac aac agc cat aag gac     240
Glu Ala Gly Arg Phe Gly Leu Ser Ile Leu Asn Asn Ser His Lys Asp
 65                  70                  75                  80 gtg gcc atg ctg ttc gcc agc cgc acg gca gac aaa ttt gga tca gac     288
Val Ala Met Leu Phe Ala Ser Arg Thr Ala Asp Lys Phe Gly Ser Asp
                 85                  90                  95 gtt gtg gta cgg gca gaa gat ggt acg gct ttc att gat ggc gca ctg     336
Val Val Val Arg Ala Glu Asp Gly Thr Ala Phe Ile Asp Gly Ala Leu
            100                 105                 110 gta cag atg cat tgt gag ctt gtg gag acg ttc cag ggt ggc aca cat     384
Val Gln Met His Cys Glu Leu Val Glu Thr Phe Gln Gly Gly Thr His
        115                 120                 125 gcg ctc ttc atg gcg cgt cca acc agc atc acc gtc cgg gat gaa gca     432
Ala Leu Phe Met Ala Arg Pro Thr Ser Ile Thr Val Arg Asp Glu Ala
    130                 135                 140 ccg ctt ctg tac ttc cag gga cag ctg ggg gtt gag gcg taa             474
Pro Leu Leu Tyr Phe Gln Gly Gln Leu Gly Val Glu Ala
145                 150                 155

<210> SEQ ID NO 18
<211> LENGTH: 157
<212> TYPE: PRT
<213> ORGANISM: Gluconobacter oxydans

<400> SEQUENCE: 18

Met Thr Ile Leu Asn Glu Gln Asp Phe Arg Arg Ala Met Ser His Phe
 1               5                  10                  15

Ala Thr Gly Val Ala Val Val Thr Ala Lys Gly Ser Glu Gly Glu Gln
                20                  25                  30

Gly Ala Thr Ile Ser Ala Leu Thr Ser Val Ser Leu Asp Pro Leu Leu
         35                  40                  45

Leu Leu Ile Cys Leu His Arg Gly Ser Ser Thr Tyr Lys Ala Ile Ala
 50                  55                  60

Glu Ala Gly Arg Phe Gly Leu Ser Ile Leu Asn Asn Ser His Lys Asp
 65                  70                  75                  80

Val Ala Met Leu Phe Ala Ser Arg Thr Ala Asp Lys Phe Gly Ser Asp
                 85                  90                  95

Val Val Val Arg Ala Glu Asp Gly Thr Ala Phe Ile Asp Gly Ala Leu
            100                 105                 110

Val Gln Met His Cys Glu Leu Val Glu Thr Phe Gln Gly Gly Thr His
        115                 120                 125

Ala Leu Phe Met Ala Arg Pro Thr Ser Ile Thr Val Arg Asp Glu Ala
    130                 135                 140

Pro Leu Leu Tyr Phe Gln Gly Gln Leu Gly Val Glu Ala
145                 150                 155

<210> SEQ ID NO 19
<211> LENGTH: 30
<212> TYPE: DNA
<213> ORGANISM: Artificial
<220> FEATURE:
<223> OTHER INFORMATION: 5'primer to obtain fcdh
```

<400> SEQUENCE: 19
gcctgaattc aggaatattc aagatgtaca                                    30

<210> SEQ ID NO 20
<211> LENGTH: 35
<212> TYPE: DNA
<213> ORGANISM: Artificial
<220> FEATURE:
<223> OTHER INFORMATION: 3'primer to obtain fcdh

<400> SEQUENCE: 20
gatgagccgc tgcagttaat atgtccggac ctgac                              35

<210> SEQ ID NO 21
<211> LENGTH: 35
<212> TYPE: DNA
<213> ORGANISM: Artificial
<220> FEATURE:
<223> OTHER INFORMATION: 5'primer to obtain nox

<400> SEQUENCE: 21
ctgtaaggct gcaggaacca aggattccga cgatg                              35

<210> SEQ ID NO 22
<211> LENGTH: 35
<212> TYPE: DNA
<213> ORGANISM: Artificial
<220> FEATURE:
<223> OTHER INFORMATION: 3'primer to obtain nox

<400> SEQUENCE: 22
attccgaaaa agcttcgtaa tttccatcac ttttc                              35

<210> SEQ ID NO 23
<211> LENGTH: 35
<212> TYPE: DNA
<213> ORGANISM: Artificial
<220> FEATURE:
<223> OTHER INFORMATION: 3'primer to obtain fcdh + nox

<400> SEQUENCE: 23
gcaccgcatg gtacccagac ggaaacgcct gctta                              35

<210> SEQ ID NO 24
<211> LENGTH: 35
<212> TYPE: DNA
<213> ORGANISM: Artificial
<220> FEATURE:
<223> OTHER INFORMATION: 5'primer to obtain fucI

<400> SEQUENCE: 24
cggcaactgg taccacatat tttccgaata aagtg                              35

<210> SEQ ID NO 25
<211> LENGTH: 30
<212> TYPE: DNA
<213> ORGANISM: Artificial
<220> FEATURE:
<223> OTHER INFORMATION: 3'primer to obtain fucI

<400> SEQUENCE: 25
gttcaggccg tcgacccgga gcgaccgggc                                    30

<210> SEQ ID NO 26

```
<211> LENGTH: 34
<212> TYPE: DNA
<213> ORGANISM: Artificial
<220> FEATURE:
<223> OTHER INFORMATION: 5' primer to obtain fucI

<400> SEQUENCE: 26
aactgaattc acatattttc cgaataaagt gagg                                34

<210> SEQ ID NO 27
<211> LENGTH: 30
<212> TYPE: DNA
<213> ORGANISM: Artificial
<220> FEATURE:
<223> OTHER INFORMATION: 3'primer to obtain fucI

<400> SEQUENCE: 27
gttcaggccc tgcagcccga gcgaccgggc                                    30

<210> SEQ ID NO 28
<211> LENGTH: 35
<212> TYPE: DNA
<213> ORGANISM: Artificial
<220> FEATURE:
<223> OTHER INFORMATION: 5'Primer to obtain KatE

<400> SEQUENCE: 28
ggcttcacta gtcgactatt aaaaatcaga aaaac                              35

<210> SEQ ID NO 29
<211> LENGTH: 35
<212> TYPE: DNA
<213> ORGANISM: Artificial
<220> FEATURE:
<223> OTHER INFORMATION: 3'Primer to obtain KatE

<400> SEQUENCE: 29
atgtaaatcc tgcaggcggc gcaattgcgc gctcc                              35
```